(12) United States Patent
Wang et al.

(10) Patent No.: US 9,598,694 B2
(45) Date of Patent: Mar. 21, 2017

(54) MICRO-RNAS INVOLVED IN MACULAR DEGENERATION

(71) Applicant: The Board of Regents of the University of Texas System, Austin, TX (US)

(72) Inventors: Shusheng Wang, New Orleans, LA (US); Eric Olson, Dallas, TX (US); Qinbo Zhou, Dallas, TX (US)

(73) Assignees: The Board of Regents of the University of Texas System, Austin, TX (US); The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 14/398,330

(22) PCT Filed: May 2, 2013

(86) PCT No.: PCT/US2013/039197
§ 371 (c)(1),
(2) Date: Oct. 31, 2014

(87) PCT Pub. No.: WO2013/166240
PCT Pub. Date: Nov. 7, 2013

(65) Prior Publication Data
US 2015/0087693 A1    Mar. 26, 2015

Related U.S. Application Data

(60) Provisional application No. 61/641,617, filed on May 2, 2012, provisional application No. 61/810,644, filed on Apr. 10, 2013.

(51) Int. Cl.
| | |
|---|---|
| C12N 15/113 | (2010.01) |
| A61K 31/7105 | (2006.01) |
| A61K 31/713 | (2006.01) |
| A61K 45/06 | (2006.01) |

(52) U.S. Cl.
CPC .......... *C12N 15/113* (2013.01); *A61K 31/713* (2013.01); *A61K 31/7105* (2013.01); *A61K 45/06* (2013.01); *C12N 2310/113* (2013.01); *C12N 2310/14* (2013.01); *C12N 2310/141* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 5,801,154 A * | 9/1998 | Baracchini | C07H 21/00 435/325 |
| 7,812,003 B2 * | 10/2010 | Safe | C12N 15/113 514/44 A |
| 2004/0220128 A1 * | 11/2004 | Pavco | C12N 15/113 514/44 A |
| 2008/0176766 A1 | 7/2008 | Brown et al. | |
| 2012/0180147 A1 * | 7/2012 | Thum | C07K 14/4702 800/8 |

OTHER PUBLICATIONS

Axton et al., "Aminopeptidase O contains a functional nucleolar localization signal and is implicated in vascular biology," *J. Cell. Biochem.* 103(4):1171-1182, 2008.
Bates et al., "MicroRNA regulation in Ames dwarf mouse liver may contribute to delayed aging," *Aging Cell*, 9:1-18, 2010.
Biyashev et al., "MiR-27b controls venous specification and tip cell fate," *Blood*, 119(11):2679-2687, 2012.
Chhabra et al., "Cooperative and individualistic functions of the microRNAs in the miR-23a~27a~24-2 cluster and its implication in human diseases," *Mol. Cancer* 9:232, 2010.
Fiedler et al., "MicroRNA-24 regulates vascularity after myocardial infarction," *Circulation*, 124:720-730, 2011.
Harris et al., "MicroRNA-126 regulates endothelial expression of vascular cell adhesion molecule 1," *Proc. Natl. Acad. Sci. USA*, 105:1516-1521, 2008.
Jennewein et al., "MicroRNA-27b contributes to lipopolysaccharide-mediated peroxisome proliferator-activated receptor gamma (PPARgamma) mRNA destabilization," *J. Biol. Chem.*, 285(16):11846-11853, 2010.
Kuehbacher et al., "Role of Dicer and Drosha for endothelial microRNA expression and angiogenesis," *Circ. Res.*, 101:59-68, 2007.
Lal et al., "miR-24 Inhibits cell proliferation by targeting E2F2, MYC, and other cell-cycle genes via binding to "seedless" 3'UTR microRNA recognition elements," *Mol. Cell*, 35(5):610-625, 2009.
Li et al., "Identification of miR-130a, miR-27b and miR-210 as serum biomarkers for antherosclerosis obliterans," *Clinica Chimica Acta*, 412(1-2):66-70, 2010.
Lin et al., "Effect of miR-23 on oxidant-induced injury in human retinal pigment epithelium cells," *Invest Ophthalmol Vis Sci.*, 52(9):6308-6314, 2011.
Ma et al., "miR-27a regulates the growth, colony formation and migration of pancreatic cancer cells by targeting Sprouty2," *Cancer Lett.*, 298(2):150-158, 2010.
Maegdefessel et al., "miR-24 limits aortic vascular inflammation and murine abdominal aneurysm development," *Nature Communications*, 5:5214, 2014.
Maragkakis et al., "DIANA-microT web server: elucidating microRNA functions through target prediction," *Nucleic Acids Res.*, 37(Web Server issue):W273-276, 2009.
Meloni et al., "Local inhibition of microRNA-24 improves reparative angiogenesis and left ventricle remodeling and function in mice with myocardial infarction," *Molecular Therapy*, 21(7):1390-1402, 2013.

(Continued)

*Primary Examiner* — Tracy Vivlemore
(74) *Attorney, Agent, or Firm* — Parker Highlander PLLC

(57) ABSTRACT

The present invention relates to the involvement of miR function in the development of age-related macular degeneration (AMD). It is shown that miR-23, miR-24 and/or miR-27 are involved in pathologic neovascularization in AMD, and that agonism (miR-24) and inhibition (miR23/27) of the function of these molecules blocks events contributing to development and progression of disease.

22 Claims, 29 Drawing Sheets

(56) References Cited

OTHER PUBLICATIONS

Mertens-Talcott et al., "The oncogenic microRNA-27a targets genes that regulate specificity protein transcription factors and the $G_2$-M checkpoint in MDA-MB-231 breast cancer cells," *Cancer Res*, 67(22):11001-11011, 2007.
PCT International Preliminary Report on Patentability issued in International Application No. PCT/US2013/039197, mailed Nov. 13, 2014.
PCT International Search Report and Written Opinion issued in International Application No. PCT/US2013/039197, mailed Aug. 23, 2013.
Poliseno et al., "MicroRNAs modulate the angiogenic properties of HUVECs," *Blood*, 108(9):3068-3071, 2006.
Qian et al., "miR-24 inhibits apoptosis and represses Bim in mouse cardiomyocytes," *J. Exp. Med.*, 208(3):549-560, 2011.
Qin et al., "miR-24 regulates apoptosis by targeting the open reading frame (ORF) region of FAF1 in cancer cells," *PLoS ONE*, 5(2):e9429, 2010.
Shen et al., "MicroRNAs regulate ocular neovascularization," *Mol. Ther.*, 16(7):1208-1216, 2008.
Suárez et al., "Dicer dependent microRNAs regulate gene expression and functions in human endothelial cells," *Circ. Res.*, 100(8):1164-1173, 2007.
Urbich et al., "MicroRNA-27 a/b controls endothelial cell repulsion and angiogenesis by targeting semaphorin 6A," *Blood*, 119(6):1607-1616, 2012.
Urbich et al., "Role of microRNAs in vascular diseases, inflammation, and angiogenesis," *Cardiovasc. Res.*, 79(4):581-588, 2008.
Walker & Harland, "microRNA-24a is required to repress apoptosis in the developing neural retina," *Genes Dev.*, 23(9):1046-1051, 2009.
Wang & Olson, "AngiomiRs—key regulators of angiogenesis," *Curr. Opin. Genet. Dev.*, 19(3):205-211, 2009.
Wang et al., "Control of endothelial cell proliferation and migration by VEGF signaling to histone deacetylase 7," *Proc. Natl. Acad. Sci. USA*, 105(22):7738-7743, 2008.
Wang et al., "MicroRNA-24 regulates cardiac fibrosis after myocardial infarction," *J Cell Mol Med.*, 16(9):2150-2160, 2012.
Wang et al., "miRNAs as potential therapeutic targets for age-related macular degeneration," *Future Med Chem.*, 4(3):277-287, 2012.
Zhang, "Novel functions for small RNA molecules," *Curr Opin Mol Ther.*, 11(6):641-651, 2009.
Zhou et al., "NF-kappaB p65-dependent transactivation of miRNA genes following *Cryptosporidium parvum* infection stimulates epithelial cell immune responses," *PLoS Pathog*, 5(12):e1000681, 2009.
Zhou et al., "Regulation of angiogenesis and choroidal neovascularization by members of microRNA-23~27~24 clusters," *PNAS*, 108(20):8287-8292, 2011.

\* cited by examiner

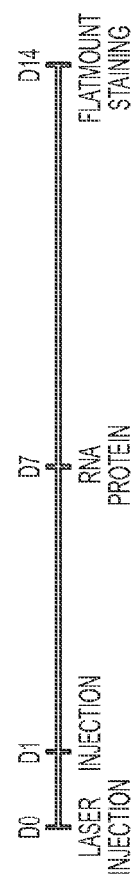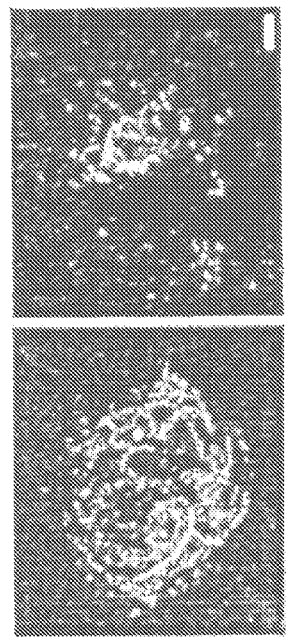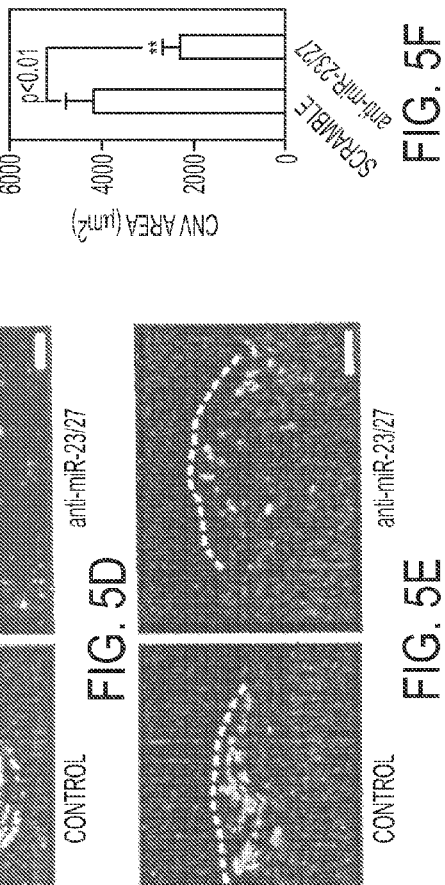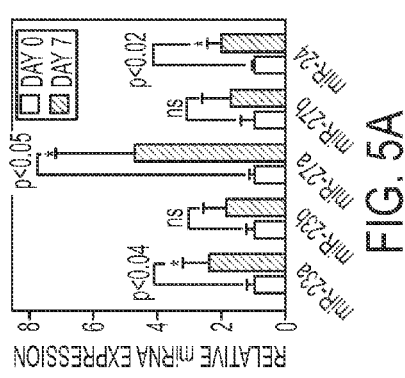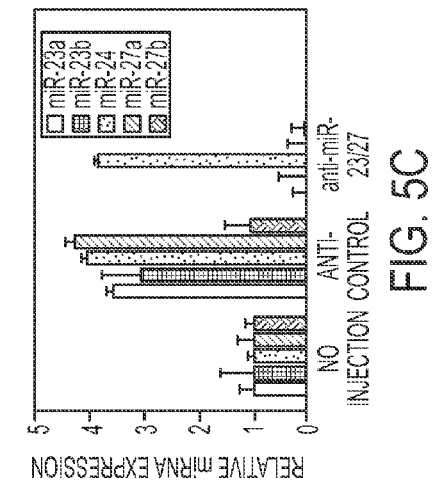
FIG. 5A FIG. 5B FIG. 5C FIG. 5D FIG. 5E FIG. 5F

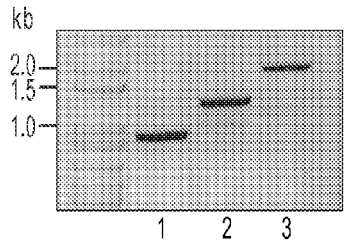

FIG. 7A

| | |
|---|---|
| miR-23a: | aucacauugccagggauuucc |
| Human | atcacattgccagggatttcc |
| Rhesus | atcacattgccagggatttcc |
| Mouse | atcacattgccagggatttcc |
| Dog | atcacattgccagggatttcc |
| Elephant | atcacattgccagggatttcc |
| Opossum | atcacattgccagggatttcc |
| X. tropicalis | atcacattgccagggatttcc |

| | |
|---|---|
| miR-23b: | aucacauugccagggauuacc |
| Human | atcacattgccagggattacc |
| Rhesus | atcacattgccagggattacc |
| Mouse | atcacattgccagggattacc |
| Dog | atcacattgccagggattacc |
| Elephant | atcacattgccagggattacc |
| Opossum | atcacattgccagggattacc |
| Chicken | atcacattgccagggattacc |
| X. tropicalis | atcacattgccagggattacc |
| Zebrafish | atcacattgccagggattacc |

| | |
|---|---|
| miR-27a: | uucacaguggcuaaguuccgc |
| Human | ttcacagtggctaagttccgc |
| Rhesus | ttcacagtggctaagttccgc |
| Mouse | ttcacagtggctaagttccgc |
| Dog | ttcacagtggctaagttccgc |
| Elephant | ttcacagtggctaagttccgc |
| Opossum | ttcacagtggctaagttccgc |
| X. tropicalis | ttcacagtggctaagttccgc |

| | |
|---|---|
| miR-27b: | uucacaguggcuaaguucugc |
| Human | ttcacagtggctaagttctgc |
| Rhesus | ttcacagtggctaagttctgc |
| Mouse | ttcacagtggctaagttctgc |
| Dog | ttcacagtggctaagttctgc |
| Elephant | ttcacagtggctaagttctgc |
| Opossum | ttcacagtggctaagttctgc |
| Chicken | ttcacagtggctaagttctgc |
| X. tropicalis | ttcacagtggctaagttctgc |
| Zebrafish | ttcacagtggctaagttctgc |

| | |
|---|---|
| miR-24-2: | uggcucaguucagcaggaacag |
| Human | tggctcagttcagcaggaacag |
| Rhesus | tggctcagttcagcaggaacag |
| Mouse | tggctcagttcagcaggaacag |
| Dog | tggctcagttcagcaggaacag |
| Elephant | tggctcagttcagcaggaacag |
| Opossum | tggctcagttcagcaggaacag |
| Chicken | tggctcagttcagcaggaacag |
| X. tropicalis | tggctcagttcagcaggaacag |
| Zebrafish | tggctcagttcagcaggaacag |

| | |
|---|---|
| miR-24-1: | uggcucaguucagcaggaacag |
| Rhesus | tggctcagttcagcaggaacag |
| Mouse | tggctcagttcagcaggaacag |
| Dog | tggctcagttcagcaggaacag |
| Elephant | tggctcagttcagcaggaacag |
| Opossum | tggctcagttcagcaggaacag |
| X. tropicalis | tggctcagttcagcagga-cag |

FIG. 7B

| PATHWAYS REGULATED BY miR-23 AND miR-27 PREDICTED BY DIANA LAB (DIANA-mirPATH) | | | | |
|---|---|---|---|---|
| | KEGG PATHWAY (RANK) | GENE NAMES | FOUND GENES | -lN(P-VALUE) (P-VALUE) |
| miR-23 OR miR-27 | AXON GUIDANCE (1) | EFNB2, SRGAP3, SEMA6A, NCK2, SLIT1, CXCL12, ITGB1, LIMK1, LIMK2, EFNA3, EPHB2, MET, SEMA6D, SRGAP2, KRAS, PAK3, FYN, CFL2, EPHA7, SEMA4C, UNC5D, CDC42, PAK2, PAK6, ROBO2, SEMA3B, SEMA4F | 27 | 12.39 (0.00018) |
| | MAPK SIGNALING PATHWAY (8) | MAP4K3, MAP4K4, PRKY, PDGFRA, EVI1, TGFBR1, MAP3K4, MAP3K1, MAPKAPK3, KRAS, CACNB2, MEF2C, MKNK2, DUSP5, STK4, MAP2K4, SOS1, DUSP16, PRKX, MAP3K3, RPS6KA5, FGF1, CDC25B, CDC42, GRB2, PAK2, MAP2K7, RAP1B, NLK, NF1, TGFBR2, MAPK14, MAP3K12, RPS6KA3, MAP3K5, MAPK10, SPROUTY2 | 37 | 4.78 (0.013) |
| miR-23 AND miR-27 | MAPK SIGNALING PATHWAY (1) | EVI1, CACNB2, MEF2C, DUSP5, SOS1, RPS6KA5, NLK, NF1, MAPK14, MAP3K12, SPROUTY2 | 11 | 14.54 ($4.2 \times 10^{-5}$) |
| | AXON GUIDANCE (5) | MET, SEMA6A, SEMA6D, FYN, PAK6 | 5 | 3.85 (0.07) |

FIG. 9

| GENE NAME | miRNA | POSITION | SITE | 3'UTR (SEQUENCE COMPLEMENTARY TO miRNA SEEDS HIGHLIGHTED IN RED) | CONSERVATION (SPECIES#) |
|---|---|---|---|---|---|
| DIAPH1 | miR-24 | 188-216 | 1; 7mer | 5'...CAGGGGAGGCCUGAGCC...3' | 5 |
| PAK4 | miR-24 | 448-476 | 1; 8mer | 5'...CCUCUCCCCCUGAGCCA...3' | 5 |
| LIMK2 | miR-24 | 1127-1155 | 1; 8mer | 5'...AGCAUCCUCCUGAGCCA...3' | 6 |

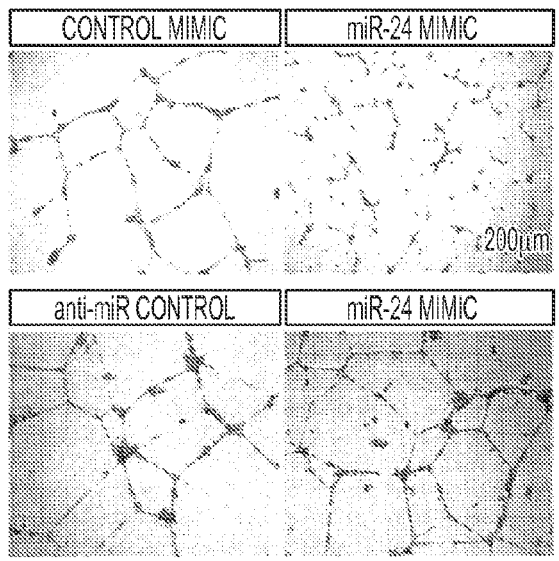
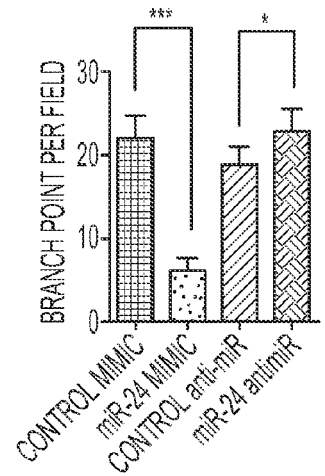
FIG. 14A                FIG. 14B
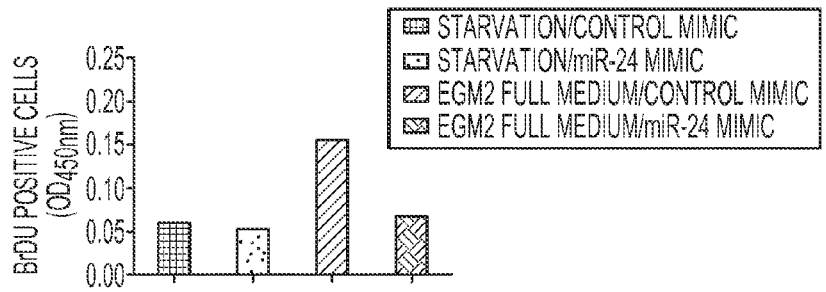
FIG. 14C
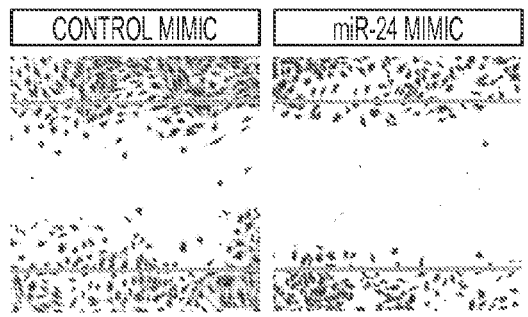
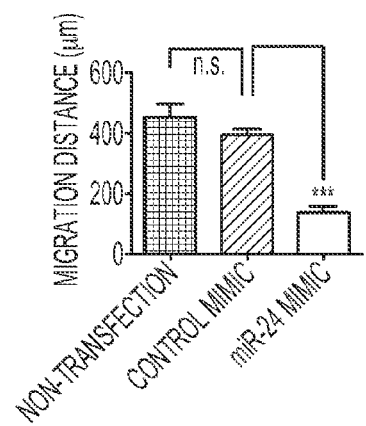
FIG. 14D

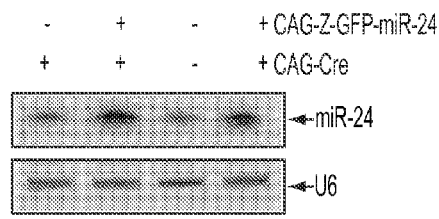
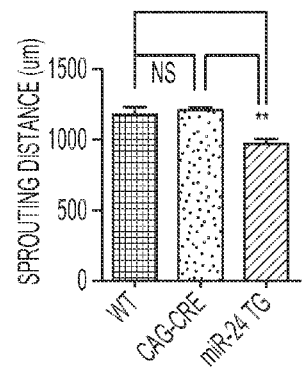
FIG. 20A
FIG. 20B
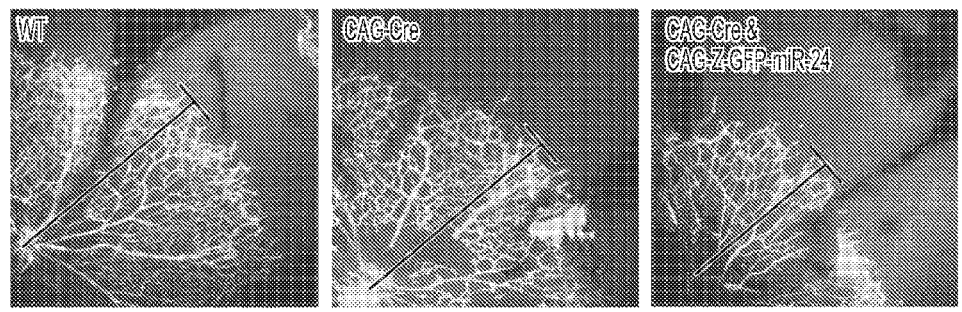
FIG. 20C
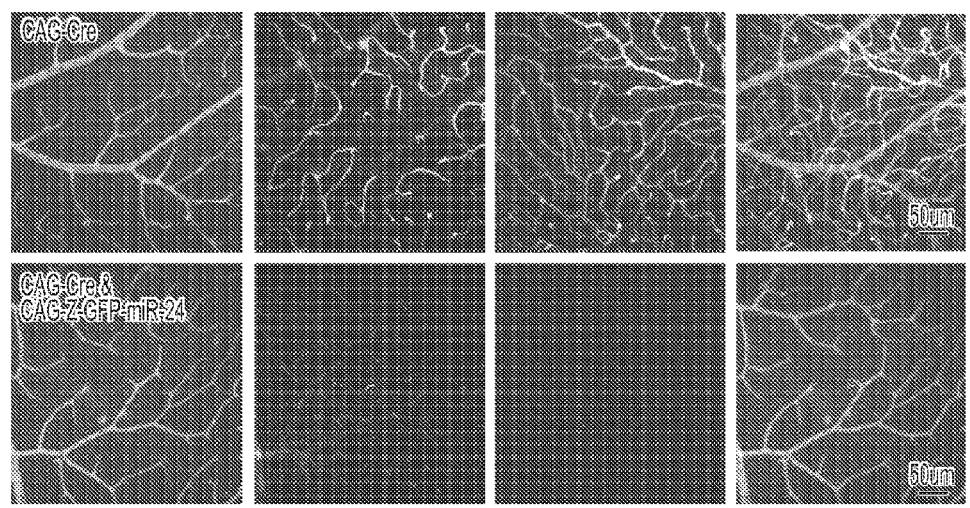
FIG. 20D

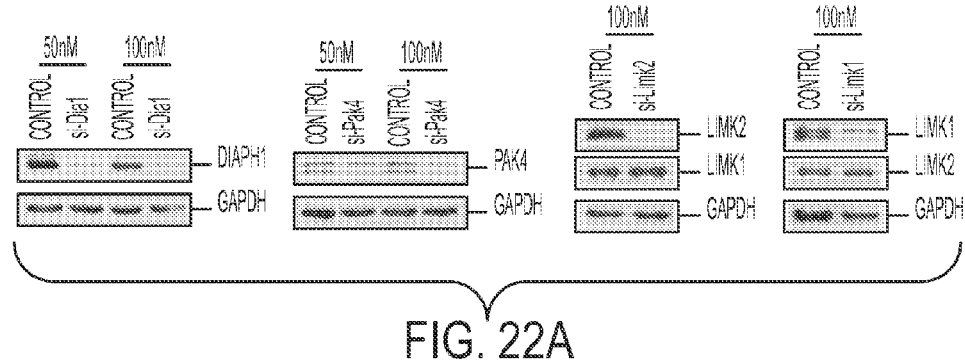
FIG. 22A
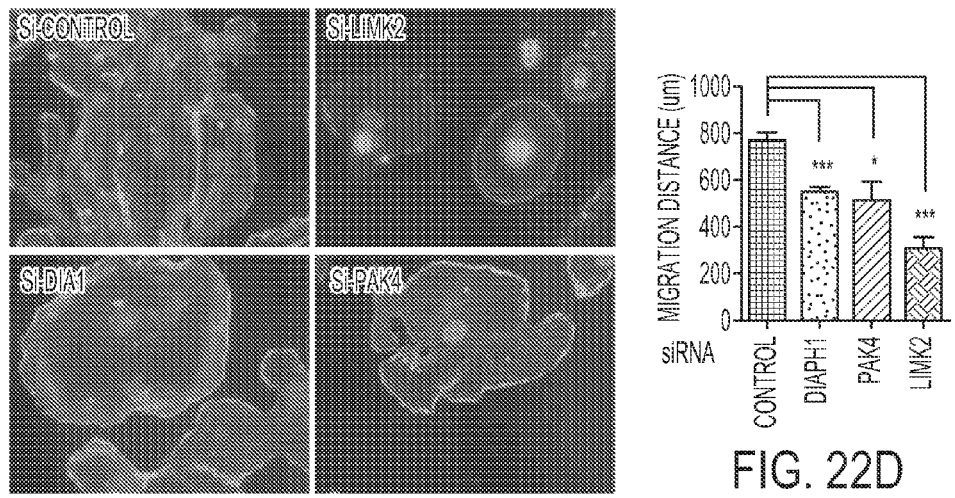
FIG. 22B
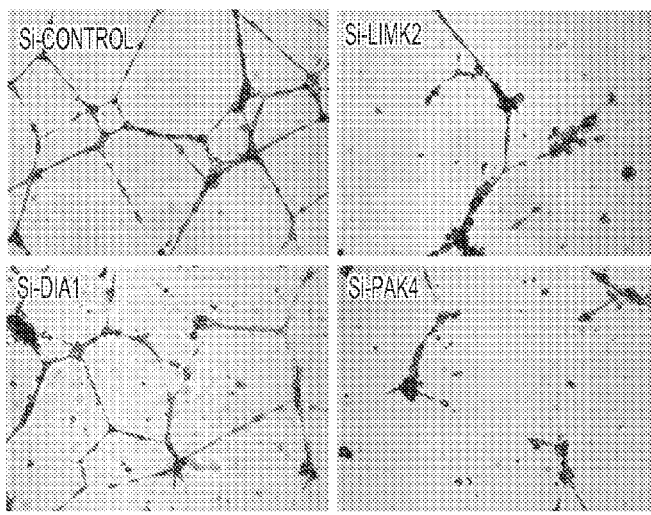
FIG. 22C
FIG. 22D
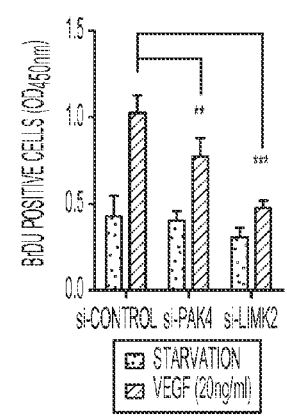
FIG. 22E

SEQUENCE LISTING

<160> NUMBER OF SEQ ID NOS: 48

<210> SEQ ID NO 1
<211> LENGTH: 21
<212> TYPE: RNA
<213> ORGANISM: Homo sapiens

<400> SEQUENCE: 1
aucacauugc cagggauuuc c                                         21

<210> SEQ ID NO 2
<211> LENGTH: 21
<212> TYPE: RNA
<213> ORGANISM: Homo sapiens

```
<400> SEQUENCE: 2
aucacauugc cagggauuac c                                              21

<210> SEQ ID NO 3
<211> LENGTH: 22
<212> TYPE: RNA
<213> ORGANISM: Homo sapiens

<400> SEQUENCE: 3
uggcucaguu cagcaggaac ag                                             22

<210> SEQ ID NO 4
<211> LENGTH: 22
<212> TYPE: RNA
<213> ORGANISM: Homo sapiens

<400> SEQUENCE: 4
uggcucaguu cagcaggaac ag                                             22

<210> SEQ ID NO 5
<211> LENGTH: 21
<212> TYPE: RNA
<213> ORGANISM: Homo sapiens

<400> SEQUENCE: 5
uucacagugg cuaaguuccg c                                              21

<210> SEQ ID NO 6
<211> LENGTH: 21
<212> TYPE: RNA
<213> ORGANISM: Homo sapiens

<400> SEQUENCE: 6
uucacagugg cuaaguucug c                                              21

<210> SEQ ID NO 7
<211> LENGTH: 33
<212> TYPE: DNA
<213> ORGANISM: Homo sapiens

<400> SEQUENCE: 7
atcggagctc agcaacacag acactcctag gca                                 33

<210> SEQ ID NO 8
<211> LENGTH: 35
<212> TYPE: DNA
<213> ORGANISM: Homo sapiens

<400> SEQUENCE: 8
atcgaagctt gcatctgtaa cccctcattt gcagc                               35

<210> SEQ ID NO 9
<211> LENGTH: 35
<212> TYPE: DNA
<213> ORGANISM: Homo sapiens

<400> SEQUENCE: 9
caataatatt tgcacagact ccaaacaagt tgtgc                               35

<210> SEQ ID NO 10
<211> LENGTH: 35
<212> TYPE: DNA
```

```
<213> ORGANISM: Homo sapiens

<400> SEQUENCE: 10
gcacaacttg tttggagtct gtgcaaatat tattg                              35

<210> SEQ ID NO 11
<211> LENGTH: 33
<212> TYPE: DNA
<213> ORGANISM: Homo sapiens

<400> SEQUENCE: 11
gtacattcgg aagccgacag atcaatcagt atg                                33

<210> SEQ ID NO 12
<211> LENGTH: 33
<212> TYPE: DNA
<213> ORGANISM: Homo sapiens

<400> SEQUENCE: 12
catactgatt gatctgtcgg cttccgaatg tac                                33

<210> SEQ ID NO 13
<211> LENGTH: 61
<212> TYPE: DNA
<213> ORGANISM: Homo sapiens

<400> SEQUENCE: 13
atcgaagctt gcatctgtaa cccctcattt gcagcaactc gagtcgcctc ataaaagggg   60
c                                                                   61

<210> SEQ ID NO 14
<211> LENGTH: 30
<212> TYPE: DNA
<213> ORGANISM: Homo sapiens

<400> SEQUENCE: 14
atcggagctc cccactgggg cgaaggtgga                                    30

<210> SEQ ID NO 15
<211> LENGTH: 32
<212> TYPE: DNA
<213> ORGANISM: Homo sapiens

<400> SEQUENCE: 15
atcgaagctt agggttgcgc atcatcagcc gt                                 32

<210> SEQ ID NO 16
<211> LENGTH: 24
<212> TYPE: DNA
<213> ORGANISM: Homo sapiens

<400> SEQUENCE: 16
ctggtgcatt cggaaacctt gtgt                                          24

<210> SEQ ID NO 17
<211> LENGTH: 24
<212> TYPE: DNA
<213> ORGANISM: Homo sapiens

<400> SEQUENCE: 17
attggagcat tcttgcttgc ctgc                                          24
```

```
<210> SEQ ID NO 18
<211> LENGTH: 24
<212> TYPE: DNA
<213> ORGANISM: Homo sapiens

<400> SEQUENCE: 18
atgaaagaga cgcactagcc caca                                          24

<210> SEQ ID NO 19
<211> LENGTH: 24
<212> TYPE: DNA
<213> ORGANISM: Homo sapiens

<400> SEQUENCE: 19
ttgggttcct ggcatgctga tttg                                          24

<210> SEQ ID NO 20
<211> LENGTH: 18
<212> TYPE: DNA
<213> ORGANISM: Homo sapiens

<400> SEQUENCE: 20
gaacttagcc actgtgaa                                                 18

<210> SEQ ID NO 21
<211> LENGTH: 18
<212> TYPE: DNA
<213> ORGANISM: Homo sapiens

<400> SEQUENCE: 21
aatccctggc aatgtgat                                                 18

<210> SEQ ID NO 22
<211> LENGTH: 22
<212> TYPE: DNA
<213> ORGANISM: Homo sapiens

<400> SEQUENCE: 22
gtgtaacacg tctatacgcc ca                                            22

<210> SEQ ID NO 23
<211> LENGTH: 15
<212> TYPE: DNA
<213> ORGANISM: Homo sapiens

<400> SEQUENCE: 23
acttagccac tgtga                                                    15

<210> SEQ ID NO 24
<211> LENGTH: 15
<212> TYPE: DNA
<213> ORGANISM: Homo sapiens

<400> SEQUENCE: 24
tccctggcaa tgtga                                                    15

<210> SEQ ID NO 25
<211> LENGTH: 15
<212> TYPE: DNA
<213> ORGANISM: Homo sapiens

<400> SEQUENCE: 25
acgtctatac gccca                                                    15
```

-continued

```
<210> SEQ ID NO 26
<211> LENGTH: 19
<212> TYPE: RNA
<213> ORGANISM: Homo sapiens

<400> SEQUENCE: 26
gcagguacau gucuugucu                                                  19

<210> SEQ ID NO 27
<211> LENGTH: 30
<212> TYPE: DNA
<213> ORGANISM: Homo sapiens

<400> SEQUENCE: 27
atcgctgcag cgcggtgaac tctctcttgt                                      30

<210> SEQ ID NO 28
<211> LENGTH: 28
<212> TYPE: DNA
<213> ORGANISM: Homo sapiens

<400> SEQUENCE: 28
atcgctgcag cccagctctc ctgagcct                                        28

<210> SEQ ID NO 29
<211> LENGTH: 24
<212> TYPE: DNA
<213> ORGANISM: Homo sapiens

<400> SEQUENCE: 29
atcggtcgac cgcggtgaac tctc                                            24

<210> SEQ ID NO 30
<211> LENGTH: 25
<212> TYPE: DNA
<213> ORGANISM: Homo sapiens

<400> SEQUENCE: 30
atcggtcgac cccagctctc ctgag                                           25

<210> SEQ ID NO 31
<211> LENGTH: 22
<212> TYPE: RNA
<213> ORGANISM: Homo sapiens

<400> SEQUENCE: 31 cguuccugc ugaacugagc ca                                               22

<210> SEQ ID NO 32
<211> LENGTH: 38
<212> TYPE: DNA
<213> ORGANISM: Homo sapiens
<220> FEATURE:
<221> NAME/KEY: misc_feature
<222> LOCATION: (1)..(1)
<223> OTHER INFORMATION: phosphate group
<220> FEATURE:
<221> NAME/KEY: misc_feature
<222> LOCATION: (2)..(2)
<223> OTHER INFORMATION: 2'-deoxy-2'-fluro nucleotides
<220> FEATURE:
<221> NAME/KEY: misc_feature
<222> LOCATION: (4)..(4)
<223> OTHER INFORMATION: phosphorothioate linkages
<220> FEATURE:
<221> NAME/KEY: misc_feature
```

<222> LOCATION: (5)..(5)
<223> OTHER INFORMATION: 2'-deoxy-2'-fluro nucleotides
<220> FEATURE:
<221> NAME/KEY: misc_feature
<222> LOCATION: (7)..(7)
<223> OTHER INFORMATION: 2'-deoxy-2'-fluro nucleotides
<220> FEATURE:
<221> NAME/KEY: misc_feature
<222> LOCATION: (9)..(9)
<223> OTHER INFORMATION: 2'-deoxy-2'-fluro nucleotides
<220> FEATURE:
<221> NAME/KEY: misc_feature
<222> LOCATION: (11)..(11)
<223> OTHER INFORMATION: 2'-deoxy-2'-fluro nucleotides
<220> FEATURE:
<221> NAME/KEY: misc_feature
<222> LOCATION: (13)..(13)
<223> OTHER INFORMATION: 2'-deoxy-2'-fluro nucleotides
<220> FEATURE:
<221> NAME/KEY: misc_feature
<222> LOCATION: (18)..(18)
<223> OTHER INFORMATION: 2'-deoxy-2'-fluro nucleotides
<220> FEATURE:
<221> NAME/KEY: misc_feature
<222> LOCATION: (21)..(21)
<223> OTHER INFORMATION: 2'-deoxy-2'-fluro nucleotides
<220> FEATURE:
<221> NAME/KEY: misc_feature
<222> LOCATION: (24)..(24)
<223> OTHER INFORMATION: 2'-deoxy-2'-fluro nucleotides
<220> FEATURE:
<221> NAME/KEY: misc_feature
<222> LOCATION: (26)..(26)
<223> OTHER INFORMATION: 2'-deoxy-2'-fluro nucleotides
<220> FEATURE:
<221> NAME/KEY: misc_feature
<222> LOCATION: (29)..(29)
<223> OTHER INFORMATION: 2'-deoxy-2'-fluro nucleotides
<220> FEATURE:
<221> NAME/KEY: misc_feature
<222> LOCATION: (31)..(31)
<223> OTHER INFORMATION: phosphorothioate linkages
<220> FEATURE:
<221> NAME/KEY: misc_feature
<222> LOCATION: (33)..(33)
<223> OTHER INFORMATION: 2'-deoxy-2'-fluro nucleotides
<220> FEATURE:
<221> NAME/KEY: misc_feature
<222> LOCATION: (35)..(35)
<223> OTHER INFORMATION: phosphorothioate linkages
<220> FEATURE:
<221> NAME/KEY: misc_feature
<222> LOCATION: (37)..(37)
<223> OTHER INFORMATION: phosphorothioate linkages

<400> SEQUENCE: 32
nnunnuncnu ncncgaancg nugnuncanc ngnuntnt                    38

<210> SEQ ID NO 33
<211> LENGTH: 33
<212> TYPE: DNA
<213> ORGANISM: Homo sapiens
<220> FEATURE:
<221> NAME/KEY: misc_feature
<222> LOCATION: (1)..(1)
<223> OTHER INFORMATION: cholesterol
<220> FEATURE:
<221> NAME/KEY: misc_feature
<222> LOCATION: (2)..(2)
<223> OTHER INFORMATION: phosphorothioate linkages
<220> FEATURE:
<221> NAME/KEY: misc_feature
<222> LOCATION: (4)..(4)
<223> OTHER INFORMATION: phosphorothioate linkages
<220> FEATURE:
<221> NAME/KEY: misc_feature
<222> LOCATION: (5)..(5)

```
<223> OTHER INFORMATION: 2'-deoxy-2'-fluro nucleotides
<220> FEATURE:
<221> NAME/KEY: misc_feature
<222> LOCATION: (8)..(8)
<223> OTHER INFORMATION: 2'-deoxy-2'-fluro nucleotides
<220> FEATURE:
<221> NAME/KEY: misc_feature
<222> LOCATION: (12)..(12)
<223> OTHER INFORMATION: 2'-deoxy-2'-fluro nucleotides
<220> FEATURE:
<221> NAME/KEY: misc_feature
<222> LOCATION: (15)..(15)
<223> OTHER INFORMATION: 2'-deoxy-2'-fluro nucleotides
<220> FEATURE:
<221> NAME/KEY: misc_feature
<222> LOCATION: (18)..(18)
<223> OTHER INFORMATION: 2'-deoxy-2'-fluro nucleotides
<220> FEATURE:
<221> NAME/KEY: misc_feature
<222> LOCATION: (20)..(20)
<223> OTHER INFORMATION: 2'-deoxy-2'-fluro nucleotides
<220> FEATURE:
<221> NAME/KEY: misc_feature
<222> LOCATION: (22)..(22)
<223> OTHER INFORMATION: 2'-deoxy-2'-fluro nucleotides
<220> FEATURE:
<221> NAME/KEY: misc_feature
<222> LOCATION: (30)..(30)
<223> OTHER INFORMATION: phosphorothioate linkages
<220> FEATURE:
<221> NAME/KEY: misc_feature
<222> LOCATION: (32)..(32)
<223> OTHER INFORMATION: phosphorothioate linkages

<400> SEQUENCE: 33
nnasncgnug ancancgnun uncggagaan tnt                                   33

<210> SEQ ID NO 34
<211> LENGTH: 35
<212> TYPE: RNA
<213> ORGANISM: Homo sapiens
<220> FEATURE:
<221> NAME/KEY: misc_feature
<222> LOCATION: (1)..(1)
<223> OTHER INFORMATION: phosphate group
<220> FEATURE:
<221> NAME/KEY: misc_feature
<222> LOCATION: (2)..(2)
<223> OTHER INFORMATION: 2'-deoxy-2'-fluro nucleotides
<220> FEATURE:
<221> NAME/KEY: misc_feature
<222> LOCATION: (4)..(4)
<223> OTHER INFORMATION: phosphorothioate linkages
<220> FEATURE:
<221> NAME/KEY: misc_feature
<222> LOCATION: (7)..(7)
<223> OTHER INFORMATION: 2'-deoxy-2'-fluro nucleotides
<220> FEATURE:
<221> NAME/KEY: misc_feature
<222> LOCATION: (9)..(9)
<223> OTHER INFORMATION: 2'-deoxy-2'-fluro nucleotides
<220> FEATURE:
<221> NAME/KEY: misc_feature
<222> LOCATION: (11)..(11)
<223> OTHER INFORMATION: 2'-deoxy-2'-fluro nucleotides
<220> FEATURE:
<221> NAME/KEY: misc_feature
<222> LOCATION: (15)..(15)
<223> OTHER INFORMATION: 2'-deoxy-2'-fluro nucleotides
<220> FEATURE:
<221> NAME/KEY: misc_feature
<222> LOCATION: (17)..(17)
<223> OTHER INFORMATION: 2'-deoxy-2'-fluro nucleotides
<220> FEATURE:
<221> NAME/KEY: misc_feature
<222> LOCATION: (19)..(19)
<223> OTHER INFORMATION: 2'-deoxy-2'-fluro nucleotides
```

-continued

```
<220> FEATURE:
<221> NAME/KEY: misc_feature
<222> LOCATION: (23)..(23)
<223> OTHER INFORMATION: 2'-deoxy-2'-fluro nucleotides
<220> FEATURE:
<221> NAME/KEY: misc_feature
<222> LOCATION: (30)..(30)
<223> OTHER INFORMATION: 2'-deoxy-2'-fluro nucleotides
<220> FEATURE:
<221> NAME/KEY: misc_feature
<222> LOCATION: (32)..(32)
<223> OTHER INFORMATION: phosphorothioate linkages
<220> FEATURE:
<221> NAME/KEY: misc_feature
<222> LOCATION: (34)..(34)
<223> OTHER INFORMATION: phosphorothioate linkages

<400> SEQUENCE: 34
nnunggncnu ncagnununc agncaggaan cnang                                35

<210> SEQ ID NO 35
<211> LENGTH: 40
<212> TYPE: RNA
<213> ORGANISM: Homo sapiens
<220> FEATURE:
<221> NAME/KEY: misc_feature
<222> LOCATION: (1)..(1)
<223> OTHER INFORMATION: cholesterol
<220> FEATURE:
<221> NAME/KEY: misc_feature
<222> LOCATION: (2)..(2)
<223> OTHER INFORMATION: phosphorothioate linkages
<220> FEATURE:
<221> NAME/KEY: misc_feature
<222> LOCATION: (4)..(4)
<223> OTHER INFORMATION: phosphorothioate linkages
<220> FEATURE:
<221> NAME/KEY: misc_feature
<222> LOCATION: (5)..(5)
<223> OTHER INFORMATION: 2'-deoxy-2'-fluro nucleotides
<220> FEATURE:
<221> NAME/KEY: misc_feature
<222> LOCATION: (7)..(7)
<223> OTHER INFORMATION: 2'-deoxy-2'-fluro nucleotides
<220> FEATURE:
<221> NAME/KEY: misc_feature
<222> LOCATION: (9)..(9)
<223> OTHER INFORMATION: 2'-deoxy-2'-fluro nucleotides
<220> FEATURE:
<221> NAME/KEY: misc_feature
<222> LOCATION: (11)..(11)
<223> OTHER INFORMATION: 2'-deoxy-2'-fluro nucleotides
<220> FEATURE:
<221> NAME/KEY: misc_feature
<222> LOCATION: (13)..(13)
<223> OTHER INFORMATION: 2'-deoxy-2'-fluro nucleotides
<220> FEATURE:
<221> NAME/KEY: misc_feature
<222> LOCATION: (16)..(16)
<223> OTHER INFORMATION: 2'-deoxy-2'-fluro nucleotides
<220> FEATURE:
<221> NAME/KEY: misc_feature
<222> LOCATION: (18)..(18)
<223> OTHER INFORMATION: 2'-deoxy-2'-fluro nucleotides
<220> FEATURE:
<221> NAME/KEY: misc_feature
<222> LOCATION: (23)..(23)
<223> OTHER INFORMATION: 2'-deoxy-2'-fluro nucleotides
<220> FEATURE:
<221> NAME/KEY: misc_feature
<222> LOCATION: (25)..(25)
<223> OTHER INFORMATION: 2'-deoxy-2'-fluro nucleotides
<220> FEATURE:
<221> NAME/KEY: misc_feature
<222> LOCATION: (30)..(30)
<223> OTHER INFORMATION: 2'-deoxy-2'-fluro nucleotides
<220> FEATURE:
```

```
<221> NAME/KEY: misc_feature
<222> LOCATION: (32)..(32)
<223> OTHER INFORMATION: 2'-deoxy-2'-fluro nucleotides
<220> FEATURE:
<221> NAME/KEY: misc_feature
<222> LOCATION: (35)..(35)
<223> OTHER INFORMATION: phosphorothioate linkages
<220> FEATURE:
<221> NAME/KEY: misc_feature
<222> LOCATION: (36)..(36)
<223> OTHER INFORMATION: 2'-deoxy-2'-fluro nucleotides
<220> FEATURE:
<221> NAME/KEY: misc_feature
<222> LOCATION: (38)..(38)
<223> OTHER INFORMATION: phosphorothioate linkages
<220> FEATURE:
<221> NAME/KEY: misc_feature
<222> LOCATION: (39)..(39)
<223> OTHER INFORMATION: 2'-deoxy-2'-fluro nucleotides

<400> SEQUENCE: 35
nngnnununc ncnugncnug aancnugagn cncannunnu                            40

<210> SEQ ID NO 36
<211> LENGTH: 21
<212> TYPE: DNA
<213> ORGANISM: Homo sapiens

<400> SEQUENCE: 36
cucugagucc cuccgcguat t                                                21

<210> SEQ ID NO 37
<211> LENGTH: 21
<212> TYPE: DNA
<213> ORGANISM: Homo sapiens

<400> SEQUENCE: 37
gcuucuuugg gcaggcuaut t                                                21

<210> SEQ ID NO 38
<211> LENGTH: 21
<212> TYPE: DNA
<213> ORGANISM: Homo sapiens

<400> SEQUENCE: 38
ggcugaagcu gucagacuut t                                                21

<210> SEQ ID NO 39
<211> LENGTH: 21
<212> TYPE: DNA
<213> ORGANISM: Homo sapiens

<400> SEQUENCE: 39
caugugagga guuacguaat t                                                21

<210> SEQ ID NO 40
<211> LENGTH: 21
<212> TYPE: DNA
<213> ORGANISM: Homo sapiens

<400> SEQUENCE: 40
ccucuaugau gcaaccuaut t                                                21

<210> SEQ ID NO 41
<211> LENGTH: 30
<212> TYPE: DNA
<213> ORGANISM: Homo sapiens
```

```
<400> SEQUENCE: 41
atcggccggc aggaggcaag tgggcgcagc                                    30

<210> SEQ ID NO 42
<211> LENGTH: 32
<212> TYPE: DNA
<213> ORGANISM: Homo sapiens

<400> SEQUENCE: 42
atcggtttaa acggcccagt tcaggcccac ca                                 32

<210> SEQ ID NO 43
<211> LENGTH: 33
<212> TYPE: DNA
<213> ORGANISM: Homo sapiens

<400> SEQUENCE: 43
atcggagctc ctggggtag atgagaccct act                                 33

<210> SEQ ID NO 44
<211> LENGTH: 31
<212> TYPE: DNA
<213> ORGANISM: Homo sapiens

<400> SEQUENCE: 44
atcgaagctt ctggttcttc aggcagtggt t                                  31

<210> SEQ ID NO 45
<211> LENGTH: 30
<212> TYPE: DNA
<213> ORGANISM: Homo sapiens

<400> SEQUENCE: 45
atcgactagt gtgaccgcgg cagctcctca                                    30

<210> SEQ ID NO 46
<211> LENGTH: 33
<212> TYPE: DNA
<213> ORGANISM: Homo sapiens

<400> SEQUENCE: 46
atcggtttaa actgggccaa gcccaagagt gcc                                33

<210> SEQ ID NO 47
<211> LENGTH: 32
<212> TYPE: DNA
<213> ORGANISM: Homo sapiens

<400> SEQUENCE: 47
atcggagctc ttccccttct ctctgaaaca gc                                 32

<210> SEQ ID NO 48
<211> LENGTH: 37
<212> TYPE: DNA
<213> ORGANISM: Homo sapiens

<400> SEQUENCE: 48
atcgaagctt caacaagttc aagtattctt tattcaa                            37
```

MICRO-RNAS INVOLVED IN MACULAR DEGENERATION

The present application is a national phase application under 35 U.S.C. 371 of International Application No. PCT/US2013/039197, filed May 2, 2013, which claims benefit of priority to U.S. Provisional Application Ser. No. 61/641,617, filed May 2, 2012, and to U.S. Provisional Application Ser. No. 61/810,644, filed Apr. 10, 2013, the entire contents of each of the applications being hereby incorporated by reference.

BACKGROUND OF THE INVENTION

1. Field of the Invention

The present invention relates generally to the fields of medicine, pathology and molecular biology. More particularly, it concerns the involvement of miR function in the development of pathologic angiogenesis. Specifically, the invention relates to the antagonism of miR-23 and/or miR-27, and the agonism of miR-24, for treating AMD.

2. Description of Related Art

The growth of blood vessels through angiogenesis is a delicately controlled process which involves endothelial cell (EC) activation, proliferation, migration and maturation (Distler et al., 2003). Physiological angiogenesis is required for normal vascular development, as well as vascular homeostasis during adulthood. Pathological angiogenesis, commonly induced by tissue ischemia or inflammation, underlies numerous vascular disorders, such as age-related macular degeneration (AMD), a leading cause of blindness in the elderly Friedman (2004). Choroidal neovascularization (CNV), which involves abnormal growth of blood vessels in the back of the eye, is a hallmark of neovascular AMD (Jager et al. 2008). Although the pathogenic mechanisms underlying AMD are still largely unknown, vascular endothelial growth factor (VEGF) has been shown to play a causal role in the development of CNV (Grisanti & Tatar, 2008). Anti-VEGF agents have demonstrated efficacy in treating CNV in neovascular AMD (Brown et al., 2006; Rosenfeld et al., 2006), but have limited efficacy and potential side effects (Amrite et al., 2010; Zachary et al., 2005).

Recent studies have revealed important roles for micro-RNAs (miRNAs) in cardiovascular diseases and other disorders (Small & Olsen, 2011). miRNAs are small noncoding RNAs that negatively regulate gene expression by inducing mRNA degradation or inhibiting translation through binding to the 3' untranslated region (3'UTR) of target mRNAs (Bartel, 2004). Often, miRNAs modulate broad collections of mRNAs encoding multiple components of complex biological pathways. Several miRNAs have been implicated in angiogenesis (Wang & Olsen, 2009; Urbich et al., 2008). A group of miRNAs has also been shown to be substantially decreased in a laser-induced CNV model (Shen et al., 2008). The significance of these miRNAs in AMD, however, remains to be formally established.

SUMMARY OF THE INVENTION

Thus, in accordance with the present invention, there is provided a method of treating age-related wet macular degeneration (AMD) comprising administering to a subject antagonists of miR-23 function and/or miR-27 function, and agonism of miR-24 function. The method may further comprise administering antagonists for each of miR-23 function and miR-27 function, and an agonist of miR-24 function. The particular combinations include antagonists of miR-23 function and miR-27 function, an antagonist of miR-23 function and an agonist of miR-24 function, or an agonist of miR-24 function and an antagonist of miR-27 function are administered. The subject may be a non-human animal or a human. The antagonists may be miR antagomirs or antisense molecules, and the agonists may be mimics or the miR-24 molecule itself. The agonists/antagonists may be formulated in a lipid delivery vehicle. The miR, mimics, antagomirs or antisense molecules may contain at least one non-natural base.

The antagonist may be delivered to the eye, to the ocular vasculature or sytemtically. The method may further comprise administering to said subject a secondary anti-AMD therapy. The secondary anti-AMD therapy may be bevacizumab, ranibizumab, pegaptanib, or aflibercept. The secondary anti-AMD therapy may be given prior to or after said antagonists, or given at the same time as said antagonists. Treating may comprise slowing the progression of disease, or improving the vision of said subject. The antagonist may be administered multiple times, such as administered daily, every other day, every third day, every fourth day, every fifth day, every sixth day, weekly or monthly. The antagonist may be administered continuously over a time period exceeding 24 hours.

In another embodiment, there is provided a method of treating a pathologic neovascular disease state or condition comprising administering to a subject antagonists of miR-23 function and/or miR-27 function, and agonism of miR-24 function. The method may further comprise administering antagonists for both of miR-23 function and miR-27 function, and agonist of miR-24 function. The particular combinations include antagonists of miR-23 function and miR-27 function, an antagonist of miR-23 function and an agonist of miR-24 function, or an agonist of miR-24 function and an antagonist of miR-27 function are administered. The subject may be a non-human animal or a human. The antagonists may be miR antagomirs or antisense moleculess, and the agonists may be mimics or the miR-24 molecule itself. The agonists/antagonists may be formulated in a lipid delivery vehicle. The miR, mimics, antagomirs or antisense molecules may contain at least one non-natural base. The method may further comprise administering to said subject a secondary therapy for cancer, atherosclerosis, coronary artery disease, diabetic retinopathy, or retinopathy of prematurity.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

(FIG. 1A) Structure of mouse miR-23~27~24 clusters. Chromosome locations of miR-23a~27a~24-2 and miR-23b~27b~24-1 are shown. Pre-miR23a/b, pre-miR-27a/b and pre-miR-24 are shown as striped boxes. The exons of miR-23b~27b~24-1 host gene are indicated as black boxes labeled 1, 2 and 3. (FIG. 1B) Expression of miR-23~27~24 cluster members in different tissues as detected by Northern blot using Starfire™ miRNA probes. U6 served as a loading control. (FIG. 1C) Expression of miR-23~27~24 cluster members in different cell types relative to that in HUVECs, as detected using LNA-modified miRNA PCR primers (Exiqon). HUVEC: human umbilical vein endothelial cell (EC) line; C2C12: mouse myoblast cell line; CM: mouse cardiomyocyte; SMC: mouse smooth muscle cell line; 3T3-L1: mouse adipocyte progenitor cell line; THP1: human monocyte cell line; CFB: rat cardiac fibroblast.

(FIG. 2A) Specific silencing of miR-23 and miR-27 in HUVECs by LNA-modified anti-miR shown by real-time PCR with LNA-modified miRNA primers. (FIG. 2B) Representative pictures of in vitro Matrigel assays after silencing of miR-23 or miR-27 in HUVECs. (FIG. 2C) Quantification of branching points in the in vitro Matrigel assays. Six independent samples were quantified in each group. P values are shown. (FIG. 2D) Quantification of ex vivo aortic ring assays 5 days after miR-23/27 knockdown or overexpression by adenovirus. Sprouting distance was measured from the average number of 6 aortic rings in each group. P values are indicated. ns, not significant. (FIG. 2E) Quantification of VEGF-induced HUVEC proliferation indicated by BrDU incorporation after miR-23 and/or miR-27 LNA-anti-miR transfection. P values are indicated. ns, not significant. (FIG. 2F) Quantification of VEGF-induced HUVEC migration distance ($\mu$m) in scratch wound assay after miR-23 or miR-27 LNA-anti-miR transfection. P values are indicated. ns, not significant.

(FIG. 3A) miRs-23/27 target the SPROUTY2, SEMA6A and SEMA6D 3' UTRs as shown by luciferase assays. SPROUTY2 (miR-23m) and SPROUTY2 (miR-27m) indicate SPROUTY2 UTR with mutations in miR-23 and miR-27 targeting sites, respectively. Pre-miR™ miRNA precursors (ABI) used in the transfections are indicated. The P values are shown. (FIG. 3B) Regulation of miRs-23/27 target proteins SPROUTY2, SEMA6A and SEMA6D by miR-23 and miR-27, as detected by Western blot. LNA-anti-miR transfection or adenovirus infection was performed as indicated. (FIG. 3C) Repression of ERK1/2 and AKT phosphorylation by miRs-23/27 knockdown in HUVECs as shown by Western blot analyses. GAPDH served as a loading control. (FIG. 3D) Repression of ERK1/2 phosphorylation in response to VEGF by miRs-23/27 knockdown as shown by Western blot. LNA-anti-miR transfection and the time points of VEGF treatment are shown as indicated. (FIG. 3E). Repression of VEGFR2 and ERK1/2 phosphorylation in response to VEGF by recombinant SEMA6A protein as detected by Western blot. GAPDH served as a loading control. (FIG. 3F). Knockdown of Sprouty2 by siRNA in cultured aortas shown by Western blot. GAPDH served as a loading control. (FIG. 3G). Quantification of ex vivo aortic ring assays 6 days after miR-23/27 anti-miR and/or Sprouty2 siRNA transfection. Six independent aortic rings were quantified in each group. P values are indicated.

(FIG. 4A) Experimental setup for retinal injections. LNA-anti-miRs were injected at P2 and retinal samples are collected at P6 for RNA, protein analyses and flatmount staining. (FIG. 4B) Expression of miR-23~27~24 family members in the retina after LNA anti-miR treatment by real-time PCR with LNA-modified miRNA primers. (FIG. 4C) Vasculature of the retina at P6 after LNA anti-miR treatment at P2, as visualized by ICAM-2 and GFAP staining in flat mount preparation. Upper panel: anti-scramble; lower panel: anti-miR-23/27. Scale bar (left panel):100 $\mu$m. Scale bar (middle and right panel): 50 $\mu$m. Arrows points to the new retinal vascular sprouts. (FIG. 4D) Quantification of sprouting distance ($\mu$m) and vascular coverage of the retinal vasculature from 12 miR-23/27 anti-miR treated retinas compared to 12 scramble controls. P values are indicated. (FIG. 4E) Western blot analyses showing the upregulation of miRs-23/27 target proteins Sprouty2, Sema6A and Sema6D upon miRs-23/27 knockdown in P6 retinas.

FIGS. 5A-F. Repression of laser-induced CNV by LNA-anti-miR-23/27. (FIG. 5A) Up-regulation miR-23~27~24 cluster members 7 days after laser injury in the eye as shown by real-time PCR using LNA-miRNA primers. P values are indicated. (FIG. 5B) Experimental setup for laser injury and retinal injections. Time points of laser injury, anti-miR injection and sample isolation are denoted below the line. (FIG. 5C) Silencing of miR-23 and miR-27 in the retina/choroid/sclera by LNA-anti-miR injection shown by real-time PCR with LNA-miRNA primers. (FIG. 5D) Representative confocal images of ICAM-2 staining showing repression of CNV by LNA-anti-miR-23/27 compared to a scramble control. Scale bar equals 50 $\mu$m. (FIG. 5E) ICAM-2 immunostaining of CNV lesion sections showing reduced neovascularization by LNA-anti-miR-23/27. Dash lines: borders the CNV lesion. Scale bar equals 50 $\mu$m. (FIG. 5F) Quantification of CNV area ($\mu m^2$). P value is from the measurements of 36 control-injected retinas and 32 LNA-anti-miR-23/27 injected retinas.

Loss of miR-23/27 function diminishes MAP kinase and VEGFR2 signaling in response to VEGF, and therefore represses angiogenesis.

FIGS. 7A-D. miR-23~27~24 cluster analysis. (FIG. 7A) Expression of pri-miRNA of mouse miR-23~27~24 clusters as examined by RT-PCR using Race Ready cDNA from mouse embryos (Ambion). Lane 1 is the PCR product using primer A and B shown in FIG. 1A. Lane 2 is the PCR product using Primer C and D, and lane 3 is the PCR product using Primer C and E shown in FIG. 1A. (FIG. 7B) Evolution conservation of miR-23~27~24 clusters in vertebrate species using Human Blat. (genome.ucsc.edu/cgi-bin/hgBlat?command=start). The seed regions are highlighted. (FIGS. 7C-D) Expression of miR-23~27~24 cluster members in different tissues as detected by real-time PCR using LNA-modified miRNA probes. U6 served as a normalization control.

Figure 8:
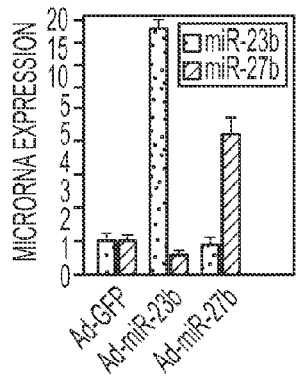

FIG. 8. Efficient over-expression of miR-23 or miR-27. Measurements in the cultured aortic rings by adenovirus expressing miR-23b or miR-27b, as shown by real-time PCR with LNA-modified miRNA primes.

FIG. 9. miRs in angiogenesis. Pathways and genes regulated by miR-23 or miR-27 (top) or miR-23 and miR-27 (bottom) predicted using Diana-mirPath from Dianal.ab.

Figure 10:
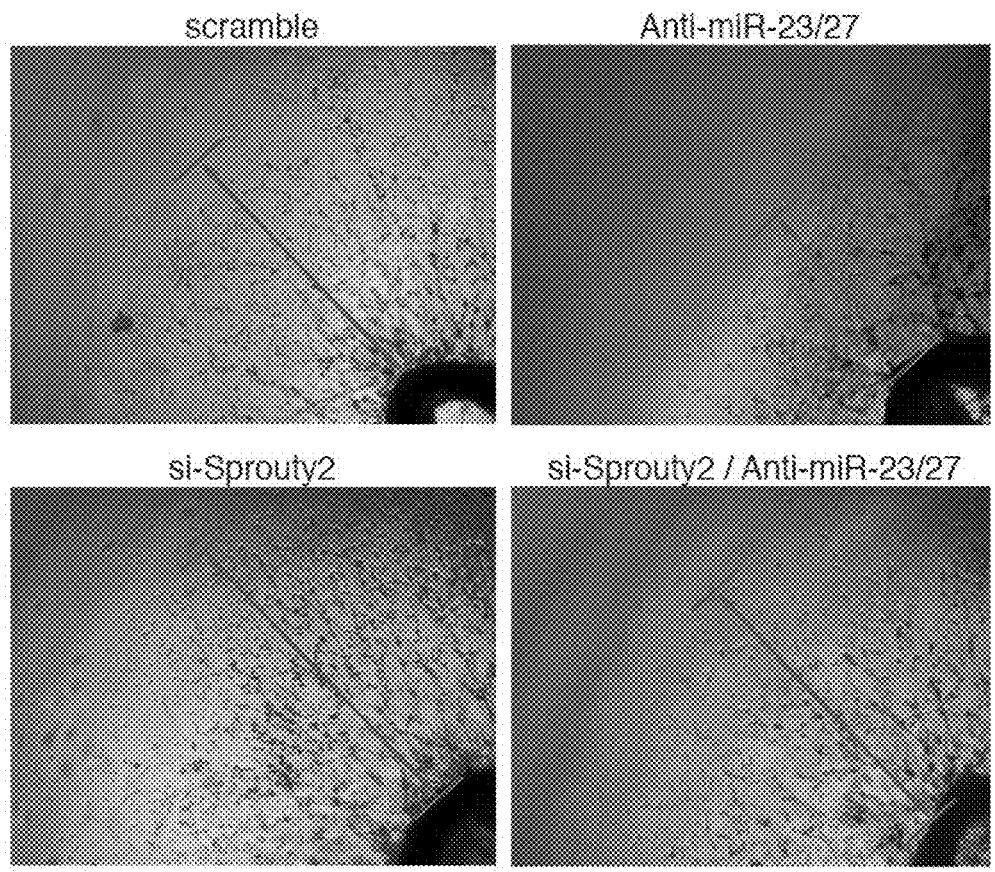

FIG. 10. Representative pictures of ex vivo aortic ring assays 6 days after anti-miR-23/27 and/or Sprouty2 siRNA transfection in cultured aortic rings. Sprouting of the aortic ring cells are indicated by the grey lines.

Figure 11A:
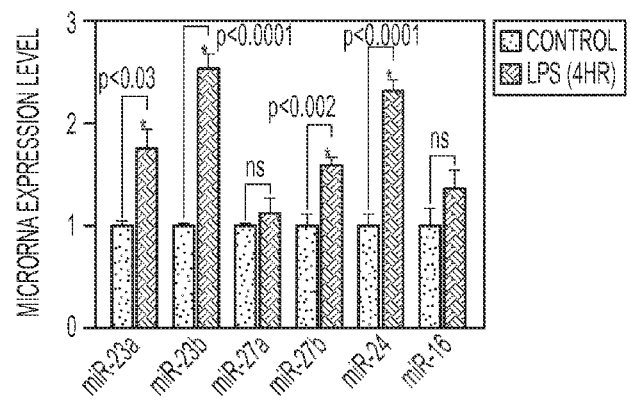
Figure 11B:
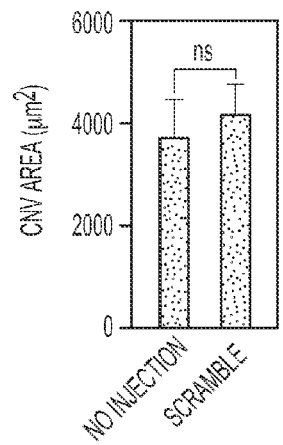

FIGS. 11A-B. Expression of miRs cluster members and quantification in CNV. (FIG. 11A) Expression of miR-23~27~24 cluster members in HUVECs induced by LPS, as detected using LNA-modified miRNA PCR primers. U6 served as a normalization control. (FIG. 11B) Quantification of CNV area from ICAM-2 staining of the choroid 1 flatmounts measured from control-injected retinas and no-injection control retinas 14 days after laser injury. ns, not significant.

Figures 12A, 12B, 12C:
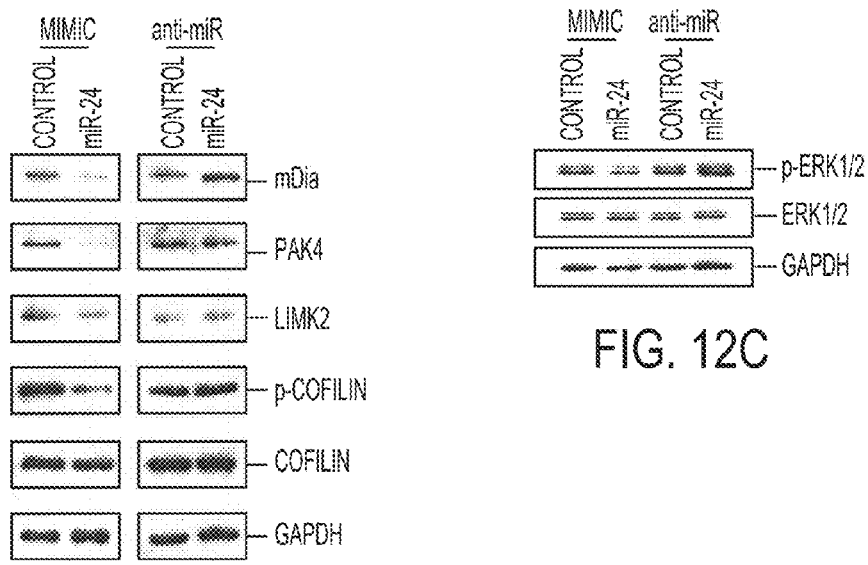

FIGS. 12A-C. Regulation of miR-24 target proteins by miR-24 mimic and anti-miR in ECs. (FIG. 12A) A table showing several miR-24 target genes involved in cytoskeleton actin dynamics predicted by DIANA-mirPath software. The sequences in the target genes complementary to the miRNA seed regions are shown in bold type. The number of species in which the target sites are conserved is shown; (FIG. 12B) Regulation of miR-24 target proteins mDia (Diaph1), Pak4 and Limk2, as well as the phosphorylation of their downstream protein Cofilin by miR-24 in HUVECs, as shown by Western blot analyses. GAPDH served as a loading control; (FIG. 12C). Regulation of ERK1/2 phosphorylation by miR-24 in HUVECs, as revealed by Western blot. GAPDH served as a loading control.

Figure 13A:
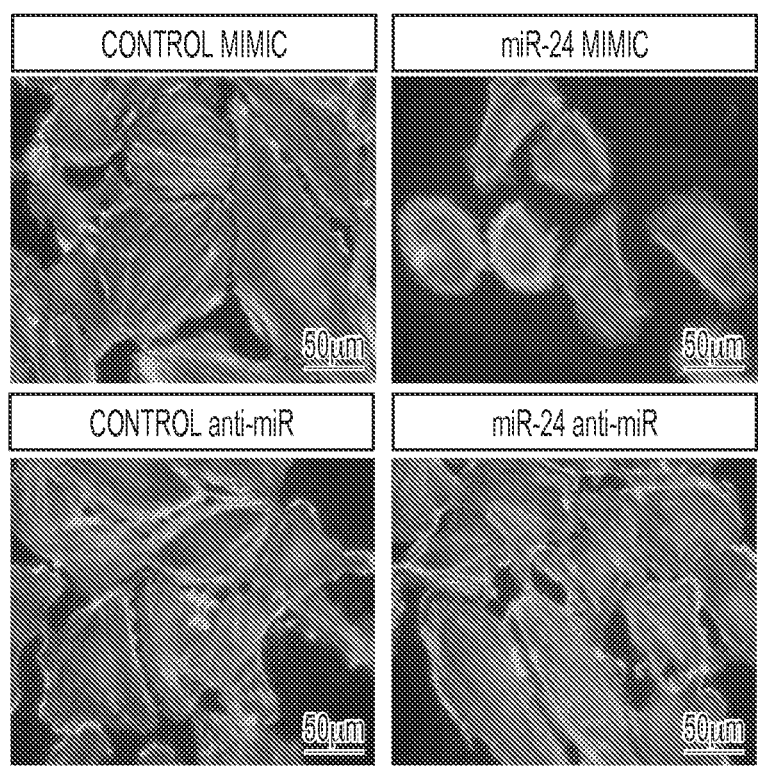
Figure 13B:
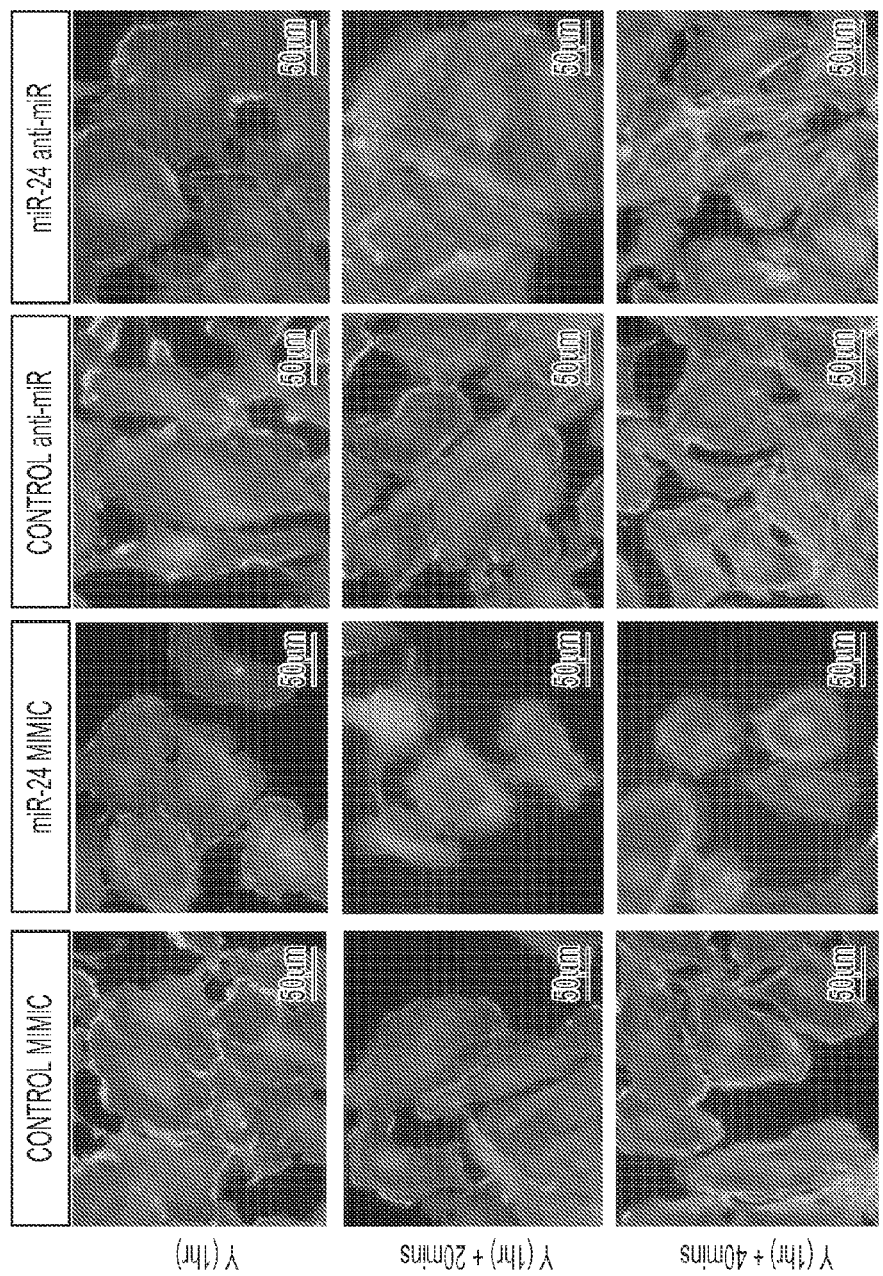

FIGS. 13A-B. Regulation of EC shape and actin dynamics by miR-24. (FIG. 13A). Loss of stress fiber and shape changes in ECs transfected with miR-24 mimic, as revealed by phalloidin staining. Scale=50 µm; (FIG. 13B). Stress fiber formation in miR-24 mimic or anti-miR transfected ECs after 1 hr Rho inhibitor Y-27632 treatment and at 20 and 40 min after the remover of Y-27632. Scale=50 µm.

Figure 14E:
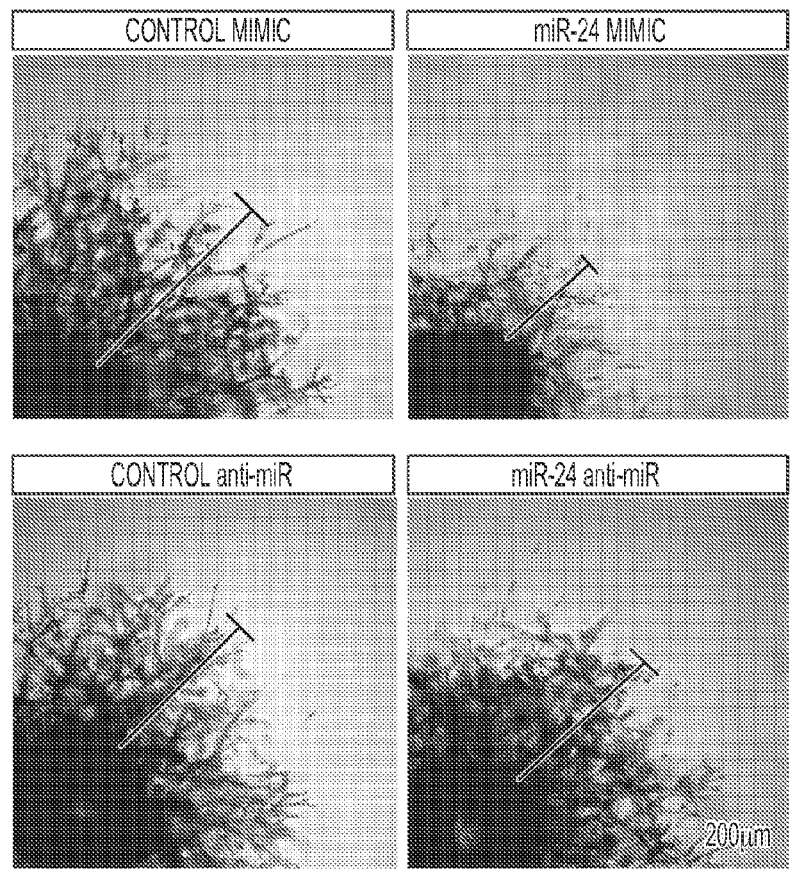
Figure 14F:
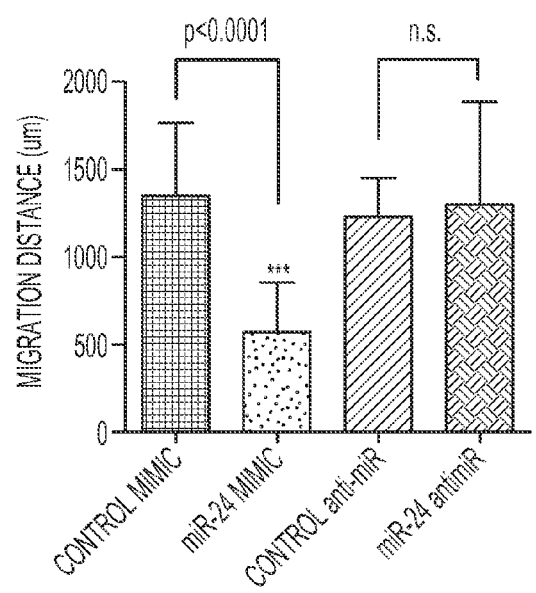

FIGS. 14A-F. Regulation of angiogenesis by miR-24 in vitro. (FIG. 14A). Representative pictures of in vitro EC tube formation after miR-24 mimic or anti-miR transfection and 8-hr culture in the Matrigel; (FIG. 14B). Quantification of branch points per field in FIG. 14A. ***, p<0.001. *, p<0.05; (FIG. 14C). Quantification of EC proliferation indicated by BrDU incorporation after miR-24 mimic transfection; (FIG. 14D). Representative pictures and quantification of scratch wound assays after miR-24 mimic transfection in ECs. *, p<0.001; n.s., not significant; (FIG. 14E). Representative pictures of ex vivo aortic ring assays at 6 days after miR-24 mimic or anti-miR transfection. Sprouting of the aortic ring cells is indicated by black lines; (FIG. 14F). Quantification of ex vivo aortic ring assays at 6 days after miR-24 mimic or anti-miR transfection. *, p<0.001; n.s., not significant.

Figure 15A:
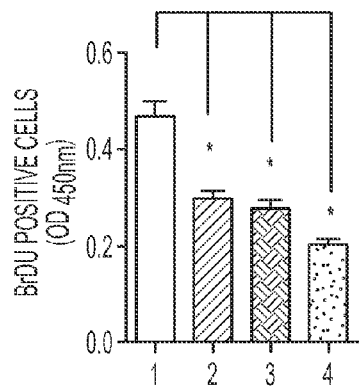
Figure 15B:
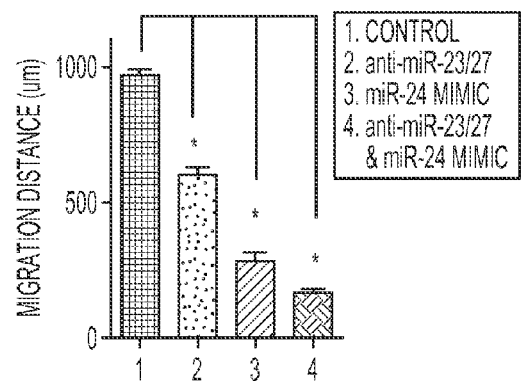
Figure 15C:
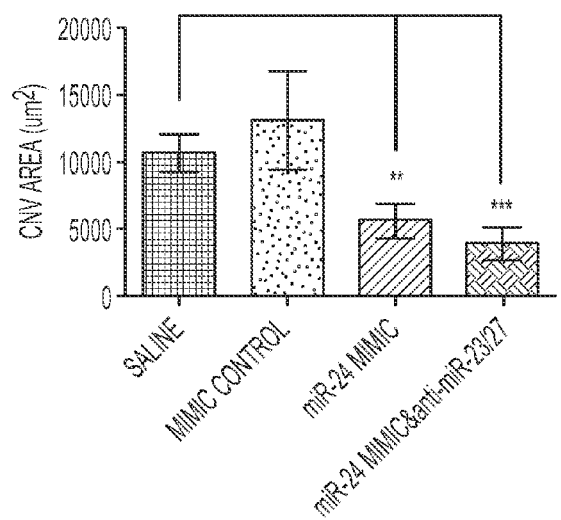

FIGS. 15A-C. Repression of CNV by miR-24 in vivo. (FIG. 15A). Synergistic repression of EC proliferation as revealed by BrDU incorporation assay by miR-24 mimic and miR-23/27 anti-miRs in vitro. *, p<0.05; (FIG. 15B). Synergistic repression of EC migration in a scratch wound assay by miR-24 mimic and miR-23/27 anti-miRs in vitro. *, p<0.05; (FIG. 15C). Quantification of laser-induced CNV (µm2) by miR-24 mimic or miR-24 mimic&miR-23/27 anti-miRs in vivo. Saline and control mimic were used as controls.

Figure 16:
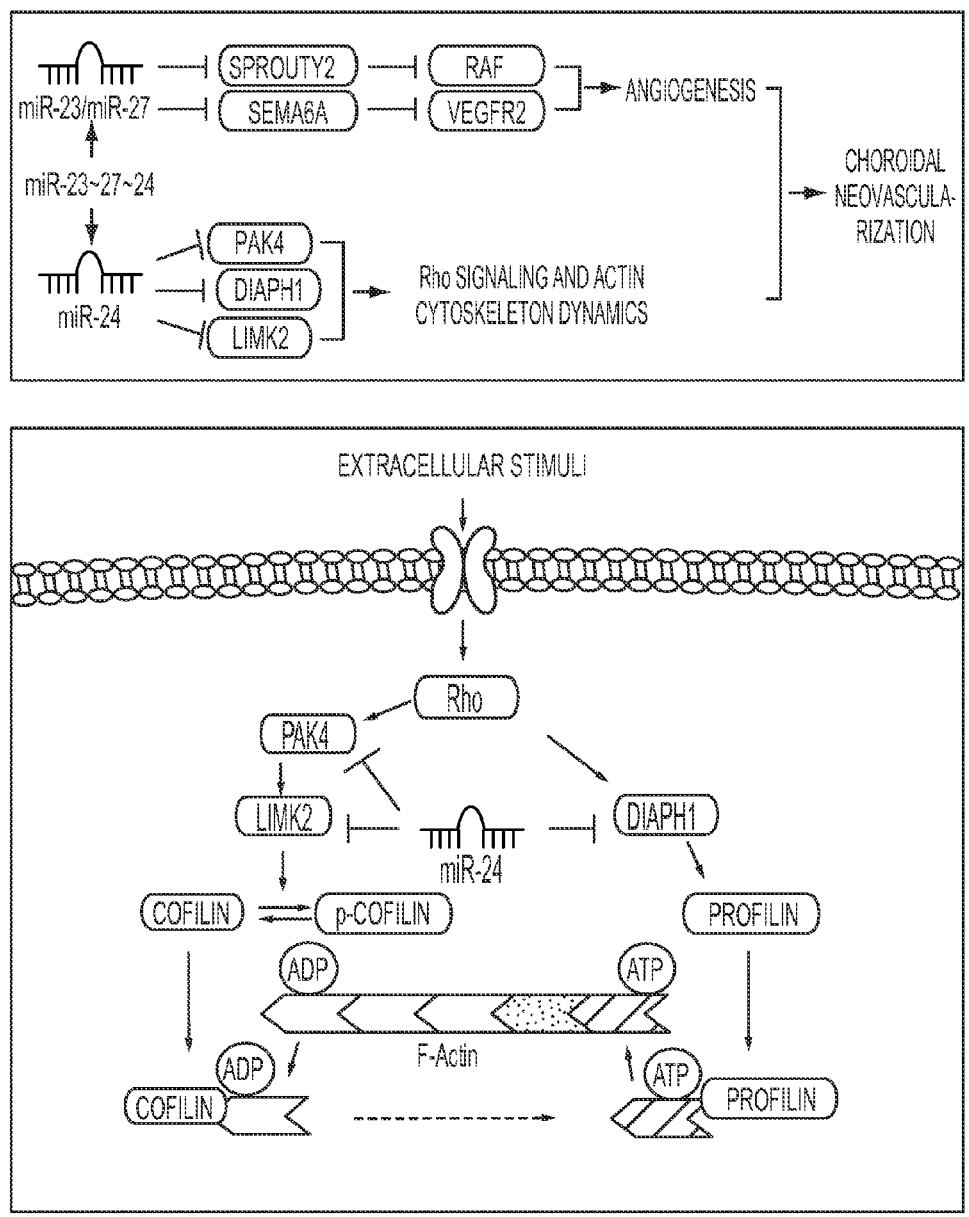

FIG. 16. A model for miR-23~27~24 in angiogenesis and CNV. In this model, miR-23/27 promote angiogenesis and CNV by repressing their target genes Sprouty2 (intracellular inhibitor of MAP kinase pathway) and Semaphorin 6A (Sema6A, a secreted protein which could inhibit VEGFR2 signaling). miR-24 represses angiogenesis and CNV by targeting proteins involved in Rho signaling and cytoskeleton actin dynamics, including Pak4, Limk2 and Diaph1.

FIGS. 17A-D. Regulation of miR-24 target proteins by miR-24 mimic and anti-miR in ECs. (FIG. 17A) Table showing several miR-24 target genes involved in cytoskeleton actin dynamics predicted by DIANA-mirPath software. The sequences in the target genes complementary to the miRNA seed regions are shown in bold type. The number of species in which the target sites are conserved is shown. (FIG. 17B) Dose dependent repression of DIAPH1, PAK4 and LIMK2 3' UTRs by miR-24 as shown by luciferase assays. miR-146, which was not predicted to target these UTRs, was used as controls. EZH2 UTR was used as a nonrelated control for testing miR-24 specificity. *, p<0.05; , p<0.01; *, p<0.0001; NS, not significant. (FIG. 17C) Regulation of miR-24 target proteins DIAPH1, PAK4 and LIMK2, as well as the phosphorylation of their downstream protein Cofilin by miR-24 mimic or anti-miR in HUVECs, as shown by Western blot analyses. Total Cofilin and GAPDH served as controls. (FIG. 17D) Regulation of ERK1/2 phosphorylation by miR-24 in HUVECs, as revealed by Western blot. GAPDH served as a loading control.

Figure 18A:
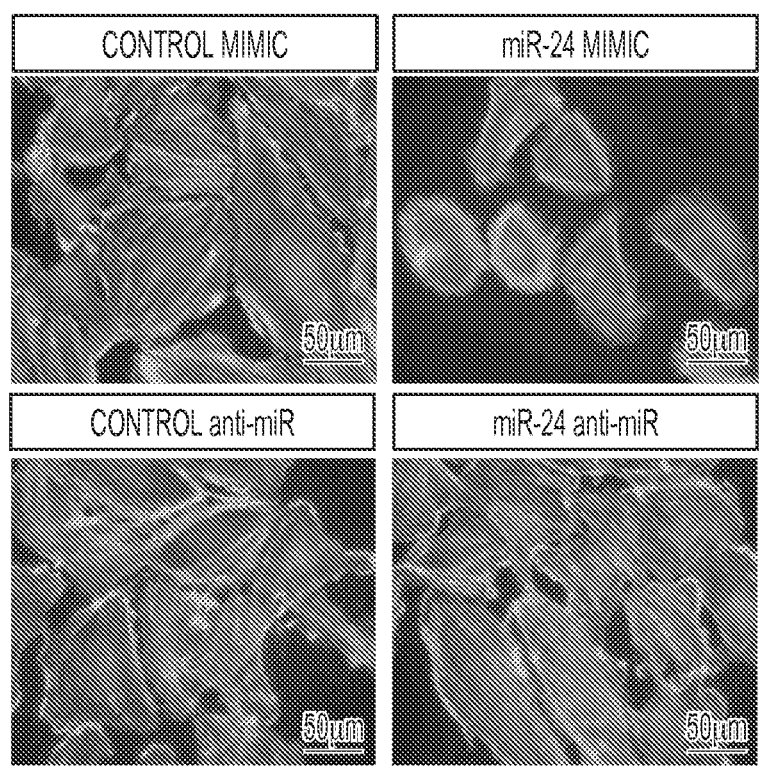
Figure 18B:
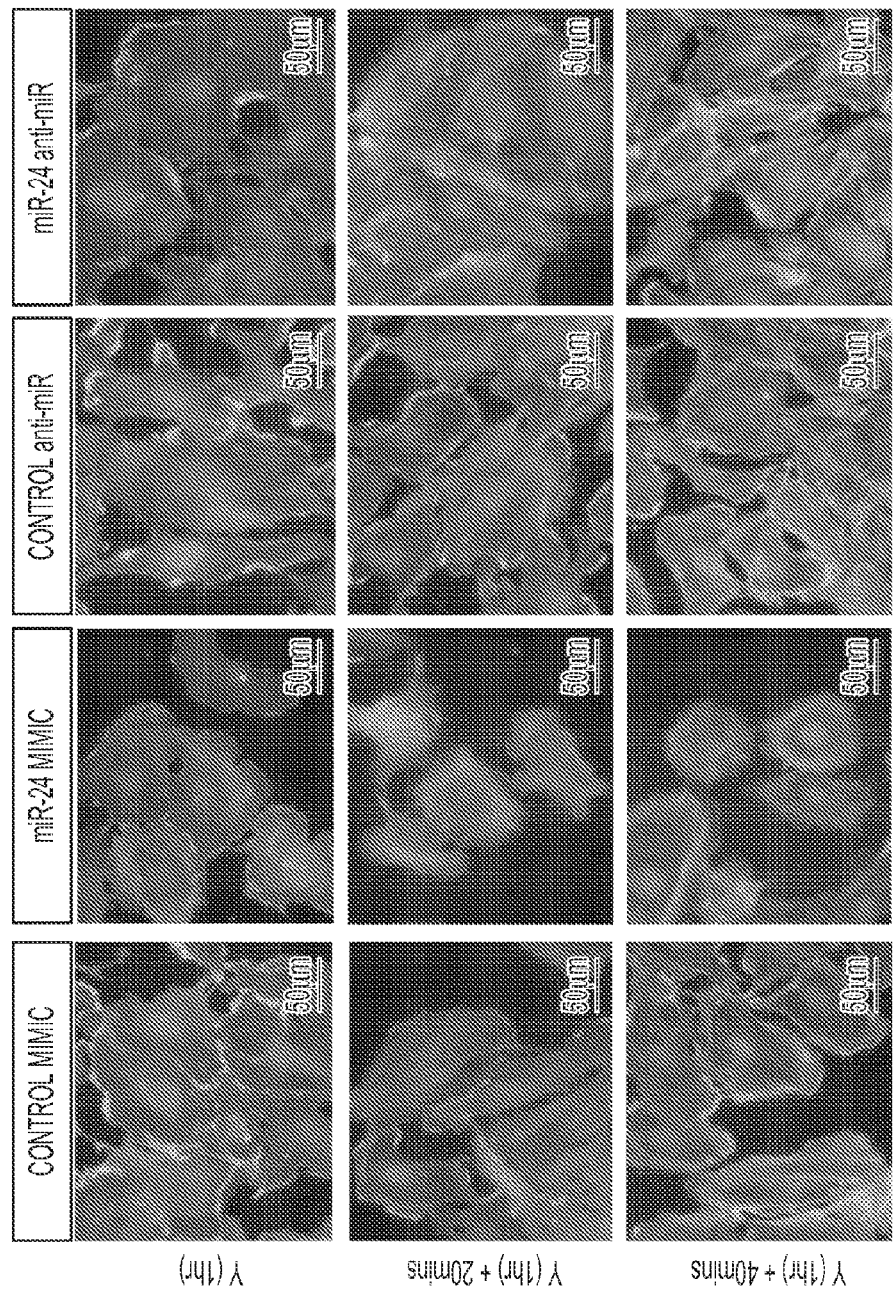

FIGS. 18A-B. Regulation of EC shape and actin dynamics by miR-24. (FIG. 18A) Stress fiber and shape changes in ECs transfected with miR-24 mimic, anti-miR or controls, as revealed by phalloidin staining Scale=50 µm. (FIG. 18B) Stress fiber formation in miR-24 mimic or anti-miR transfected ECs after 1 hour Rho inhibitor Y-27632 treatment. Scale=50 µm.

FIGS. 19A-H. Regulation of angiogenesis by miR-24 in vitro. (FIG. 19A) Representative pictures of in vitro EC tube formation after miR-24 mimic or anti-miR transfection and 8 hour culture in the Matrigel. (FIG. 19B) Quantification of branch points per field in FIG. 19A. ***, p<0.001. *, p<0.05. (FIG. 19C) Quantification of EC proliferation in EGM2 medium after starvation indicated by BrDU incorporation after miR-24 mimic transfection. (FIG. 19D) Quantification of EC proliferation in EGM2 medium after starvation indicated by BrDU incorporation after miR-24 anti-miR transfection. (FIG. 19E) Quantification of scratch wound EC migration after miR-24 mimic or anti-miR transfection in ECs. *, p<0.001; n.s., not significant. (FIG. 19F) Representative real-time pictures showing scratch wound EC migration after miR-24 mimic transfection. Black lines indicated the initial positions of cells. Time points were indicated. (FIG. 19G) Representative pictures of ex vivo aortic ring assays at 6 days after miR-24 mimic or antimiR transfection. Sprouting of the aortic ring cells is indicated by black lines. (FIG. 19H) Quantification of ex vivo aortic ring assays at 6 days after miR-24 mimic or anti-miR transfection. *, p<0.001; n.s., not significant.

FIGS. 20A-D. Regulation of retinal vascular development by miR-24. (FIG. 20A) Northern blot analysis showing upregulation of miR-24 in miR-24TG mice. U6 served as a loading control. (FIG. 20B) Flat mount ICAM-2 staining of retinal vasculature in P6 miR-24TG mice. (FIG. 20C) Quantification of retinal vasculature sprouting in P6 miR-24TG mice. (FIG. 20D) Confocal imaging of retinal vasculature in adult miR-24TG mice. Genotypes of the mice were indicated. The left panel showed images from the most superficial layer; the middle panels showed pseudo-colored images in an intermediate layers and deep layers of the retinas. The right panel showed the merged pictures.

Figure 21A:
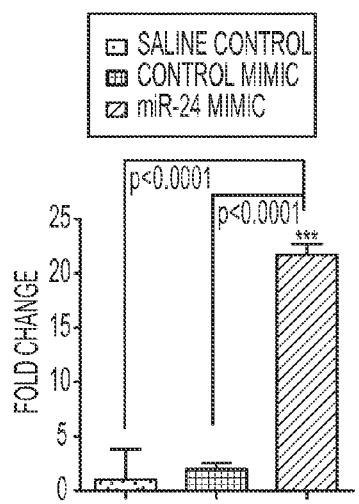
Figure 21C:
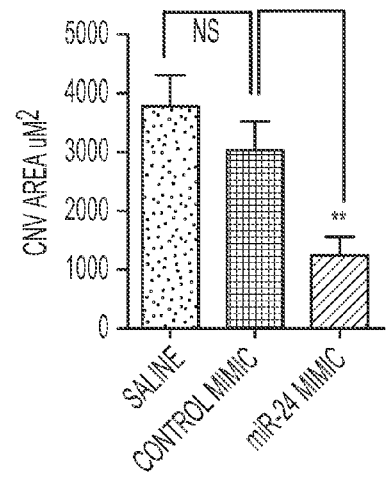
Figure 21B:
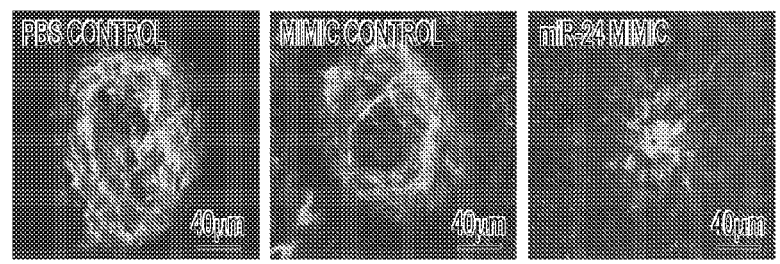

FIGS. 21A-D. Repression of laser-induced CNV by miR-24 in vivo. (FIG. 21A) Real-time PCR showing upregulation of miR-24 by miR-24 mimics in the posterior eyes. *, p<0.0001. (FIG. 21B). Representative images showing repression of laser-induced CNV by miR-24 mimics. Scale bar=20 μm. (FIG. 21C) Quantification of CNV area (μm$^2$) in FIG. 21B. Saline and control mimic were used as controls. , 5 p<0.01. (FIG. 20D). Representative images of ICAM-2 staining from frozen sections of laser lesions. Scale bar=50 μm. miRNA mimic treatments were indicated and the lesion areas were labeled by dashed lines.

FIGS. 22A-E. Mimicking of the miR-24 overexpression phenotype by silencing of miR-24 target genes in vitro. (FIG. 22A). Western blots showing efficient silencing of DIAPH1, LIMK2, PAK4 and 10 LIMK1 in HUVECs with specific siRNAs at 50 nM and 100 nM. (FIG. 22B) Representative phalloidin staining showing actin fiber structure and cellular distribution after DIAPH1, LIMK2 or PAK4 knockdown in ECs. (FIG. 22C) Representative images of in vitro Matrigel assays after DIAPH1, LIMK2 or PAK4 knockdown in ECs. (FIG. 22D) Quantification of EC migration in response to wound scratch after LIMK2 or PAK4 knockdown. (FIG. 22E) Quantification of EC proliferation after LIMK2 or PAK4 knockdown.

Figure 23:
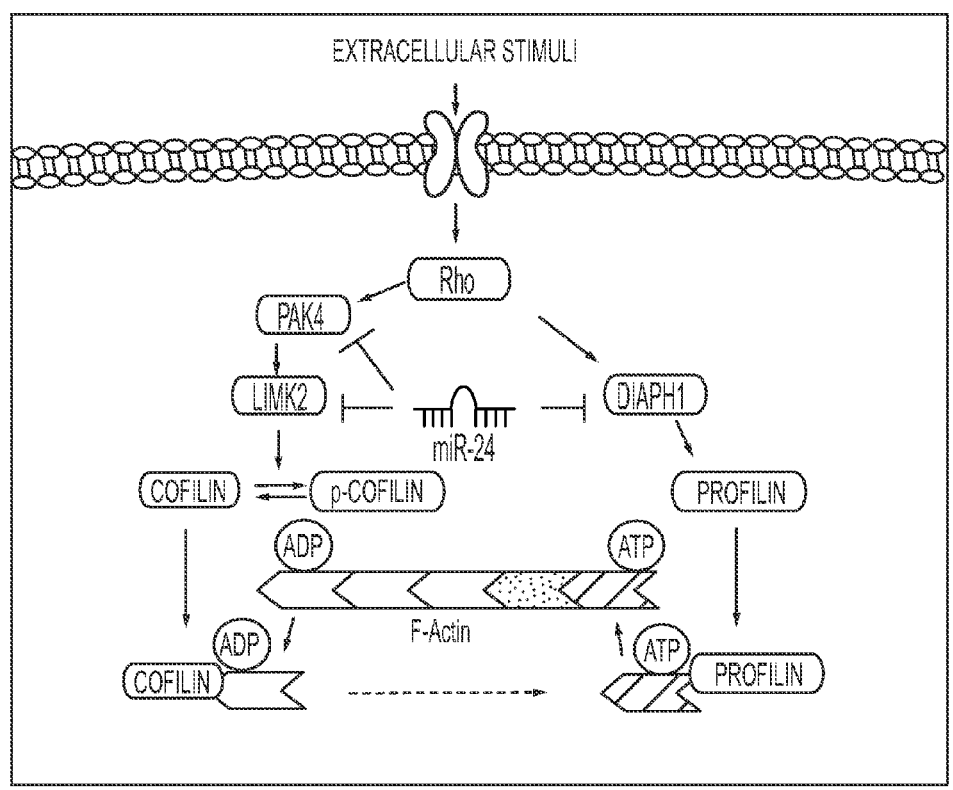

FIG. 23. A model for miR-23~27~24 in angiogenesis and CNV. In response to extracellular stimuli, Rho signaling activates DIAPH1, PAK4 and LIMK2, which function to regulate actin polymerization/depolymerization. miR-24 targets on PAK4 and LIMK2 downstream of Rho signaling, therefore repressing Cofilin phosphorylation and promoting actin-depolymerization. In addition, miR-24 also targets on DIAPH1 downstream of Rho signaling, therefore repressing the actin polymerization through Profilin. By targeting key proteins involved in actin cytoskeleton dynamics, miR-24 represses angiogenesis and choroidal neovascularization in the retina.

DETAILED DESCRIPTION OF ILLUSTRATIVE EMBODIMENTS

The miR-23~27~24 clusters are highly expressed in ECs (Poliseno et al., 2006; Suarez et al., 2007; Kuehbacher et al., 2007; Harris et al., 2008). Two miR-23~27~24 clusters exist in the vertebrate genome: an intergenic miR-23a~27a~24-2 cluster and an intronic miR-23b~27b~24-1 cluster. Members of these clusters are involved in cell cycle control, proliferation and differentiation of various cell types (Chhabra et al., 2010). The inventors show that inhibition of miR-23/27 impairs angiogenesis in vitro and postnatal retinal vascular development in vivo. Moreover, silencing of miR-23/27 suppresses laser-induced CNV in mice. The pro-angiogenic functions of miR-23/27 correlate with the repression of Sprouty2 and Sema6A, which negatively regulate angiogenic signaling.

The inventors also provide evidence that miR-24 regulates actin dynamics in endothelial cells (ECs) through targeting multiple members downstream of Rho signaling, including LIMK2, PAK4 and DIAPH1. Either overexpression of miR-24, or knockdown of its target genes LIMK2 or PAK4, results in a block in actin fiber formation, as well as repression in angiogenesis in vitro. Transgenic overexpression of miR-24 in mice represses postnatal retinal vascular development, while subretinal delivery of miR-24 mimics represses laser-induced CNV in vivo. These findings support a novel model for miR-24 in repressing angiogenesis by simultaneously regulating multiple components in the actin cytoskeleton pathways. Overexpression of miR-24 also blocks stress fiber and lamellipodia formation, therefore repressing EC migration and proliferation; while knockdown of miR-24 shows a trend to enhance stress fiber formation. In all, these data support an important role of miR-24 in regulating actin cytoskeleton dynamics and angiogenesis, which will have implication in a variety of vascular diseases.

Additionally, miR-23/27 anti-miRs and miR-24 mimic show synergistic effect in repressing EC proliferation and migration in vitro, as well as laser-induced CNV in vivo. Together, these findings suggest that miR-23/27 and miR-24 have distinct functions in angiogenesis. Manipulation of miR-23/27 and miR-24 levels may achieve superior outcome in regulating angiogenesis than individual miRNAs, and therefore represents an attractive therapeutic target for treatment of wet AMD and other vascular diseases. These and other aspects of the invention are described in detail below.

I. Age-Related Macular Degeneration (AMD)

Macular degeneration is the leading cause of blindness in individuals over 55. It is caused by the physical disturbance of the center of the retina, called the macula. The macula is the part of the retina which is responsible for the most acute and detailed vision. Therefore, it is critical for reading, driving, recognizing faces, watching television, and fine work. Even with a loss of central vision, however, color vision and peripheral vision may remain clear. Vision loss usually occurs gradually and typically affects both eyes at different rates.

The root causes of macular degeneration are still unknown. There are two forms of age-related macular degeneration, "wet" and "dry." Seventy percent of patients have the dry form, which involves thinning of the macular tissues and disturbances in its pigmentation. Thirty percent have the wet form, which can involve bleeding within and beneath the retina, opaque deposits, and eventually scar tissue. The wet form accounts for ninety percent of all cases of legal blindness in macular degeneration patients. Different forms of macular degeneration may occur in younger patients. These non-age related cases may be linked to heredity, diabetes, nutritional deficits, head injury, infection, or other factors.

Declining vision noticed by the patient or by an ophthalmologist during a routine eye exam may be the first indicator of macular degeneration. The formation of new blood vessels and exudates, or "drusen," from blood vessels in and under the macular is often the first physical sign that macular degeneration may develop. In addition, the following signs may be indicative of macular problems. Other symptoms indicative of developing macular degeneration include (a) straight lines appear distorted and, in some cases, the center of vision appears more distorted than the rest of the scene; (b) a dark, blurry area or "white-out" appears in the center of vision; (c) color perception changes or diminishes. In the early stages, only one eye may be affected, but as the disease progresses, both eyes are usually affected.

Early detection is important because a patient destined to develop macular degeneration can sometimes be treated before symptoms appear, and this may delay or reduce the severity of the disease. Furthermore, as better treatments for macular degeneration are developed, whether medicinal, surgical, or low vision aids, patients diagnosed with macular degeneration can sooner benefit from them. However, there presently is no cure for macular degeneration. In some cases, macular degeneration may be active and then slow down considerably, or even stop progressing for many, many years. There are ways to arrest macular degeneration, depending on the type and the degree of the condition. These range from nutritional intervention to laser surgery of the blood vessels.

Some scientists have suggested an association between macular degeneration and high saturated fat, low carotenoid pigments, and other substances in the diet. There is evidence that eating fresh fruits and dark green, leafy vegetables (such as spinach and collard greens) may delay or reduce the severity of age-related macular degeneration. Taking anti-oxidants like vitamins C and E may also have positive effects. Zinc, however, has shown mixed results. In some people, the long-term use of zinc causes digestive problems and anemia; its use is probably not worth the potential problems. Selenium is sometimes recommended.

Surgery to remove the scar produced by macular degeneration has been successful in younger patients, but less successful in older patients. If the degeneration is associated with leaking blood vessels in the center of the macula, and vision is worse than 20/70, laser surgery, called photocoagulation, is recommended. This will not improve vision but generally reduces further vision loss. Retinal transplantation is a new experimental approach to macular degeneration, but will require additional clinical research to determine safety and effectiveness.

The proliferation of abnormal blood vessels in the retina is stimulated by vascular endothelial growth factor (VEGF). Anti-angiogenics or anti-VEGF agents can cause regression of the abnormal blood vessels and improve vision when injected directly into the vitreous humor of the eye. The injections must be repeated monthly or bi-monthly. Several anti-angiogenic drugs have been approved for use in the eye by the U.S. Food and Drug Administration and regulatory agencies in other countries. The first major anti-VEGF agent was bevacizumab (Avastin), which was approved for use in cancer. Bevacizumab is a monoclonal antibody. Genentech, the manufacturer, developed bevacizumab into a smaller molecule, ranibizumab (Lucentis), for use in the eye, and received FDA approval for use in wet AMD.

Macular degeneration appears to be hereditary in some families, but not in others. Another factor is uv-radiation. It has been demonstrated that the blue rays of the spectrum seem to accelerate macular degeneration more than other rays of the spectrum. This means that very bright light, such as sunlight or its reflection in the ocean and desert, may worsen macular degeneration. Special sunglasses that block out the blue end of the spectrum may decrease the progress of the disease. Hypertension tends to make some forms of macular degeneration worse, especially in the wet form where the retinal tissues are invaded by new blood vessels. Finally, smoking or exposure to tobacco smoke can accelerate the development of the wet type of macular degeneration

II. miRNAs

A. Background

In 2001, several groups used a novel cloning method to isolate and identify a large group of "microRNAs" (miR-NAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets.

miRNAs are transcribed by RNA polymerase II and can be derived from individual miRNA genes, from introns of protein coding genes, or from poly-cistronic transcripts that often encode multiple, closely related miRNAs. Pre-miR-NAs, generally several thousand bases long are processed in the nucleus by the RNase Drosha into 70- to 100-nt hairpin-shaped precursors. Following transport to the cytoplasm, the hairpin is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Krania, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs.

The first miRNAs were identified as regulators of developmental timing in *C. elegans*, suggesting that miRNAs, in general, might play decisive regulatory roles in transitions between different developmental states by switching off specific targets (Fatkin et al., 2000; Lowes et al., 1997). However, subsequent studies suggest that miRNAs, rather than functioning as on-off "switches," more commonly function to modulate or fine-tune cell phenotypes by repressing expression of proteins that are inappropriate for a particular cell type, or by adjusting protein dosage. miRNAs have also been proposed to provide robustness to cellular phenotypes by eliminating extreme fluctuations in gene expression.

Research on microRNAs is increasing as scientists are beginning to appreciate the broad role that these molecules play in the regulation of eukaryotic gene expression. The two best understood miRNAs, lin-4 and let-7, regulate developmental timing in *C. elegans* by regulating the translation of a family of key mRNAs (reviewed in Pasquinelli and Ruvkum, 2002). Several hundred miRNAs have been identified in *C. elegans, Drosophila*, mouse, and humans. As would be expected for molecules that regulate gene expression, miRNA levels have been shown to vary between tissues and developmental states. In addition, one study shows a strong correlation between reduced expression of two miRNAs and chronic lymphocytic leukemia, providing a possible link between miRNAs and cancer (Calin et al., 2002). Although the field is still young, there is speculation that miRNAs could be as important as transcription factors in regulating gene expression in higher eukaryotes.

There are a few examples of miRNAs that play critical roles in cell differentiation, early development, and cellular processes like apoptosis and fat metabolism. lin-4 and let-7 both regulate passage from one larval state to another during *C. elegans* development (Ambros, 2003). mir-14 and bantam are *drosophila* miRNAs that regulate cell death, apparently by regulating the expression of genes involved in apoptosis (Brennecke et al., 2003, Xu et al., 2003). miR-14 has also been implicated in fat metabolism (Xu et al., 2003). Lsy-6 and miR-273 are *C. elegans* miRNAs that regulate asymmetry in chemosensory neurons (Chang et al., 2004). Another animal miRNA that regulates cell differentiation is miR-181, which guides hematopoietic cell differentiation (Chen et al., 2004). These molecules represent the full range of animal miRNAs with known functions. Enhanced understanding of the functions of miRNAs will undoubtedly reveal regulatory networks that contribute to normal development, differentiation, inter- and intracellular communication, cell cycle, angiogenesis, apoptosis, and many other cellular processes. Given their important roles in many biological functions, it is likely that miRNAs will offer important points for therapeutic intervention or diagnostic analysis.

Characterizing the functions of biomolecules like miRNAs often involves introducing the molecules into cells or removing the molecules from cells and measuring the result. If introducing a miRNA into cells results in apoptosis, then the miRNA undoubtedly participates in an apoptotic pathway. Methods for introducing and removing miRNAs from cells have been described. Two recent publications describe antisense molecules that can be used to inhibit the activity of specific miRNAs (Meister et al., 2004; Hutvagner et al., 2004), and others have proven their functionality in the heart, where they efficiently knocked-down miR-133 and miR-1 (Care et al. 2007; Yang et al. 2007). Another publication describes the use of plasmids that are transcribed by endogenous RNA polymerases and yield specific miRNAs when transfected into cells (Zeng et al., 2002). These two reagent sets have been used to evaluate single miRNAs.

B. miR-23 miR-23 exists in two forms, miR23a and miR23b. miR-23 was previously named miR-23, but was renamed here to avoid confusion with the later described miR-23b. miR-23 was initially reported to regulate the transcriptional repressor hairy enhancer of split (HES1), but the finding was later retracted after the discovery that the regulated gene was human homolog of ES1 (HES1), whose function is unknown. miR-23b was initially predicted based on homology to a verified miRNA from mouse, later verified in human. The sequences are shown below:

```
miR-23a
                                          (SEQ ID NO: 1)
aucacauugccagggauuucc miR-23b
                                          (SEQ ID NO: 2)
aucacauugccagggauuacc
```

C. miR-24

The miR-24 microRNA precursor is a small non-coding RNA molecule that regulates gene expression. microRNAs are transcribed as ~70 nucleotide precursors and subsequently processed by the Dicer enzyme to give a mature ~22 nucleotide product. In this case the mature sequence comes from the 3' arm of the precursor. The mature products are thought to have regulatory roles through complementarity to mRNA. miR-24 has been identified in human and mouse. It has suggested roles in (a) suppressing the tumor suppressor p16(INK4a), (b) reducing the mRNA and protein levels of human ALK4 by targeting the 3'-untranslated region of mRNA, and (c) targeting the DHFR gene. miR-24 has been characterized in two forms, miR24-2 and miR24-1, but the sequences are the same. The sequence is shown below:

```
miR-24-2
                                          (SEQ ID NO: 3)
uggcucaguucagcaggaacag miR-24-1
                                          (SEQ ID NO: 4)
uggcucaguucagcaggaacag
```

D. miR-27 miR-27 exits in two forms, miR27a and miR27b, and represent a family of microRNA precursors found in animals, including humans. MicroRNAs are typically transcribed as ~70 nucleotide precursors and subsequently processed by the Dicer enzyme to give a ~22 nucleotide product. The excised region or, mature product, of the miR-27 precursor is the microRNA mir-27. *Herpesvirus saimiri* expresses several non-coding RNAs (HSURs) which have been found to significantly reduce the level of mir-27 in a host cell. It has been proposed that miR-27 operates together with miR-23 and mir-24 in a co-operative cluster. miR-27a was previously named miR-27, but was renamed to avoid confusion with the later described miR-27b Lagos-Quintana et al. (2002) determined the expression of miR-27b in mouse, and a human sequence was predicted based on homology. Michael et al. (2003) subsequently verified the expression of this miRNA in human cells. The sequences are shown below:

```
miR-27a
                                          (SEQ ID NO: 5)
uucacaguggcuaaguuccgc miR-27b
                                          (SEQ ID NO: 6)
uucacaguggcuaaguucugc
```

E. Agonists and Antagonists of miRs

Agonists of miR-24 will generally take one of three forms. First, there is miR-24 itself. Such molecules may be delivered to target cells, for example, by injection or infusion, optionally in the a delivery vehicle such as a lipid, such as a liposome or lipid emulsion. Second, one may use expression vectors that drive the expression of miR-24. The composition and construction of various expression vectors is described elsewhere in the document. Third, one may use agents distinct from miR-24 that act up-regulate, stabilize or otherwise enhance the activity of miR-24, including small molecules. Such molecules include "mimetics," molecules which mimic the function, and possibly form of miR-126, but are distinct in chemical structure.

Antagonism of miRNA function may, in example, be achieved by "antagomirs." Initially described by Krützfeldt and colleagues (Krützfeldt et al., 2005), antagomirs are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol moiety at its 3' end. Antagomirs suitable for inhibiting miRNAs may be about 14 to about 50 nucleotides in length, about 14 to about 30 nucleotides in length, and 14 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

Inhibition of miRNA function may also be achieved by administering antisense oligonucleotides. The antisense oligonucleotides may be ribonucleotides or deoxyribonucleotides. Preferably, the antisense oligonucleotides have at least one chemical modification. Antisense oligonucleotides may be comprised of one or more "locked nucleic acids." "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g., 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Particular antisense oligonucleotides useful for inhibiting the activity of microRNAs are about 19 to about 25 nucleotides in length. Antisense oligonucleotides may comprise a sequence that is at least partially complementary to a mature miRNA sequence, e.g., at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

Another approach for inhibiting the function of an miR is administering an inhibitory RNA molecule having at least partial sequence identity to the mature miR sequence. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical, e.g., about 75%, 80%, 85%, 90%, 95%, 96%, 97%, 98%, or 99% identical, to the mature miRNA sequence. In some embodiments, the double-stranded regions of the inhibitory RNA comprise a sequence that is at least substantially identical to the mature miRNA sequence. "Substantially identical" refers to a sequence that is at least about 95%, 96%, 97%, 98%, or 99% identical to a target polynucleotide sequence. In other embodiments, the double-stranded regions of the inhibitory RNA molecule may contain 100% identity to the target miRNA sequence.

In other embodiments of the invention, inhibitors of an miR may be inhibitory RNA molecules, such as ribozymes, siRNAs, or shRNAs. In one embodiment, an inhibitor of miR-499 is an inhibitory RNA molecule comprising a double-stranded region, wherein the double-stranded region comprises a sequence having 100% identity to the mature miR sequence. In some embodiments, inhibitors are inhibitory RNA molecules which comprise a double-stranded region, wherein said double-stranded region comprises a sequence of at least about 75%, 80%, 85%, 90%, 95%, 96%, 97%, 98%, or 99% identity to the mature miR sequence.

III. Methods of Treatment

A. Pharmacological Therapeutic Agents and Administration

The present invention addresses therapies, e.g., treatment of age-related macular degeneration. In various embodiments, the inhibitory agents of the present invention are formulated for administration in pharmacologically acceptable vehicles, such as parenteral, topical, aerosal, liposomal, nasal or ophthalmic preparations. In certain embodiments, formulations may be designed for oral or topical administration. It is further envisioned that formulations of nucleic acids encoding cytoskeletal stabilizing proteins and any other agents that might be delivered may be formulated and administered in a manner that does not require that they be in a single pharmaceutically acceptable carrier. In those situations, it would be clear to one of ordinary skill in the art the types of diluents that would be proper for the proposed use of the polypeptides and any secondary agents required.

The phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions, vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue or surface is available via that route. This includes oral, nasal, or topical. Alternatively, administration may be by introcular, intra-hepatic, orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Combined Therapy

In another embodiment, it is envisioned to use the agonists/antagonists of the present invention in combination with other therapeutic modalities. Thus, in addition to the therapies described above, one may also provide to the patient more "standard" pharmaceutical therapies. Combinations may be achieved by contacting cells, tissues or subjects with a single composition or pharmacological formulation that includes both agents, or by contacting the cell with two distinct compositions or formulations, at the same time, wherein one composition includes the agonist/antagonist and the other includes the other agent. Alternatively, the therapy using an agonist/antagonist may precede or follow administration of the other agent(s) by intervals ranging from minutes to weeks. In embodiments where the other agent and agonist/antagonist are applied separately to the cell, one would generally ensure that a significant period of time did not expire between the time of each delivery, such that the agent and the agonist/antagonist would still be able to exert an advantageously combined effect on the cell, tissue or subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a modulator of miR, or the other agent will be desired. In this regard, various combinations may be employed. By way of illustration, where the agonist/antagonist(s) is "A" and the other agent is "B," the following permutations based on 3 and 4 total administrations are exemplary:

| A/B/A | B/A/B | B/B/A | A/A/B | B/A/A | A/B/B |
|-------|-------|-------|-------|-------|-------|
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated.

Particularly useful combination therapies will include The proliferation of abnormal blood vessels in the retina is stimulated by vascular endothelial growth factor (VEGF). Anti-angiogenics or anti-VEGF agents can cause regression of the abnormal blood vessels and improve vision when injected directly into the vitreous humor of the eye. The injections must be repeated monthly or bi-monthly. Several anti-angiogenic drugs have been approved for use in the eye by the U.S. Food and Drug Administration and regulatory agencies in other countries.

The first major anti-VEGF agent was bevacizumab (Avastin), which was approved for use in cancer. Bevacizumab is a monoclonal antibody. Genentech, the manufacturer, developed bevacizumab into a smaller molecule, ranibizumab (Lucentis), for use in the eye, and received FDA approval for use in wet AMD. Bevacizumab is packaged and used for cancer in larger doses than the doses used in the eye. Bevacizumab can be administered in smaller doses in the eye, off label, at a cost of less than one-tenth that of ranibizumab per treatment in the United Kingdom. This use is controversial, and eye infections have been reported as a result of dividing the doses.

Other anti-angiogenic drugs are pegaptanib (Macugen), aflibercept (Eylea) for treatment of wet AMD, and Pegaptanib (Macugen) for neovascular AMD. Photodynamic therapy has also been used to treat wet AMD.

C. Other Neovascular Disease States

As discussed above, the present invention provides for the use of agonists/antagonists of miR-23, 24 and/or 27 impede neovasculariziation that leads to or contributes to age-related macular degeneration. The following additional disease states/conditions are specifically contemplated for treatment according to the present invention, but are not limiting.

Atherosclerosis. Atherosclerosis is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a "hardening" of the arteries. It is caused by the formation of multiple plaques within the arteries.

Atherosclerosis typically begins in early adolescence, and is usually found in most major arteries, yet is asymptomatic and not detected by most diagnostic methods during life. The stage immediately prior to actual atherosclerosis is known as subclinical atherosclerosis. It most commonly becomes seriously symptomatic when interfering with the coronary circulation supplying the heart or cerebral circulation supplying the brain, and is considered the most important underlying cause of strokes, heart attacks, various heart diseases including congestive heart failure, and most cardiovascular diseases, in general. Atheroma in arm, or more often in leg arteries, which produces decreased blood flow is called Peripheral artery occlusive disease (PAOD). Most artery flow disrupting events occur at locations with less than 50% lumen narrowing (~20% stenosis is average).

Although the disease process tends to be slowly progressive over decades, it usually remains asymptomatic until an atheroma obstructs the bloodstream in the artery. This is typically by rupture of an atheroma, clotting and fibrous organization of the clot within the lumen, covering the rupture but also producing stenosis, or over time and after repeated ruptures, resulting in a persistent, usually localized stenosis. Stenoses can be slowly progressive, whereas plaque rupture is a sudden event that occurs specifically in atheromas with thinner/weaker fibrous caps that have become "unstable."

Repeated plaque ruptures, ones not resulting in total lumen closure, combined with the clot patch over the rupture and healing response to stabilize the clot, is the process that produces most stenoses over time. The stenotic areas tend to become more stable, despite increased flow velocities at these narrowings. Most major blood-flow-stopping events occur at large plaques, which, prior to their rupture, produced very little if any stenosis.

From clinical trials, 20% is the average stenosis at plaques that subsequently rupture with resulting complete artery closure. Most severe clinical events do not occur at plaques that produce high-grade stenosis. From clinical trials, only 14% of heart attacks occur from artery closure at plaques producing a 75% or greater stenosis prior to the vessel closing.

If the fibrous cap separating a soft atheroma from the bloodstream within the artery ruptures, tissue fragments are exposed and released, and blood enters the atheroma within the wall and sometimes results in a sudden expansion of the atheroma size. Tissue fragments are very clot-promoting, containing collagen and tissue factor; they activate platelets and activate the system of coagulation. The result is the formation of a thrombus (blood clot) overlying the atheroma, which obstructs blood flow acutely. With the obstruction of blood flow, downstream tissues are starved of oxygen and nutrients. If this is the myocardium (heart muscle), angina (cardiac chest pain) or myocardial infarction (heart attack) develops.

If atherosclerosis leads to symptoms, some symptoms such as angina pectoris can be treated. Non-pharmaceutical means are usually the first method of treatment, such as cessation of smoking and practicing regular exercise. If these methods do not work, medicines are usually the next step in treating cardiovascular diseases, and, with improvements, have increasingly become the most effective method over the long term. However, medicines are criticized for their expense, patented control and occasional undesired effects.

In general, the group of medications referred to as statins has been the most popular and are widely prescribed for treating atherosclerosis. They have relatively few short-term or longer-term undesirable side-effects, and multiple comparative treatment/placebo trials have fairly consistently shown strong effects in reducing atherosclerotic disease 'events' and generally ~25% comparative mortality reduction in clinical trials, although one study design, ALLHAT, was less strongly favorable.

The newest statin, rosuvastatin, has been the first to demonstrate regression of atherosclerotic plaque within the coronary arteries by IVUS (intravascular ultrasound evaluation), The study was set up to demonstrate effect primarily on atherosclerosis volume within a 2 year time-frame in people with active/symptomatic disease (angina frequency also declined markedly) but not global clinical outcomes, which was expected to require longer trial time periods; these longer trials remain in progress.

However, for most people, changing their physiologic behaviors, from the usual high risk to greatly reduced risk, requires a combination of several compounds, taken on a daily basis and indefinitely. More and more human treatment trials have been done and are ongoing that demonstrate improved outcome for those people using more-complex and effective treatment regimens that change physiologic behaviour patterns to more closely resemble those that humans exhibit in childhood at a time before fatty streaks begin forming Retinopathy. Retinopathy is a general term that refers to some form of non-inflammatory damage to the retina of the eye. Most commonly it is a problem with the blood supply that is the cause for this condition. Frequently, retinopathy is an ocular manifestation of systemic disease. Retinopathy is diagnosed by an optometrist or an ophthalmologist during ophthalmoscopy. Treatment depends on the cause of the disease.

The main causes of non-AMD retinopathy are diabetes, causing diabetic retinopathy; arterial hypertension, causing hypertensive retinopathy; prematurity of the newborn, causing retinopathy of prematurity (ROP); or genetic retinopathy. Many types of retinopathy are progressive and may result in blindness or severe vision loss or impairment, particularly if the macula becomes affected.

Coronary artery disease. Coronary heart disease is the narrowing or blockage of the coronary arteries, usually caused by atherosclerosis. Atherosclerosis (sometimes called "hardening" or "clogging" of the arteries) is the buildup of cholesterol and fatty deposits (called plaques) on the inner walls of the arteries. These plaques can restrict blood flow to the heart muscle by physically clogging the artery or by causing abnormal artery tone and function. Without an adequate blood supply, the heart becomes starved of oxygen and the vital nutrients it needs to work properly. This can cause chest pain called angina. If blood supply to a portion of the heart muscle is cut off entirely, or if the energy demands of the heart become much greater than its blood supply, a heart attack (injury to the heart muscle) may occur. It is most commonly equated with atherosclerotic coronary artery disease, but coronary disease can be due to other causes, such as coronary vasospasm, where the stenosis to be caused by spasm of the blood vessels of the heart it is then usually called Prinzmetal's angina.

Coronary artery disease, the most common type of coronary disease, which has no clear etiology, has many risk factors, including smoking, radiotherapy to the chest, chest pains, hypertension, obesity, diabetes, high alcohol consumption, lack of exercise, inability to manage stress, and hyperlipidemia. Also, having a type A behavior pattern, a group of personality characteristics including time urgency and competitiveness, is linked to an increased risk of coronary disease.

Cholesterol lowering medications, such as statins, are useful to decrease the amount of "bad" (LDL) cholesterol. ACE inhibitors, which treat hypertension and may lower the risk of recurrent myocardial infarction. Calcium channel blockers and/or beta-blockers and aspirin are also used.

Cancer. Cancers comprise a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not. The branch of medicine concerned with the study, diagnosis, treatment, and prevention of cancer is oncology.

Radiation therapy (also called radiotherapy, X-ray therapy, or irradiation) is the use of ionizing radiation to kill cancer cells and shrink tumors. Radiation therapy can be administered externally via external beam radiotherapy (EBRT) or internally via brachytherapy. Radiation therapy may be used to treat almost every type of solid tumor, including cancers of the brain, breast, cervix, larynx, lung, pancreas, prostate, skin, stomach, uterus, or soft tissue sarcomas. Radiation is also used to treat leukemia and lymphoma. Radiation dose to each site depends on a number of factors, including the radiosensitivity of each cancer type and whether there are tissues and organs nearby that may be damaged by radiation. Thus, as with every form of treatment, radiation therapy is not without its side effects.

Chemotherapy is the treatment of cancer with drugs that can destroy cancer cells. In current usage, the term "chemotherapy" usually refers to cytotoxic drugs which affect rapidly dividing cells in general, in contrast with targeted therapy (see below). Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can. Hence, chemotherapy has the potential to harm healthy tissue, especially those tissues that have a high replacement rate (e.g., intestinal lining). These cells usually repair themselves after chemotherapy. Because some drugs work better together than alone, two or more drugs are often given at the same time. This is called "combination chemotherapy," and indeed, most chemotherapy regimens are given in a combination.

Targeted therapy, which first became available in the late 1990's, has had a significant impact in the treatment of some types of cancer, and is currently a very active research area. This constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors imatinib and gefitinib.

Monoclonal antibody therapy is another strategy in which the therapeutic agent is an antibody which specifically binds to a protein on the surface of the cancer cells. Examples include the anti-HER2/neu antibody trastuzumab (Herceptin) used in breast cancer, and the anti-CD20 antibody rituximab, used in a variety of B-cell malignancies.

Targeted therapy can also involve small peptides as "homing devices" which can bind to cell surface receptors or affected extracellular matrix surrounding the tumor. Radionuclides which are attached to this peptides (e.g., RGDs) eventually kill the cancer cell if the nuclide decays in the vicinity of the cell. Especially oligo- or multimers of these binding motifs are of great interest, since this can lead to enhanced tumor specificity and avidity.

Photodynamic therapy (PDT) is a ternary treatment for cancer involving a photosensitizer, tissue oxygen, and light (often using lasers). PDT can be used as treatment for basal cell carcinoma (BCC) or lung cancer; PDT can also be useful in removing traces of malignant tissue after surgical removal of large tumors.

Cancer immunotherapy refers to a diverse set of therapeutic strategies designed to induce the patient's own immune system to fight the tumor. Contemporary methods for generating an immune response against tumours include intravesical BCG immunotherapy for superficial bladder cancer, and use of interferons and other cytokines to induce an immune response in renal cell carcinoma and melanoma patients. Vaccines to generate specific immune responses are the subject of intensive research for a number of tumours, notably malignant melanoma and renal cell carcinoma. Sipuleucel-T is a vaccine-like strategy in late clinical trials for prostate cancer in which dendritic cells from the patient are loaded with prostatic acid phosphatase peptides to induce a specific immune response against prostate-derived cells.

Allogeneic hematopoietic stem cell transplantation ("bone marrow transplantation" from a genetically non-identical donor) can be considered a form of immunotherapy, since the donor's immune cells will often attack the tumor in a phenomenon known as graft-versus-tumor effect. For this reason, allogeneic HSCT leads to a higher cure rate than autologous transplantation for several cancer types, although the side effects are also more severe.

The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial.

Angiogenesis inhibitors prevent the extensive growth of blood vessels (angiogenesis) that tumors require to survive. Some, such as bevacizumab, have been approved and are in clinical use. One of the main problems with anti-angiogenesis drugs is that many factors stimulate blood vessel growth, in normal cells and cancer. Anti-angiogenesis drugs only target one factor, so the other factors continue to stimulate blood vessel growth. Other problems include route of administration, maintenance of stability and activity and targeting at the tumor vasculature.

Risk. The present invention also contemplates treating individuals at risk for any of the aforementioned disease states. These individuals would include those persons suffering from conditions discussed above.

IV. Kits

Any of the compositions described herein may be comprised in a kit. In a non-limiting example, an individual miRNA agonist/antagonists (e.g., expression construct, antagomir, LNA) is included in a kit. The kit may also include one or more transfection reagent(s) to facilitate delivery of the agonist/antagonist to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution. A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the manipulation or characterization of miRNA.

V. Vectors for Cloning, Gene Transfer and Expression

Within certain embodiments expression vectors are employed to express nucleic acid agonist/antagonists, such as miRs, antisense molecules. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" is meant to include any type of genetic construct containing a nucleic acid coding for a gene product in which part or all of the nucleic acid encoding sequence is capable of being transcribed. Generally, the nucleic acid encoding a gene product is under transcriptional control of a promoter.

A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al; 1990 |
| Immunoglobulin Light Chain | Queen et al., 1983; Picard et al., 1984 |
| T-Cell Receptor | Luria et al., 1987; Winoto et al., 1989; Redondo et al; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |

TABLE 1-continued

Promoter and/or Enhancer

| Promoter/Enhancer | References |
|---|---|
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α1-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrook et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villareal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987. |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

C. Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990). Defective hepatitis B viruses also are useful as expression vectors (Horwich et al., 1990).

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the eye, liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

VI. Definitions

The term "treatment" or grammatical equivalents encompasses the improvement and/or reversal of the symptoms of disease. "Improvement in the physiologic function" of the eye may be assessed using any of the measurements described herein.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the terms "antagonist" and "inhibitor" refer to molecules, compounds, or nucleic acids that inhibit the action of a factor. Antagonists may or may not be homologous to these natural compounds in respect to conformation, charge or other characteristics. Antagonists may have allosteric effects that prevent the action of an agonist. Alternatively, antagonists may prevent the function of the agonist. Antagonists and inhibitors may include proteins, nucleic acids, carbohydrates, small molecule pharmaceuticals or any other molecules that bind or interact with a receptor, molecule, and/or pathway of interest.

As used herein, the term "agonist" refers to molecules or compounds that mimic or promote the action of a "native" or "natural" compound. Agonists may be homologous to these natural compounds in respect to conformation, charge or other characteristics. Agonists may include proteins, nucleic acids, carbohydrates, small molecule pharmaceuticals or any other molecules that interact with a molecule, receptor, and/or pathway of interest.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

LNA-anti-miRs, pre-miR Precursors, siRNAs and miRNA Expressing Adenoviruses.

LNA-anti-miRs for miR-23a/b, miR-27a/b, or scramble controls for in vitro and in vivo studies were synthesized from Exiqon. LNA-anti-miR-27a/b sequence for in vitro use is: 5'-GAACTTAGCCACTGTGAA-3' (SEQ ID NO: 20)

(Product #: 500150, Batch #: 604052). LNA-anti-miR-23a/b sequence for in vitro use is: 5'-AATCCCTGGCAATGT-GAT-3' (SEQ ID NO: 21) (Product #: 500150, Batch #: 604053). LNA-scramble control sequence for in vitro use is: 5'-GTGTAACACGTCTATACGCCCA-3' (SEQ ID NO: 22) (Product #: 199004-00, Batch #: 205157). LNA-anti-miR-27a/b sequence for in vivo use is: 5'-ACTTAGCCACT-GTGA-3' (SEQ ID NO: 23) (Product #: 500150, Batch #: 603226). LNA-anti-miR-23a/b sequence for in vivo use is: 5'-TCCCTGGCAATGTGA-3' (SEQ ID NO: 24) (Product #: 500150, Batch #: 603227). LNA-scramble control sequence for in vivo use is: 5'-ACGTCTATACGCCCA-3' (SEQ ID NO: 25) (Product #: 500150, Batch #: 603228). LNA-anti-miRs were typically transfected at a final concentration of 50 nM using Lipofectamine 2000 (Invitrogen) as transfection reagent. SiRNAs for SPROUTY2 were synthesized from Dharmacon. The target sequence for human SPROUTY2 siRNA is 5'-GCAGGUACAUGUCUUGUCU-3' (SEQ ID NO: 26). Ambion Pre-miR™ miRNA precursor of hsa-miR-23b, hsa-miR-27b, or negative control was synthesized from Applied Biosystem. Adenovirus expressing miR-23b, miR-27b or lacZ was generated from mouse genomic DNA encoding miR-23b or -27 as described (Wang et al., 2008a).

Cell Culture, Cell Proliferation, Scratch-Wound, In Vitro Matrigel and Aortic Ring Sprouting Assays.

HUVEC (ATCC) cells were grown in EC growth medium (EGM) (Lonza). SEMA6A recombinant protein was obtained from R&D. For VEGF treatment, HUVECs were starved with EC basal medium (EBM-2) with 0.1% FBS for 24 hours, and then treated with VEGF (20 ng/ml) for the indicated periods of time. For LPS treatment, HUVECs were treated with LPS (100 ng/mL) for the indicated periods of time without starvation. Adenovirus infection, siRNA, Pre-miR™-miRNA precursor or LNA-anti-miR transfection in cell culture and aortic ring culture was performed as described (Wang et al., 2008b). EC cell proliferation and scratch-wound assays were performed using HUVEC cells as described (Wang et al., 2008a; Lee et al., 2006). For cellular proliferation assay, about 2×10³ transfected HUVECs were seeded in 24-well plates. After starvation with 0.1% serum for overnight, the cells were stimulated with 20 ng/ml VEGF-A for 20 hours and then subjected to BrDU labeling for 4 hours. DNA synthesis as determined by BrDU incorporation was quantified using a commercial ELISA kit from Roche (Penzberg, Germany) according to the manufacturer's instructions. For wound scratch assay, scratch wound was made using a 200 μL pipette tip in LNA anti-miR transfected HUVEC monolayer before VEGF (20 ng/ml) stimulation. 1 μM of 5-fluouracil (5-FU, sigma) was added to the cell right after wound scratch to block cell proliferation. Post scratch EC migration was scored at 14 hrs after wound scratch. In vitro angiogenesis assays were performed as described (Chang et al., 2006). Briefly, 3 days after LNA anti-miR transfection with Liptofectamine Plus reagent (Invitrogen), cells were harvested either for RNA analysis or in vitro angiogenesis. Matrigel was purchased from Chemicon, and the assays were performed according to manufacture manual. Briefly, HUVECs were transfected with anti-miR or scramble control using lipofectamine 2000, and cultured for 48 hrs, serum starved overnight, then trypsinized and used for Matrigel assay. Quantification of branch points per field (20×) was done on 6 fields and 6 sample repeats.

RNA, Western Blot Analysis and Reporter Assay.

Total RNA was isolated from mouse tissues or cell lines using TRIzol reagent (Invitrogen). Northern blots to detect microRNAs were performed as described (Wang et al., 2008b). Real-time RT-PCR using Sybergreen probes was performed using 1 ug of RNA as a template with random hexamer primers to generate cDNA. miRNA real-time RT-PCR was performed using miRCURY LNA™ Universal microRNA RT-PCR system (Exiqon). For PCR and cloning of miR-23~27~24 pri-miRNAs, Race-Ready cDNA from mouse embryos (Ambion) was used. Sequences of PCR primers for SPROUTY2, SPROUTY2 (miR-23m), SPROUTY2 (miR-27m), SEMA6D 3'UTRs, as well as mouse miR-23a~27a~24-2 and miR-23b~27b~24-1 pri-miRNA, are listed as follows:

(1) hSPROUTY2-3'UTR (SacI):
(SEQ ID NO: 7)
5'-atcg gagctc AGCAACACAGACACTCCTAGGCA-3'

(2) hSPROUTY2-3'UTR (hindIII):
(SEQ ID NO: 8)
5'-atcg aagctt GCATCTGTAACCCCTCATTTGCAGC-3'

(3) hSPROUTY2 (miR-27mut) up:
(SEQ ID NO: 9)
5'-caataatatttgcacagactccaaacaagttgtgc-3'

(4) hSPROUTY2 (miR-27mut) dn:
(SEQ ID NO: 10)
5'-gcacaacttgtttggagtctgtgcaaatattattg-3'

(5) hSPROUTY2 (miR-23mut1) up:
(SEQ ID NO: 11)
5'-gtacattcggaagccgacagatcaatcagtatg-3'

(6) hSPROUTY2 (miR-23mut1) dn:
(SEQ ID NO: 12)
5'-catactgattgatctgtcggcttccgaatgtac-3'

(7) hSPROUTY2 (miR-23mut2)dn:
(SEQ ID NO: 13)
5'-atcgaagcttgcatctgtaacccctcatttgcagcaactcgagtcgc ctcataaaaggggc-3'

(8) hSEMA6D-3'UTR (SacI):
(SEQ ID NO: 14)
5'-atcggagctcCCCACTGGGGCGAAGGTGGA-3'

(9) hSEMA6D-3'UTR (HindIII):
(SEQ ID NO: 15)
5'-atcgaagcttAGGGTTGCGCATCATCAGCCGT-3'

(10) mPri-miR-23a~27a~24-2 (up):
(SEQ ID NO: 16)
5'-CTGGTGCATTCGGAAACCTTGTGT-3'

(11) mPri-miR-23a~27a~24-2 (dn):
(SEQ ID NO: 17)
5'-ATTGGAGCATTCTTGCTTGCCTGC-3'

(12) mPri-miR-23b~27b~24-1 (up):
(SEQ ID NO: 18)
5'-ATGAAAGAGACGCACTAGCCCACA-3'

(13) mPri-miR-23b~27b~24-1 (dn):
(SEQ ID NO: 19)
5'-TTGGGTTCCTGGCATGCTGATTTG-3'

For Western blot analysis, protein lysates were resolved by SDS-PAGE and blotted using standard procedures. Antibodies used were as follows: ERK1/2 (Cell signaling), Phospho-ERK1/2 (Cell signaling), Phospho-AKT (Cell signaling), SPROUTY2 (Abcam), SEMA6A (R&D), SEMA6D (R&D), and GAPDH (Abcam) as loading control. Band intensity was quantified using NIH ImageJ software and normalized to correspondent GAPDH signal. For reporter assay, the 3' UTR of SPROUTY2 or SEMA6D was inserted into the pMIR-REPORT vector (Ambion). SEMA6A 3' UTR construct was purchased from Genecopeia. SPROUTY2 3' UTRs with mutations in the region complementary to the miR-23 or miR-27 seed regions were generated by mutagenesis. Pre-miR™ miRNA precursors (ABI) were cotransfected with the UTR plasmids indicated into COS-7 cells. Reporter assays were performed as described (Chang et al., 2005).

Neonatal Retinal Injection and Postnatal Retinal Angiogenesis.

In vivo injection in the mouse retina was performed primarily as described (Matsuda et al., 2004). Briefly, 1 µL of 5 mg/mL solution of LNA-anti-miR23 and miR-27 or LNA-scramble control was unilaterally injected intravitreously into the retina of postnatal day (P)$_2$ mice in the ICR background. Mice were allowed to develop for RNA, protein isolation and histological analyses at P6. Visualization of the vasculature was performed by Alexa-594 conjugated isolectin B4 (Molecular Probes) or ICAM-2 staining of retinal flat mounts. Quantification of vessel density was performed using NIH ImageJ software. The radial length of the vascular network was calculated by measuring the distance from the optic disc to the periphery of the vascular plexus. Student's t tests were used to determine statistical significance between groups.

Laser-Induced CNV.

Laser photocoagulation was induced in 6-8 week-old male C57BL/6J mice as described (To be et al, 1998). Briefly, the pupils of anesthetized animals were dilated with 1% tropicamide (Alcon Laboratories Inc., Forth Worth, Tex.). Three 532-nm diode laser spots (140 mW, 100 msec, 100 µm; OcuLight GL Photocoagulator, Iridex) were applied to each fundus of adult mice using a coverslip as a contact lens. Six laser spots were applied when the samples were used for RNA isolation. Formation of a bubble at the time of laser application indicates rupture of Bruch's membrane and successful laser injury. Animals were injected intravitreously with 1 µl of 5 mg/mL solution of LNA-anti-miR23/27, LNA-scramble or PBS injection control after laser photocoagulation. A secondary injection was adopted on the next day to ensure maximal knockdown of miR-23/27. The retina/choroid/sclera complexes from the treated eyes were collected 7 days after laser injury for fluorescein angiography, RNA and protein analyses. At 14 days after laser injury, the eyes were fixed in 4% paraformaldehyde for 30 minutes at room temperature. The retina/choroid/sclera complexes were then dissected, and fixed for frozen section or flat-mount staining. For flatmount staining, the samples were post-fixed for 1 hour, incubated with blocking buffer (PBS with 0.5% Triton X-100 and 5% goat serum), and stained with ICAM-2 antibody at 4° C. overnight. After washing and secondary antibody staining, the samples were flat mounted on glass slides. Images of CNV were captured using a Leica SP2 multi-photon Laser Scanning confocal microscope, and CNV volume was quantified using NIH ImageJ software. Student's t tests were used to determine statistical significance between groups.

Institutional Compliance and Animal Care.

All experiments using animals were approved by the Institutional Animal Care and Use Committee at University of Texas Southwestern Medical Center.

Example 2

Results

Structure and Expression Pattern of miR-23~27~24 Cluster Members.

Figure 1A:
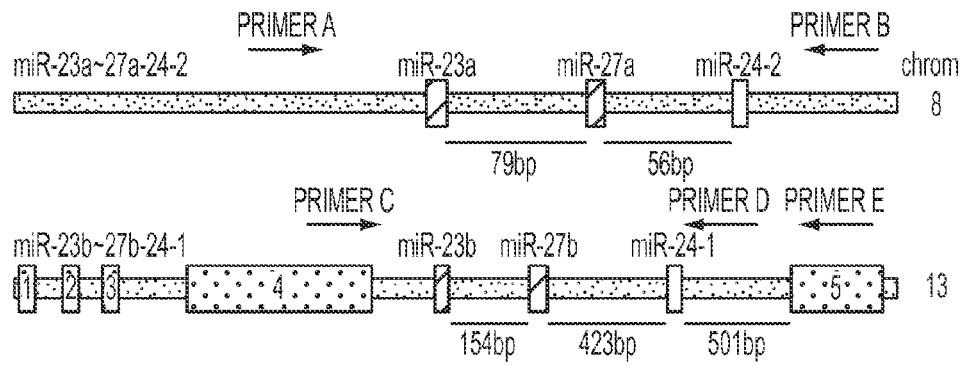
FIGS. 1A-C. Gene structure and expression pattern of miR-23~27~24 clusters.
Figure 7C:
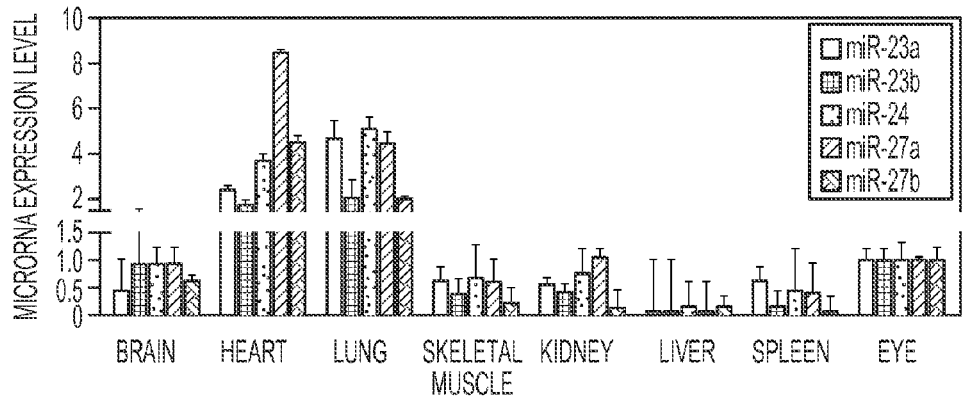

The mouse miR-23a~27a~24-2 cluster is intergenic on chromosome 8, and the miR-23b~27b~24-1 cluster is located in intron 4 of an alanine aminopeptidase gene on chromosome 13 (FIG. 1A). The miR-23a~27a~24-2 cluster encodes a pri-miRNA transcript composed of 3 miRNAs: miR-23a, miR-27a and miR-24-2, while the miR-23b~27b~24-1 cluster encodes a pri-miRNA transcript containing miR-23b, miR-27b and miR-24-1 (FIG. 7A). The mature miRNA sequences of miR-23a/b, miR-27a/b and miR-24 are conserved among vertebrate species (FIG. 7B). miR-23a and miR-27a differ by only one nucleotide near their 3' ends compared to their paralogs miR-23b and miR-27b, while the sequence of miR-24-1 and miR-24-2 is the same (FIG. 7C). miR-23a and miR-23b share most, if not all, predicted target genes by TargetScan and DIANA Lab, as do miR-27a and miR-27b (Friedman et al., 2009; Maragkakis et al., 2009).

Figure 1B:
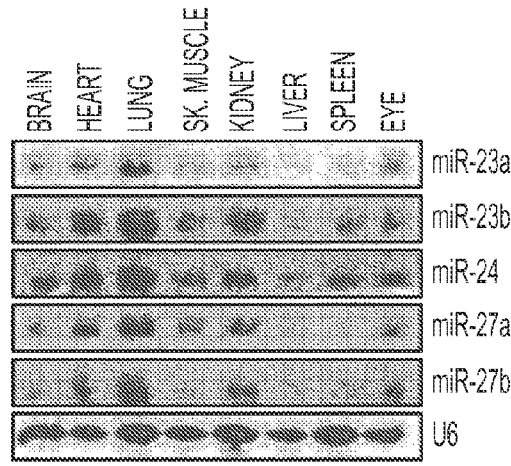
Figure 1C:
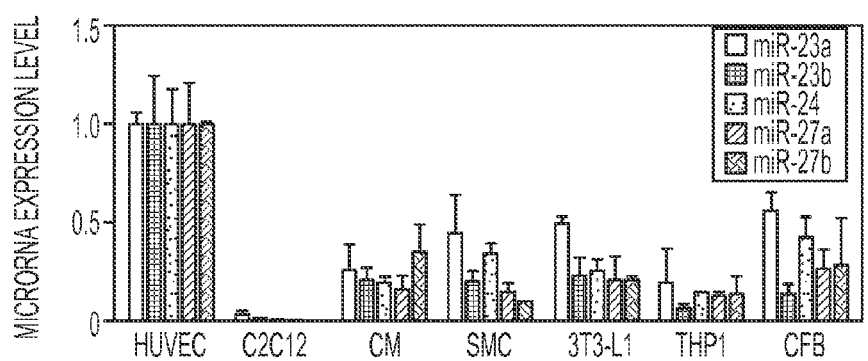
Figure 7D:
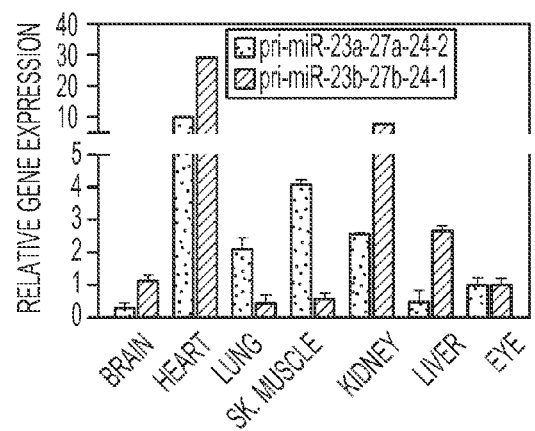

Northern blot analyses revealed that miR-23a/b, miR-27a/b and miR-24 are expressed at highest levels in the lung and heart, which are highly vascularized tissues (FIG. 1B). Their expression is also detectable in other organs, including the eye. Real-time PCR confirmed the enrichment of the mature miRNAs of these two clusters in the lung and heart (FIG. 7D). ECs compared to other cell types (FIG. 1C), consistent with previous reports (Poliseno et al., 2006; Suarez et al., 2007; Kuehbacher et al., 2007; Harris et al., 2008; Chhabra et al., 2010; Friedman et al., 2009; Maragkakis et al., 2009; Axton et al., 2008) and a recent report that miR-23~27b~24-1 host gene is enriched in ECs in vivo (Axton et al., 2008). Taken together, these results indicate that miR-23~27~24 cluster members are enriched in ECs and highly vascularized tissues, suggesting a potential role in EC function.

Modulation of Sprouting Angiogenesis by miR-23 and miR-27 In Vitro.

Figure 2A:
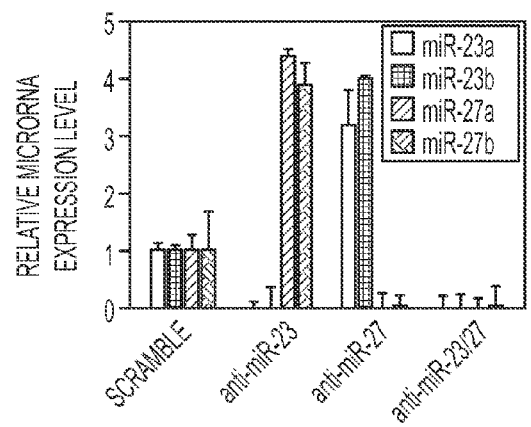
FIGS. 2A-F. Regulation of angiogenesis by miR-23 and miR-27 in vitro and ex vivo.
Figure 2B:
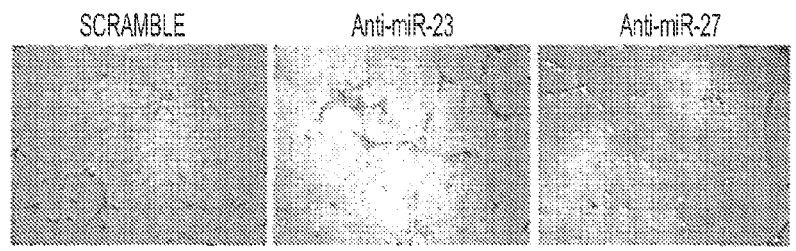
Figure 2C:
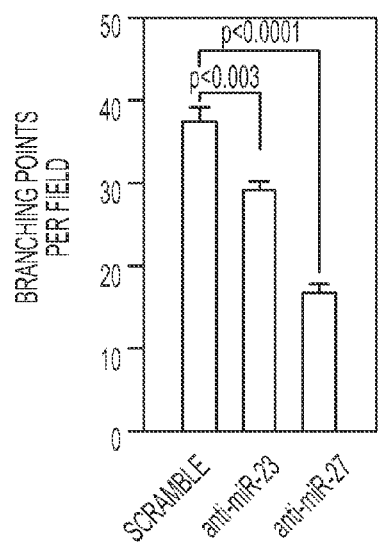

To study the EC function of miR-23~27~24 cluster members in vitro, HUVECs were transfected with Locked Nucleic Acid (LNA)-modified anti-miRs of miR-23a/b, miR-27a/b, or a scramble control, and tested for EC network formation on Matrigel. More than 90% knockdown of miR-23a/b or miR-27a/b expression was achieved by LNA-anti-miR-23a/b or anti-miR-27a/b transfection, respectively, indicating the efficiency and specificity of miRNA knockdown by LNA anti-miRs (FIG. 2A). Hereafter, miR-23a/b and miR-27a/b will be referred to as miR-23 and miR-27. Of note, there was compensatory up-regulation of miR-23 or miR-27 when miR-27 or miR-23 were knocked down. When cultured on Matrigel, ECs form a primary vascular network. Knockdown of miR-27, and to a lesser extent miR-23, impaired the formation of capillary-like structures in HUVECs cultured on Matrigel, as quantified by the reduced branching points upon miR-27 or miR-23 inhibition (FIGS. 2B-C). These results suggest that miR-27 and miR-23 are required for proper capillary tube formation in vitro.

Figure 2D:
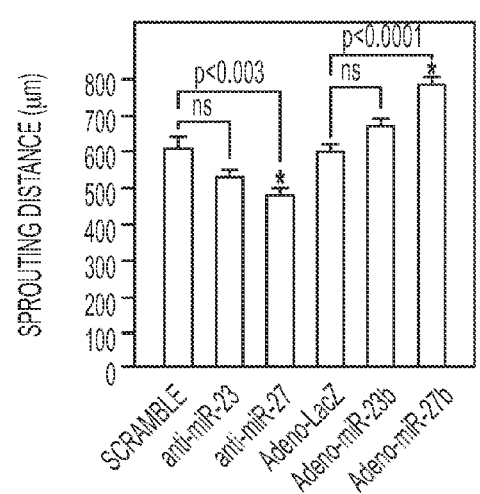

An ex vivo aortic ring assay was performed to further explore the requirement of miR-23 and miR-27 in sprouting angiogenesis (Wang et al., 2008a). Isolated aortic rings were transfected with anti-miR-23, anti-miR-27, or scramble control, and cultured on Matrigel with endothelial growth medium supplemented with 3% mouse serum. Normally EC sprouts appear on the second day from the aortic rings and grow rapidly after 4 to 6 days of culture. Compared to the control, knockdown of miR-27, and to a lesser extent miR-23, significantly repressed the outgrowth of aortic ring cells (FIG. 2D).

To further determine whether over-expression of miR-23 or miR-27 is sufficient to enhance sprouting angiogenesis, similar assays were performed after infection of the aortic rings with adenoviruses expressing miR-23b, miR-27b or LacZ control. Compared to the LacZ control, over-expression of miR-27 significantly enhanced aortic ring cell outgrowth, causing an ~30% increase in migratory distance, while miR-23 over-expression also showed a trend toward increased aortic ring cell sprouting (FIG. 2D, and FIG. 8).

Figure 2E:
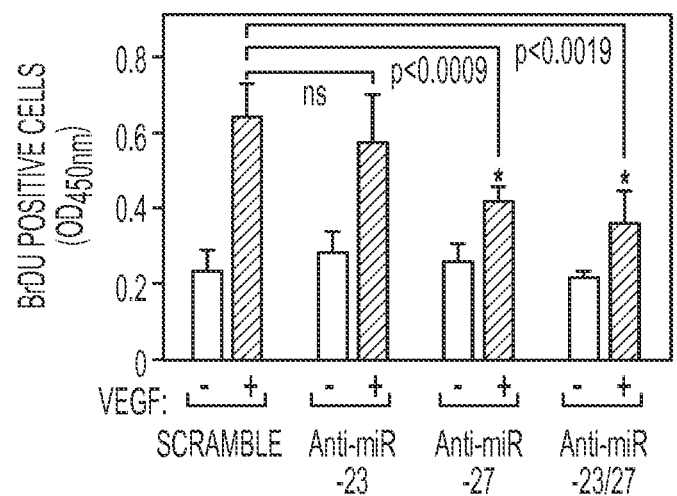
Figure 2F:
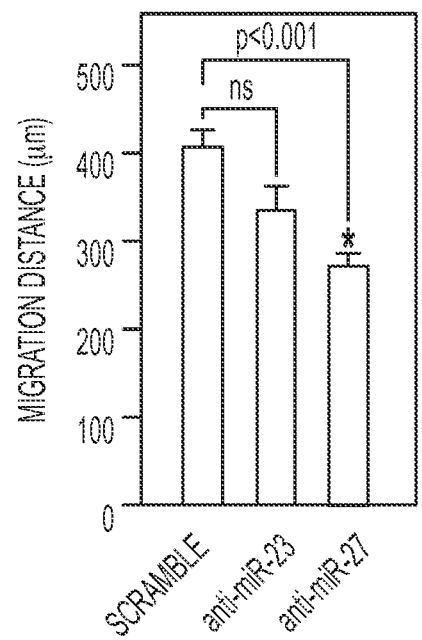

To examine the cellular mechanism whereby miR-23 and miR-27 regulate angiogenesis, EC proliferation and migration were analyzed after LNA-anti-miR-23/27 transfection. EC proliferation upon VEGF stimulation was measured by BrDU incorporation, while EC migration was quantified after a scratch wound assay (Lee et al., 2006; Wang et al., 2008b). As shown in FIG. 2E, compared to serum-starved HUVECs, VEGF induced EC proliferation by about 3-fold in 24 hrs. Knockdown of miR-27 repressed VEGF-induced EC proliferation by ~30%, while knockdown of miR-23 also showed a trend in repressing EC proliferation. Knockdown of both miR-23 and miR-27 appeared to have a synergistic effect in repressing VEGF-induced EC proliferation. When a scratch wound is created in a monolayer of cultured HUVECs, the cells migrate to the wounded region upon stimulation by VEGF. VEGF-induced EC migration was significantly repressed by miR-27 silencing, and to a lesser extent by miR-23 silencing in ECs (FIG. 2F). These results indicate that miR-23 and miR-27 enhance angiogenesis by promoting EC proliferation and migration in response to VEGF.

miR-23 and miR-27 Target Sprouty2, Sema6A and Sema6D in ECs.

To begin to elucidate the mechanisms whereby miR-23 and miR-27 regulate angiogenesis, the inventors took a bioinformatic approach to identify signaling pathways and target genes regulated by miR-23 and miR-27. Using the Diana-mirPath software, designed to integrate miRNA target genes into signaling pathways (Papadopoulos et al., 2009), the inventors found that proteins involved in axon guidance (P=0.00018) and MAPK signaling pathways (P=0.034) were significantly enriched in miR-23 and miR-27 target genes (FIG. 9A). Among the predicted target genes, the inventors focused on Sprouty2, Semaphorin6A (Sema6A) and Semaphorin6D (Sema6D), which negatively regulate angiogenesis (Impagnatiello et al., 2001; Dhanabal et al., 2005). Importantly, multiple conserved binding sites for miR-23a/b and miR-27a/b are contained in the 3'UTRs of these mRNAs (FIG. 9B), suggesting that miR-23 and miR-27 might promote angiogenesis through suppression of Sprouty2, Sema6A and Sema6D, which exert anti-angiogenic activity.

Figure 3A:
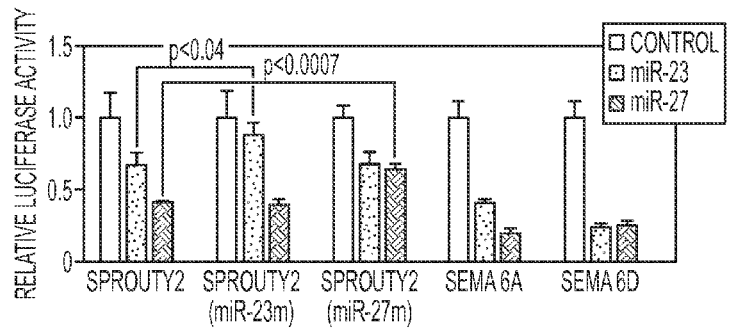
FIGS. 3A-G. Regulation of angiogenic signaling by miRs-23 and miR-27.

To test whether miR-23 and miR-27 directly inhibit Sprouty2, Sema6A and Sema6D 3'UTR activity, the inventors tested the effects of these miRNAs on expression of luciferase reporters linked to the 3'UTRs of Sprouty2, SEM6D, and SEMA6A mRNAs in COS cells. Overexpression of miR-23 or miR-27 significantly repressed the activity of luciferase reporters containing human SPROUTY2, SEMA6A or SEMA6D 3'UTRs (FIG. 3A). Moreover, the repression of the SPROUTY2 3'UTR by miR-23 and miR-27 was dependent on their targeting sites, since mutation of either the miR-23 target sites or the miR-27 target site in the SPROUTY2 3' UTR attenuated the repression by miR-23 or miR-27, respectively (FIG. 3A).

Figure 3B:
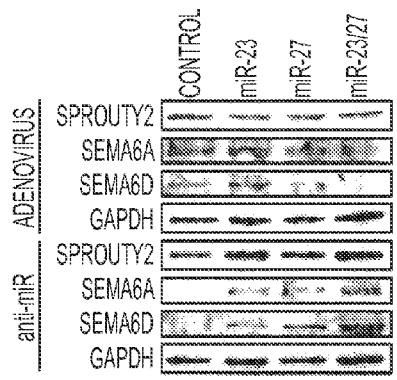

To examine whether miR-23 and miR-27 could repress the expression of endogenous SPROUTY2, SEMA6A or SEMA6D proteins, HUVECs were infected with adenovirus expressing miR-23b and/or miR-27b, or LacZ as control, and SPROUTY2, SEMA6A or SEMA6D protein expression was examined by Western blot. As shown in FIG. 3B, over-expression of miR-23b or miR-27b repressed SPROUTY2, SEMA6A and SEMA6D expression, while over-expression of miR-23b and miR-27b showed a synergistic effect in repressing the expression of these proteins.

Next, the inventors transfected HUVECs with LNA-anti-miRs of miR-23 and/or miR-27, or scramble control, and examined the expression of these proteins similarly. The inventors observed a significant increase in the expression of SPROUTY2 SEMA6A and SEMA6D expression upon miR-23 or miR-27 knockdown (FIG. 3B). These results indicate that miR-23 and miR-27 mediate the repression of SPROUTY2, SEMA6A and SEMA6D expression in ECs.

Figure 3C:
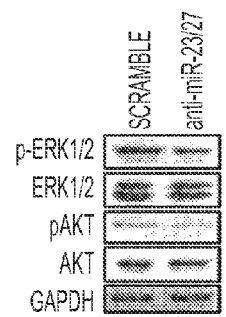
Figure 3D:
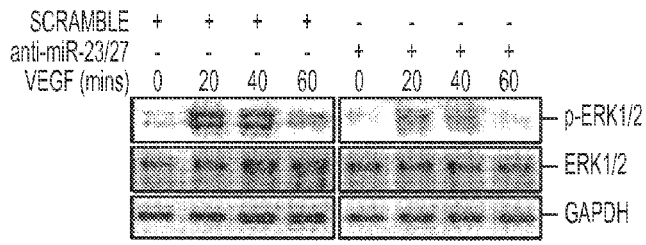
Figure 3E:
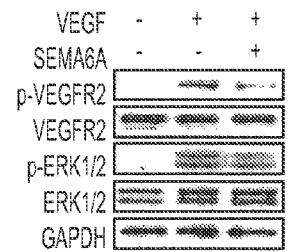

Sprouty proteins function as intracellular inhibitors of the Ras/Raf/ERK pathway (Casci et al., 1999). Semaphorin proteins can provide directional cues for cell migration by modulating VEGF signaling pathways (Dhanabal et al., 2005; Toyofuku et al., 2004). To test whether miR-23 and miR-27 are required for regulating angiogenic signaling pathways, HUVECs were transfected with LNA-anti-miR-23/27 or scramble control, and phospho-AKT and phospho-ERK1/2, indicative of AKT and MAP kinase activities, were measured. Phosphorylation of ERK1/2 and AKT was significantly decreased by miR-23 and miR-27 knockdown in ECs without affecting total ERK1/2 and AKT levels (FIG. 3C). Anti-miR-23/27 or control transfected HUVECs were further tested for ERK1/2 phosphorylation in response to VEGF. As shown in FIG. 3D, ERK1/2 phosphorylation was strongly induced in HUVECs upon VEGF treatment. Knockdown of miR-23 and miR-27 repressed ERK1/2 phosphorylation induced by VEGF, consistent with the upregulation of the miR-23/27 target protein SPROUTY2, which inhibits the RAS/RAF/ERK pathway. SEMA6A inhibits EC migration (Dhanabal et al., 2005). To test whether the upregulation of SEMA6A contributes to the decreased angiogenic signaling upon miR-23/27 knockdown, HUVECs were incubated with SEMA6A recombinant protein, treated with VEGF, and tested for angiogenic signaling activities. As shown in FIG. 3E, SEMA6A significantly repressed the phosphorylation of VEGFR2 and ERK1/2 in response to VEGF, while VEGFR2 and ERK1/2 proteins remained unchanged. These results support the conclusion that miR-23 and miR-27 are required for modulating VEGFR2 and MAPK signaling in response to VEGF through repressing SPROUTY2 and possibly SEMA6A.

Figure 3F:
Figure 3G:
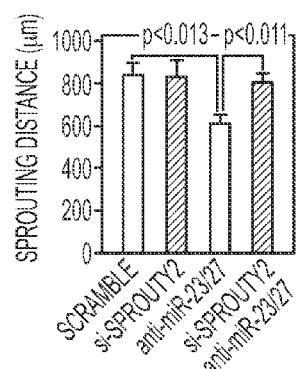

The inventors further asked whether Sprouty2 can mediate the angiogenic effects of miR-23 and 27. Aortic ring assays were performed to examine whether knockdown of Sprouty2 by siRNA could rescue the sprouting defects caused by miR-23/27 silencing. Western blot analysis confirmed the efficient Sprouty2 knockdown in the cultured aortic rings (FIG. 3F). The results showed that Sprouty2 knockdown rescued the sprouting defects caused by miR-23/27 silencing, indicating that Sprouty2 plays a major role in mediating miR-23/27 angiogenic effects (FIG. 3G, and FIG. 10).

Regulation of Retinal Vascular Development by miR-23 and miR-27 In Vivo.

Figure 4A:
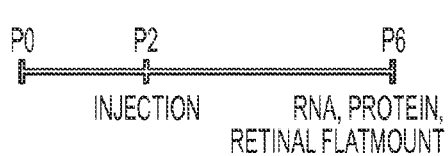
FIGS. 4A-E. Regulation of retinal vascular development by miRs-23 and miR-27.
Figure 4B:
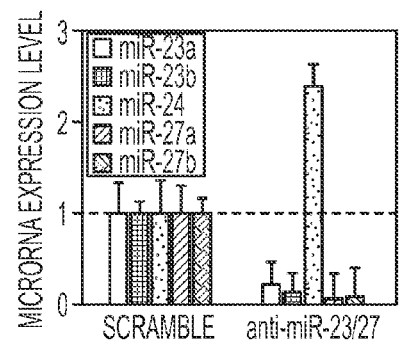

To further address the role of miR-23 and miR-27 in angiogenesis in vivo, the inventors performed miRNA loss-of-function studies in neonatal mouse retinas, a well established model of angiogenesis (Stahl et al., 2010). Vascularization of the outer retina commences at postnatal day 0 (P0) from the central retinal artery, and the ECs sprout to reach the peripheral region at about P8. Anti-miRs targeting miR-23 and miR-27, or scramble control, were injected subretinally into the eye at P2, and retinas were isolated at P6 for RNA, protein, and flat mount staining of the developing retinal vasculature (FIG. 4A). Subretinal injection of LNA-anti-miR-23/27 resulted in more than 90% reduction in retinal miR-23/27 levels compared to the controls (FIG. 4B). Of note, compensatory up-regulation of miR-24 was observed (FIG. 4B). Thus, LNA-anti-miRs displayed high efficacy and specificity in the retina in vivo.

Figure 4C:
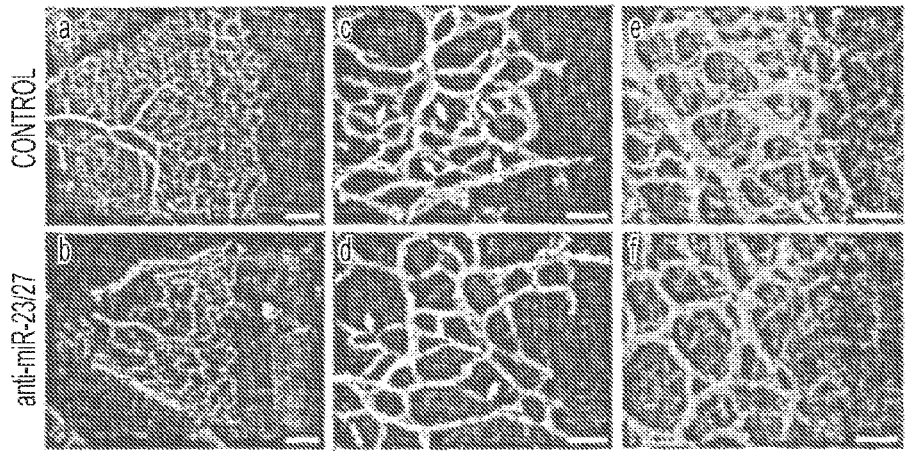
Figure 4D:
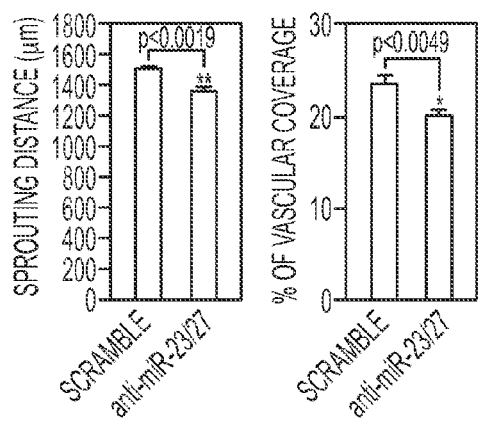
Figure 4E:
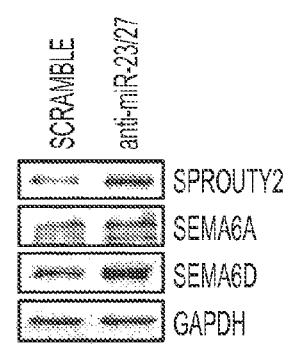

To examine the effect of miR-23/27 knockdown on postnatal retinal vascular development, P6 retinal flat mounts were stained with ICAM-2 to visualize the vessels. Scramble LNAs did not affect retinal vascular development compared to the non-injection controls based on ICAM-2 staining. However, in anti-miR-23/27 injected retinas, there was an ~10% decrease in sprouting distance and an ~20% decrease in vascular coverage at 4 days after anti-miR-23/27 injection compared to the controls (FIGS. 4C-D). At higher magnification, fewer newly formed vessel sprouts were observed in the anti-miR-23/27 injected retinas compared to the controls (FIG. 4C, panels c and d). During retinal vascular development, ECs sprout along GFAP-positive astrocytes. GFAP staining indicated that astrocyte coverage was not affected by miR-23/27 knockdown (FIG. 4C, panels e and f), suggesting that the retinal EC sprouting phenotype by miR-23/27 knockdown is not secondary to potential astrocyte defects. Moreover, consistent with the inventors' in vitro results, miR-23 and miR-27 target proteins, Sprouty2, Sema6A and Sema6D, were significantly upregulated upon miR-23/27 knockdown in the retinas (FIG. 4E). Taken together, these results indicate that miR-23 and miR-27 modulate retinal vascular development in vivo.

Requirement of miR-23 and miR-27 in Choroidal Neovascularization In Vivo.

The angiogenic defects resulting from miR-23 and miR-27 knockdown in vitro and in vivo suggested that miR-23 and miR-27 might play an important role in neovascularization in response to injury. The inventors adopted a laser-induced CNV mouse model, the most reliable CNV animal model, to test the role of miR-23 and miR-27 in CNV (Ryan, 1982). They first examined the expression of miR-23~27~24 clusters in the retina/choroid after laser injury. Adult C57BL/6 mice were subjected to rupture of Bruch's membrane in 6 locations by laser photocoagulation (140 mV, 100 mSec, 100 µm) (To be et al., 1998). As demonstrated by real-time PCR, miR-23a, miR-27a and miR-24 levels were significantly upregulated, while miR-23b and miR-27b expression was also increased in the retinal/choroidal region at 1 week after laser injury (FIG. 5A).

To directly test the requirement of miR-23/27 in CNV, LNA-anti-miRs targeting miR-23 and miR-27, or scramble control, were injected intravitreously to knockdown miR-23 and miR-27 in the eye immediately following laser injury in 3 locations (FIG. 5B). A secondary injection was performed on the following day to ensure efficient knockdown. Eyes were collected at 2 weeks after laser injury for ICAM-2 staining and confocal imaging (Campa et al., 2008). As shown in FIG. 5C, more than 90% knockdown efficiency of miR-23 and miR-27 in the retina/choroid/sclera was achieved by anti-miR injection compared to the controls. Of note, the inventors observed an up-regulation of miR-23~27~24 members after scramble control injection compared to non-injection controls, possibly reflecting the increased inflammatory response due to injection. The inventors tested anti-PECAM-1 antibody, Isolectin-B4 and FITC-Dextran staining besides anti-ICAM-2 staining, and found ICAM-2 gave the best staining for CNV, consistent with a recent report (Campa et al., 2008). Quantification of CNV area, as shown by ICAM-2 staining, revealed that silencing of miR-23 and miR-27 repressed CNV area by more than 50% compared to scramble control (FIGS. 5D-F). The repression of CNV by miR-23/27 was also confirmed by ICAM-2 staining of the lesion sections (FIG. 5E). Compared to the non-injection controls, the inventors observed a mild increase in CNV in scramble injected samples, possibly due to increased CNV induced by miR-23~27~24 up-regulation (FIG. 11B). Taken together, these data indicate that miR-23 and miR-27 are required for laser induced CNV in vivo.

miR-24 Targets Multiple Proteins Involved in Cytoskeleton Actin Dynamics.

In an effort to explore the function and underlying mechanisms of miR-24, the inventors utilized DIANA-mirPath software to search predicted target genes and signal pathways regulated by miR-24. Among the pathways predicted, actin cytoskeleton dynamics was ranked as one of the top pathways regulated by miR-24. Multiple proteins involved in regulating actin turnover downstream of Rho signaling, including DIAPH1, p21-activated kinase PAK4 and LIMK2, were predicted to be miR-24 targets. As shown in FIG. 12A, the 3'-untranslated region (3'-UTR) of these genes contain sequences complementary to the miR-24 seed region, which are highly conserved among multiple species. To examine whether miR-24 regulates the expression of these target proteins in vitro, human umbilical vein endothelial cells (HUVECs) were transfected with miR-24 mimics or locked-nucleic acid (LNA) modified miR-24 anti-miR, and tested for DIAPH1, PAK4 and LIMK2 expression by Western blot analyses. Overexpression of miR-24 markedly repressed DIAP1, PAK4 and LIMK2 protein expression, while silencing of miR-24 by LNA-antimiR led to increased expression of DIAPH1 and LIMK2 (FIG. 12B). Interestingly PAK4 expression was not affected by miR-24 silencing, suggesting additional regulatory mechanism of PAK4 in addition to miR-24. PAK4-LIMK2 signaling has been shown to phosphorylate and inactivate another cytoskeletal regulatory protein, cofilin, thereby inhibiting cofilin's actin depolymerization activity. To further dissect whether the downregulation of PAK4 and LIMK4 by miR-24 leads to a decrease in Cofilin phosphorylation, phosphor-cofilin and total cofilin levels were examined by Western blot analyses upon miR-24 overexpression/knockdown. Consistently, miR-24 overexpression reduced the level of Cofilin phosphorylation, while miR-24 silencing led to an increase Cofilin phosphorylation level. The total Cofilin level seemed not changed by miR-24 overexpression/knockdown. PAK4-LIMK2-Cofilin pathway and its regulated stress fiber dynamics are required to sustain MAPkinase ERK1/2 activity. To further test whether ERK1/2 phosphorylation is regulated by miR-24, phosphor-ERK1/2 and total ERK1/2 levels are examined similarly. As expected, miR-24 overexpression decreased phosphor-ERK1/2 level, while miR-24 silencing had the opposite effect (FIG. 12C). The level of total ERK1/2 remained unchanged upon miR-24 overexpression/knockdown. Taken together, miR-24 are sufficient and necessary to regulate actin polymerization/depolymerization pathway by targeting key proteins involved in actin cytoskeleton dynamics in ECs.

Regulation of Actin Dynamics in ECs by miR-24 In Vitro.

DIAPH1 has been shown to promote actin polymerization through recruiting Profilin, while phosphorylation of Cofilin is known to block the function of Cofilin as an actin depolymerizing protein. To further test whether the downregulation of DIAPH1 and PAK4/LIMK2/Cofilin pathway by miR-24 leads to a defect in actin polymerization, the amount and distribution of filamentous F-actin versus monomeric G-actin and the number of stress fibres in ECs was visualized by labeling with phalloidin upon miR-24 overexpression/knockdown. Overexpression of miR-24 in HUVECs resulted in a loss of stress fibers as revealed by phalloidin staining (FIG. 13A). Most of the miR-24 overexpressed cells appeared much smaller and lost their polarity. However, silencing of miR-24 seemed not affecting the stress fiber amount and distribution under normal condition. To examine the formation of stress fibers are affected by miR-24, miR-24 mimic or antimiR transfected HUVECs were pretreated with Rho inhibitor Y-27632 to collapse the actin stress fibers for 1 hr. Normally actin stress fibers reappear after the remover of the Rho inhibitor Y-27632. However, in contrast to the control, in miR-24 tranfected HUVECs, stress fibers failed to reappear at 20 and 40 minutes after the remover of Y-27632 (FIG. 13B). Conversely, miR-24 silencing led to increased stress fiber formation at 20 minutes after the remover of Y-27632 compared to the control, suggesting that miR-24 knockdown promotes the formation of stress fiber formation.

Modulation of Angiogenesis by miR-24 In Vitro.

The actin cytoskeleton plays an essential role in the maintaining of normal function of the cell by modulating cell shape, migration and proliferation, the processes critical for angiogenesis. To study the function of miR-27 in angiogenesis, an in vitro Matrigel tube formation assay was performed in HUVECs transfected with miR-24 mimic or anti-miR. Under normal condition, when cultured on Matrigel for 6-8 hours, HUVECs forms a primary vascular network. Overexpression of miR-24 with miRNA mimics disrupted tube formation as quantified by the drastic reduced branching points, while silencing of miR-24 with LNA-antimiR mildly enhanced the formation of tubular structures (FIGS. 14A-B). To dissect the cellular mechanism whereby miR-24 regulates angiogenesis, a BrDU incorporation assay and a scratch wound assay were utilized to analyze EC proliferation and migration upon miR-24 overexpression. As shown in FIG. 14C, compared to the control, miR-24 overexpression blocked EC proliferation in normal EGM2 medium after overnight starvation. In the scratch wound cell migration assay, overexpression of miR-24 inhibited EC migration into the wounded region in HUVECs compared to the non-transfected and control mimic transfected cells (FIG. 14D).

To further investigate the role of miR-24 in sprouting angiogenesis, miR-24 mimic or anti-miRs was transfected into aortic ring segments in EGM2 medium, and the sprouting of aortic ring cells was quantified after an ex vivo aortic ring assay. As shown in FIGS. 14E-F, miR-24 overexpression significantly repressed the outgrowth of aortic ring cells at 6 days after culture, while silencing of miR-24 seemed not effective in regulating aortic ring cell outgrowth. These suggest that miR-24 is sufficient but not necessary in modulating sprouting angiogenesis in the ex vivo system.

Repression of CNV by miR-24 In Vivo.

The inventors' previous results have shown that miR-23~27~24 members were upregulated in the retina/choroid in a laser-induced CNV mouse model. To test whether miR-24 is sufficient to repress laser-induced neovascularization in the choroid, miR-24 mimic was injected intravitreously into the eye at 0, 4 and 9 days after laser injury, and CNV was quantified at 2 weeks post injury after ICAM-2 staining and confocal flat mount imaging. miR-24 mimic injection led to about 20-fold increase in miR-24 expression in the eye cup as detected by real-time RT-PCR (data not shown). Quantification of CNV area revealed that miR-24 overexpression led to about 50% decrease in the neovascularization of the choroid ($10726\pm1385$ $\mu m^2$, N=22 in saline control, verses $5612\pm1272$ $\mu m^2$, N=24 in miR-24 injected samples, FIG. 15C). Compared to the noninjection control, control mimic led to an insignificant increase in CNV (P=0.47). These results indicate that miR-24 is sufficient to repress CNV in vivo.

The inventors have previously shown that silencing of miR-23/27 represses angiogenesis and CNV in vivo. To test a potential combination effect of anti-miR-23/27 and miR-24 mimic in angiogenesis, EC proliferation and migration were quantified after anti-miR-23/27 and miR-24 mimic transfection. As shown in FIGS. 15A-B, compared to the anti-miR-23/27 and miR-24 mimic alone, triple miRNA mimic and anti-miRs cocktail showed superior effects in repressing EC proliferation and migration in vitro. The inventors observed 60% repression in EC proliferation and about 80% repression in EC migration with the triple miR treatment. To further examine the effect of the triple miR cocktail in laser-induced CNV in vivo, similar laser injury experiments as described above were performed, and CNV area was quantified after triple miR treatment. Compared to the saline control, triple miR treatment led to about 65% repression in CNV at 2 weeks after laser injury ($10726\pm1385$ $\mu m^2$, N=22 in saline control, versus $3920\pm1200$ $\mu m^2$, N=18; 1385 $\mu m^2$ in the triple miR injected samples). Taken together, these results indicate that miR-23/27 and miR-24 have distinct function in angiogenesis, and triple miR combination of miR-23/27 and miR-24 have superior effects in repressing CNV, pointing to a therapeutic potential for miRNA cocktails in wet AMD and other vascular diseases (FIG. 16, model).

Example 3

Discussion

Figure 6:
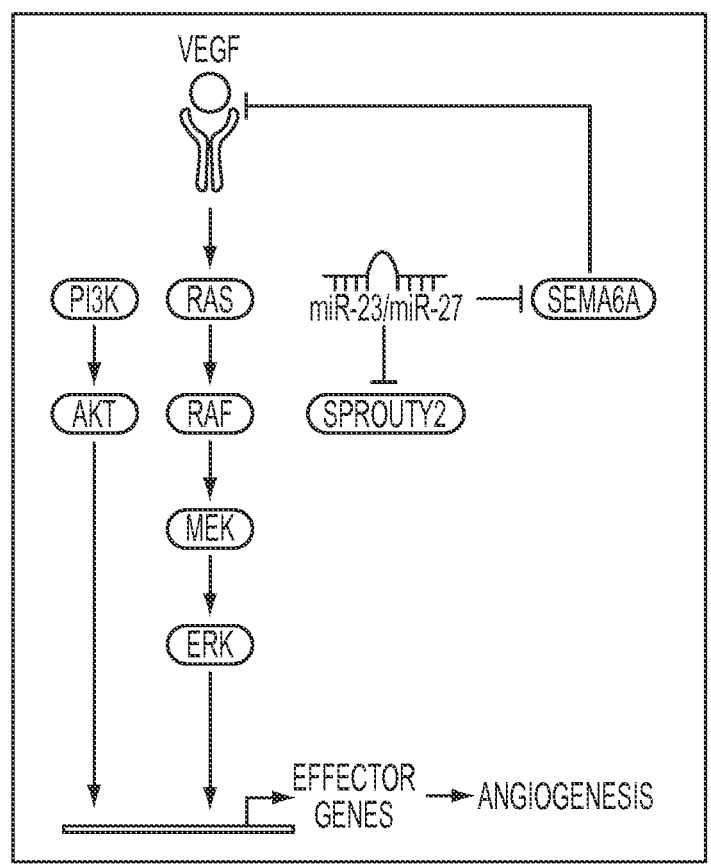
FIG. 6. A model for miRs-23/27 function in angiogenesis. VEGF binds to its receptors and activates MAP and PI3K-AKT kinase signaling pathway in ECs, which in turn stimulates the transcription of genes involved in angiogenesis. miRs-23/27 from the miR-23~27~24 families promote angiogenesis by repressing their target proteins Sprouty2 and SEMA6A, which negatively regulate Ras/MAP kinase signaling and VEGFR2 mediated signaling, respectively.

The findings of this study reveal an important role for miR-23 and miR-27 in angiogenesis and choroidal neovascularization (FIG. 6). The inventors provide evidence that silencing of miR-23 and miR-27 represses sprouting angiogenesis in vitro and in vivo, as well as CNV in a laser-induced CNV mouse model. The pro-angiogenic actions of miR-23 and miR-27 correlate with the repression of their target mRNAs encoding Sprouty2 and Sema6A, which negatively regulate MAP kinase and VEGFR2 signaling in response to angiogenic factors. Thus, in the absence of miR-23 and miR-27, Sprouty2 and Sema6A proteins are upregulated, with consequent dampening of MAP kinase and VEGFR2 signaling. Conversely, overexpression of miR-23 and miR-27 represses these targets, relieving their repressive influence on these pathways.

miR-23~27~24 Cluster Members in Angiogenesis.

These results are consistent with a recent report that silencing of miR-27b represses EC sprouting in vitro (Kuehbacher et al., 2007). The inventors' results extend those findings to demonstrate that miR-23 and miR-27 are required for proper angiogenesis in vitro and in vivo. The following observations support the inventors' conclusion: 1) miR-23 and miR-27 are enriched in ECs and highly vascularized tissues; 2) silencing of miR-23 or miR-27 in ECs impairs vascular network formation on Matrigel; 3) knockdown of miR-23 or miR-27 in cultured aortic rings represses EC outgrowth, while adenoviral overexpression of miR-23 or miR-27 enhances aortic ring EC sprouting; 4) knockdown of miR-23 or miR-27 represses EC proliferation and migration in response to VEGF; 5) silencing of miR-23 and miR-27 suppresses the sprouting of retinal vascular development in mice; and 6) silencing of miR-23 and miR-27 represses neovascularization of the choroid in response to laser injury. It seems that miR-27 has a more dominant role in angiogenesis than miR-23, as shown by more severe miR-27 knockdown/overexpression phenotypes in the Matrigel and aortic ring assays. miR-24 has been shown to regulate apoptosis and inhibit cell proliferation (Lal et al., 2009; Walker Harland, 2009). In the absence of miR-23 and miR-27, there is a compensatory up-regulation of miR-24 in the inventors' in vitro and in vivo knockdown assays (FIG. 4B). The potential role of miR-24 in angiogenesis awaits future studies.

Regulation of Angiogenic Signaling by miR-23 and miR-27.

The influence of miR-23 and miR-27 on angiogenesis can be attributed to their promotion of EC proliferation and migration in response to angiogenic factors. Consistent with this conclusion, knockdown of miR-23 and miR-27 represses MAP kinase signaling in response to VEGF, as shown by the repression of ERK1/2 phosphorylation. Phosphorylation of AKT is also repressed by miR-23 and miR-27 knockdown, which may result from the repression of VEGFR2 signaling by SEMA6A. Members of miRNA clusters have been proposed to function in combination (Yuan et al., 2009). Axon guidance and MAP kinase signaling are highly ranked as the biological processes regulated by both miR-23 and miR-27. It is noteworthy, in this regard, that axon guidance molecules commonly affect EC behavior similarly, accounting for the similar patterning of both blood vessels and nerves (Carmeliet & Tessier-Lavigne, 2005), while MAPK pathways have been shown to regulate angiogenesis. Among the predicted target genes in these pathways, Sprouty proteins function as intracellular inhibitors of the MAP kinase pathway. Sema6A has also been reported to repress angiogenic signaling Dhanabal et al., 2005). The inventors show that both miR-23 and miR-27 directly target the Sprouty2 and Sema6A 3'UTRs for repression. The identification of Sprouty2 as target for both miR-23 and miR-27 is consistent with a recent report that Sprouty2 is a target for miR-27a during cancer cell growth and migration (Ma et al., 2010). The inhibitory actions of Sprouty proteins are mediated by interference of phosphorylation and activation of Raf, an upstream activator of the MAP kinase pathway. Repression of Sprouty2 by miR-23 and miR-27 at least partially underlies the mechanism whereby miR-23 and miR-27 enhance MAP kinase pathway activation in response to VEGF. SEMA6A may also contribute to the regulation of MAPK and PI3K-AKT signaling by miR-23 and miR-27, likely through repressing VEGFR2 signaling. Knockdown of Sprouty2 rescued the sprouting defects imposed by miR-23/27 silencing in cultured aortic rings, indicating a major role for Sprouty2 in mediating miR-23/27 angiogenic function. Since miR-23 and miR-27 have hundreds of predicted target genes, the angiogenic function of miR-23 and miR-27 likely reflects the combined effects of multiple target genes.

miR-23~27~24 Cluster Members in CNV.

Inflammation and angiogenesis play pivotal roles in CNV, the major cause of vision loss in patients with AMD (Bressler, 2009; Augustin & Kirchhof, 2009). These results show that miR-23~27~24 cluster members are upregulated in CNV (FIG. 6A). This correlates with the up-regulation of miR-23~27~24 cluster members by pro-inflammatory stimuli LPS (Jennewein et al., 2010; Zhou et al., 2009, and FIG. 11A), suggesting a role for miR-23~27~24 cluster members in linking inflammation to angiogenesis in CNV. Consistently, miR-27b was recently shown to contribute to LPS-mediated inflammation by targeting PPAR-γ (Jennerwein et al., 2010). The inventors' finding that silencing of miR-23 and miR-27 represses laser-induced CNV indicates that miR-23~27~24 cluster members indeed play a causative role in CNV. However, how miR-23, 27 and miR-24 regulate inflammation in CNV is yet to be investigated. Since miR-23~27~24 clusters are highly conserved from mice to humans, therapeutic manipulation of miR-23/27 represents a potential strategy in treating CNV in patients with neovascular AMD and other vascular diseases. The identification of miR-23 and miR-27 as important regulators of MAPK activation also suggests roles for these miRNAs in cancer.

miR-24 Contribution to Endothelial Cell Activity and CNV.

The function of miR-23~27~24 family member miR-24 in angiogenesis and CNV has been largely unclear. Whether miR-24 and miR-23/27 have combinational effects in CNV is totally unknown. The inventors now provide evidence that miR-24 regulates actin dynamics in endothelial cells (ECs) through targeting multiple members downstream of Rho signaling, including Pak4, Limk2 and mDiaph1 proteins. Overexpression of miR-24 in ECs blocks stress fiber formation, represses EC migration, proliferation and tube formation in vitro, as well as angiogenesis in an ex vivo aortic ring assay. Moreover, overexpression of miR-24 by miRNA represses laser-induced CNV in vivo. Additionally, miR-23/27 anti-miRs and miR-24 show synergistic effect in repressing EC proliferation and migration in vitro, as well as laser-induced CNV in vivo. Together with the inventors' previous results, these findings suggest that miR-23/27 and miR-24 have distinct functions in angiogenesis. Antagonism of miR-23/27 function, and miR-24 agonism, may achieve superior outcome in regulating angiogenesis than individual miRNAs, and therefore represents an attractive therapeutic target for treatment of wet AMD and other vascular diseases.

Example 4

Materials and Methods

Animals.

Animal studies were conducted in accordance with the ARVO statement for the Use of Animals in Ophthalmic and Vision Research and were approved by the Institutional Animal Care and Use Committees at the University of Texas Southwestern Medical Center and Tulane University. C57BL/6 male mice (6 to 8 weeks of age) were used for the studies in laser-induced CNV. For generation of miR-24 transgenic (TG) mice, human miR-24-1 DNA was PCR amplified, digested with PstI, and cloned into CAG-Z-GFP vector to generate CAG-Z-miR-24-GFP. The primers for miR-24 are:

```
                                        (SEQ ID NO: 27)
5'-atcgctgcagCGCGGTGAACTCTCTCTTGT-3'
and (SEQ ID NO: 28)
5'-atcgctgcagCCCAGCTCTCCTGAGCCT-3'.
```

The construct was then released with SpeI/AflII before transgenic injection. After confirmation of germline transmission, the founder mice were crossed with CAG-Cre mice to generate miR-24TG mice. Genotyping of the miR-24TG mice was performed using PCR primers:

```
                                        (SEQ ID NO: 29)
5'-ATCGGTCGACCGCGGTGAACTCTC-3'
and (SEQ ID NO: 30)
5'-ATCGGTCGACCCCAGCTCTCCTGAG-3'.
```

Laser-Induced CNV and Retinal Vasculature Staining.

Laser-induced CNV was induced in 6-8 week-old male C57BL/6J mice. Briefly, the pupils of anesthetized animals were dilated with 1% tropicamide (Alcon Laboratories Inc., Forth Worth, Tex.). Three 532-nm diode laser spots (140 mW, 100 msec, 100 µm; OcuLight GL Photocoagulator, Iridex) were applied to each fundus of adult mice using a coverslip as a contact lens. Formation of a bubble at the time of laser application indicates rupture of Bruch membrane and successful laser injury. Animals were injected subretinally with 1 µL of 200 ng/µl solution of miR-24 mimic or scramble control, or PBS, after laser photocoagulation. Two more injections were performed at day 5 and 10 after injury. For visualizing the distribution of miRNA mimics, FAM-labeled miRNA was delivered at 7 days after laser injury, and the injected eyes were collected for flatmount imaging at 4 days after. At 14 days after laser injury, the treated eyes were fixed in 4% paraformaldehyde, and subjected to flatmount ICAM-2 staining. For visualization of the retinal vasculature, retinas were dissected from pups or adult mice, and stained with Alexa-594 conjugated isolectin B4 (Molecular Probes) or ICAM-2. Images of CNV were captured using a Leica SP2 multi-photon Laser Scanning confocal microscope, and CNV volume were quantified using NIH ImageJ software.

miRNA Mimics, LNA-Anti-miRs, siRNAs.

LNA-anti-miRs for miR-24 or scramble controls for in vitro were synthesized from Exiqon. miR-24 or control pre-miR precursor for in vitro study were synthesized from Ambion, while miR-24 or control mimic for in vivo studies were synthesized from Shanghai GenePharma Co. Sequence for control LNA-anti-miR is 5'-GTGTAACACGTC-TATACGCCCA-3' (SEQ ID NO: 22). Sequence for miR-24 LNAantimiR is 5'-CUGUUCCUGCUGAACUGAGCCA-3' (SEQ ID NO: 31). Sequences for control mimic are:

```
sense-
                                       (SEQ ID NO: 32)
5'-p-fUsfUfCfUfCfCGAAfCGfUGfUfCAfCsGfUsTsT-3'
and antisense-
                                       (SEQ ID NO: 33)
5'-ChoIsAsfCGfUGAfCAfCGfUfUfCGGAGAAsTsT-3'.
```

(f: 2'-deoxy-2'-fluoro nucleotides, Chol: cholesterol, p: phosphate group, s: phosphorothioate linkages). Sequences for miR-24 mimic are:

```
sense-
                                       (SEQ ID NO: 34)
5'-p-fUsGGfCfUfCAGfUfUfCAGfCAGGAAfCsAsG-3'
and antisense-
                                       (SEQ ID NO: 35)
5'-ChoIsGsfUfUfCfCfUGfCfUGAAfCfUGAGfCfCAsfUsfU-3'.
``` siRNAs for LIMKJ, LIMK2, PAK4, DIAPH1 and COFILIN were synthesized from Sigma. The sequences are as follows:

```
human LIMK1 siRNA:
                                       (SEQ ID NO: 36)
5'-CUCUGAGUCCCUCCGCGUA[dT][dT]-3';

human LIMK2 siRNA:
                                       (SEQ ID NO: 37)
5'-GCUUCUUUGGGCAGGCUAU[dT][dT]-3';

human PAK4 siRNA:
                                       (SEQ ID NO: 38)
5'-GGCUGAAGCUGUCAGA CUU[dT][dT]-3';
```

```
human DIAPH1 siRNA:
                                       (SEQ ID NO: 39)
5'-CAUGUGAGGAGUUACGUAA[dT][dT]-3';

human COFILIN siRNA:
                                       (SEQ ID NO: 40)
5'-CCUCUAUGAUGCAACCUAU[dT][dT]-3'.
```

Plasmid Construction and Reporter Assay.

3'-UTRs of miR-24 target genes were PCR amplified from human placenta race-ready cDNAs (Ambion), and cloned into pmiR-REPORT vector (Applied Biosystems). The sequences for UTR cloning are:

```
LIMK2,
                                       (SEQ ID NO: 41)
5'-atcggccggcAGGAGGCAAGTGGGCGCAGC-3'
and (SEQ ID NO: 42)
5'-atcggtttaaacGGCCCAGTTCAGGCCCACCA-3';

PAK4,
                                       (SEQ ID NO: 43)
5'-atcggagctcCTGGGGGTAGATGAGACCCTACT-3'
and (SEQ ID NO: 44)
5'-atcgaagcttCTGGTTCTTCAGGCAGTGGTT-3';

DIAPH1,
                                       (SEQ ID NO: 45)
5'-atcgactagtGTGACCGCGGCAGCTCCTCA-3'
and (SEQ ID NO: 46)
5'-atcggtttaaacTGGGCCAAGCCCAAGAGTGCC-3';

EZH2,
                                       (SEQ ID NO: 47)
5'-atcggagctcTTCCCCTTCTCTCTGAAACAGC-3'
and (SEQ ID NO: 48)
5'-atcgaagcttCAACAAGTTCAAGTATTCTTTATTCAA-3'.
```

Reporter assays to test UTR activities were performed.

Cell Culture and Aortic Ring Assay.

HUVEC (ATCC) cells were grown in EC growth medium (EGM) (Lonza). For VEGF treatment, HUVECs were starved with EC basal medium (EBM-2) with 0.1% FBS for overnight, and then treated with VEGF for the indicated periods of time. miRNA premiR/mimic or LNA-anti-miR transfection in cell culture and aortic ring culture were performed. For visualizing actin fiber in cells, ECs were fixed with 4% paraformaldehyde, and stained with 50 mg/ml FITC-labeled phalloidin (Sigma) at RT for 1 hour. For ROCK inhibitor treatment, HUVECs were pretreated with Y-27632 (10 µM). The inhibitor was washed away at 1 hour after, and the cells were subjected to phalloidin staining at indicated time points.

RNA and Western Blot Analysis.

Total RNA was isolated from mouse tissues or cell lines using TRIzol reagent (Invitrogen). Northern blots to detect miRNA level were performed using Starfire probes. miRNA real-time RTPCR was performed using qScript™ cDNA Synthesis and microRNA Quantification System (Quanta Biosciences). For Western blot analysis, protein lysates were resolved by SDS-PAGE and blotted using standard procedures. Antibodies used were as follows: mDIA1 (Thermo), LIMK1 (Cell signaling), LIMK2 (Cell signaling), PAK4 (Cell signaling), Cofilin (Sigma), phosphor-Cofilin (Sigma), ERK1/2 (Cell signaling), Phospho-ERK1/2 (Cell signaling), and GAPDH (Millipore) as loading control.

In Vitro Matrigel Assay, Cell Proliferation, Scratch-Wound Assay and Cell Death Assay.

In Vitro Matrigel Assay, cell proliferation and scratch-wound assay were performed. Cell death was performed by TUNEL staining using the In Situ Cell Death Detection kit and an Annexin V cell death kit (Invitrogen) according to the manufacturer's protocol.

Living Cell Time-Lapse Imaging and Analysis.

For live cell imaging, HUVECs were transfected with control and miR-24 mimic in 35 mm glass bottom dish (MatTek). Scratch wound was generated using 200 µl pipette tip 3 days later. Cells were then cultured in a stage-top incubator built on a Zeiss Axio observer microscope, which maintains 37° C. temperature and 5% $CO_2$ level. Images were acquired every 5 minutes for 6 hours using 20× objective on the microscope. Time-lapse images were converted to AVI movies using image J (NIH).

Statistics.

Each experiment was repeated at least three times. Student's T-tests were used to determine statistical significance between groups. P-values of less than 0.05 were considered to be statistically significant.

Example 5

Results miR-24 Targets Multiple Proteins Involved in the Actin Cytoskeleton Pathway.

Figures 17A, 17B:
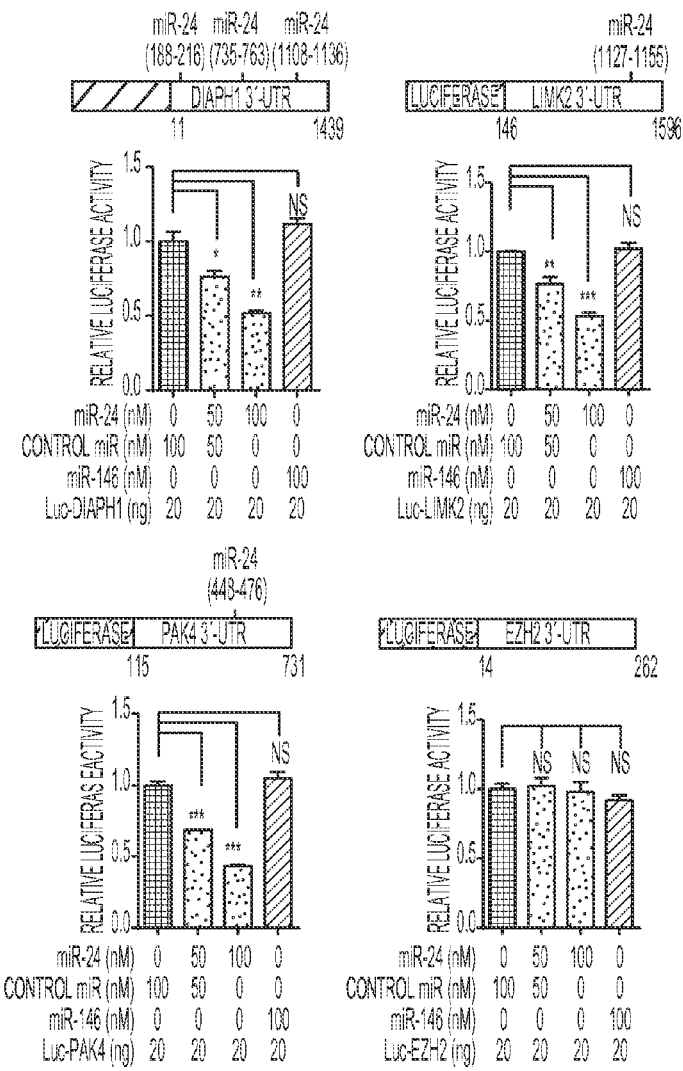
Figure 17D:
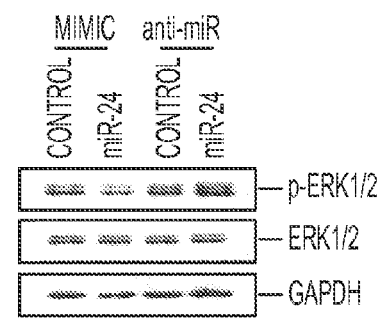
Figure 17C:
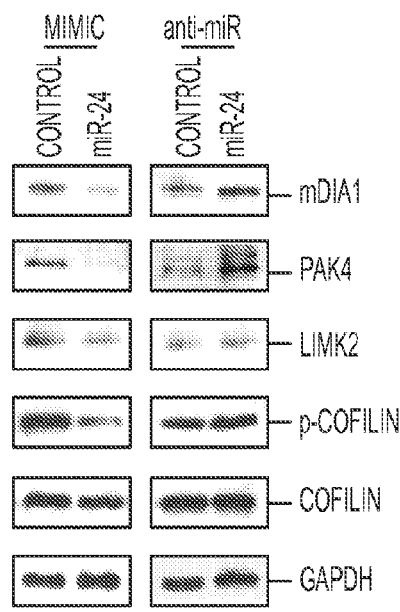

To begin to explore the function and underlying mechanisms of miR-24, the inventors utilized DIANA-mirPath software (Version 1) to search predicted target genes and signal pathways regulated by miR-24. Pathways involved in axon guidance, focal adhesion and actin cytoskeleton dynamics were ranked as among the top pathways regulated by miR-24. Multiple proteins involved in regulating actin dynamics downstream of Rho signaling, including DIAPH1, PAK4 and LIMK2, were predicted to be miR-24 targets. Among these, PAK4 and LIMK2 are also involved in axon guidance and focal adhesion. As shown in FIG. 17A, the 3'-untranslated region (3'-UTR) of these genes contain sequences complementary to the miR-24 seed region, which are highly conserved among multiple species. To test whether miR-24 represses the 3'-UTR activity of the predicted target genes, the 3'-UTRs of the three genes were fused downstream of the coding region of luciferase in a reporter vector, respectively. Each reporter was then cotransfected with a miR-24 mimic, a random control mimic, or a non-related miR-146 mimic in COS-1 cells. miR-24 mimic cotransfection resulted in a dose-dependent decrease in luciferase activity of the DIAPH1, LIMK2 and PAK4 3'-UTR reporters compared to the random control (FIG. 17B). miR-146, which is not predicted to target these three 3'-UTRs, failed to repress the luciferase activity of the 3'-UTR reporters, suggesting the specificity of repression by miR-24 in the target 3'-UTRs. To rule out that miR-24 nonspecifically represses the activity of nonrelated 3'-UTRs, the inventors also tested the effect on the activity of an EZH2 3'-UTR fragment, which does not contain miR-24 targeting site. They found that miR-24 has no effect on EZH2 3'UTR activity as revealed by luciferase assay. To further examine whether miR-24 regulates the expression of these target proteins in vitro, human umbilical vein endothelial cells (HUVECs) were transfected with miR-24 mimics or locked-nucleic acid (LNA) modified miR-24 anti-miR, and tested for DIAPH1, PAK4 and LIMK2 expression by Western blot analyses. Transfection of miR-24 mimic led to ~50-fold increase in miR-24 expression, while miR-24 anti-miR transfection resulted in ~90% miR-24 knockdown, indicating the efficiency of miR-24 overexpression/silencing. Of note, the expression of miR-23~27~24 family members miR-23a/b and miR-27a/b was not affected by either miR-24 mimic or antimiR. Overexpression of miR-24 markedly repressed DIAPH1, PAK4 and LIMK2 protein expression, while silencing of miR-24 by LNA-anti-miR led to increased expression of DIAPH1, PAK4 and LIMK2 (FIG. 17C). PAK4-LIMK2 signaling has been shown to phosphorylate and inactivate cytoskeletal regulatory protein Cofilin, thereby inhibiting the activity of Cofilin in actin depolymerization. To further dissect whether the downregulation of PAK4 and LIMK4 by miR-24 leads to a decrease in Cofilin phosphorylation, phospho-cofilin and total cofilin levels were examined by Western blot analyses upon miR-24 overexpression/knockdown. Consistently, miR-24 overexpression reduced the level of Cofilin phosphorylation, while miR-24 silencing led to a mild increase in Cofilin phosphorylation level. The total Cofilin level remained unchanged by miR-24 overexpression/knockdown. The PAK4-LIMK2-Cofilin pathway and its regulated stress fiber dynamics are required to sustain MAPkinase ERK1/2 activity. Specifically, PAK4 has been show to phosphorylate and cooperate with RAF to activate the ERK pathway. To further test whether ERK1/2 phosphorylation is regulated by miR-24, phospho-ERK1/2 and total ERK1/2 levels were measured. As expected, miR-24 overexpression decreased phospho-ERK1/2 levels stimulated by VEGF, while miR-24 silencing had the opposite effect (FIG. 17D). The level of total ERK1/2 was not changed by miR-24 overexpression/knockdown. Taken together, miR-24 is sufficient and necessary to regulate the actin polymerization/depolymerization pathway by targeting key proteins involved in actin cytoskeleton dynamics in ECs.

Regulation of Actin Cytoskeleton Dynamics in ECs by miR-24 In Vitro.

DIAPH1 has been shown to promote actin polymerization through recruiting Profilin, while phosphorylation of Cofilin by PAK4/LIMK2 is known to block the function of Cofilin as an actin depolymerizing protein. To further examine whether downregulation of DIAPH1 and PAK4/LIMK2/Cofilin pathway by miR-24 leads to a defect in actin polymerization, the amount and distribution of filamentous F-actin and the number of stress fibres in ECs were visualized by labeling with phalloidin upon miR-24 overexpression/silencing. Overexpression of miR-24 in HUVECs resulted in a loss of stress fibers as revealed by phalloidin staining (FIG. 18A). The miR-24 overexpressed cells appeared smaller, rounder, and contained a prominent band of polymerized actin around the cell periphery. However, silencing of miR-24 did not appear to affect the stress fiber amount and distribution under normal conditions. To examine whether the formation of stress fibers are affected by miR-24, miR-24 mimic or anti-miR transfected HUVECs were pretreated for 1 hour with Y-27632 (10 µM), a Rock inhibitor, to collapse the actin stress fibers. Normally actin stress fibers reappear after the removal of the ROCK inhibitor Y-27632. However, in contrast to the control, in miR-24 transfected HUVECs, stress fibers failed to reappear at 20 and 40 minutes after the removal of Y-27632 (FIG. 18B). Conversely, compared to the control, miR-24 silencing appeared to cause a slight increase stress fiber formation at 20 minutes after inhibitor removal, indicating that miR-24 knockdown enhances the formation of stress fiber formation.

Regulation of Angiogenesis by miR-24 In Vitro and Ex Vivo.

Figure 19A:
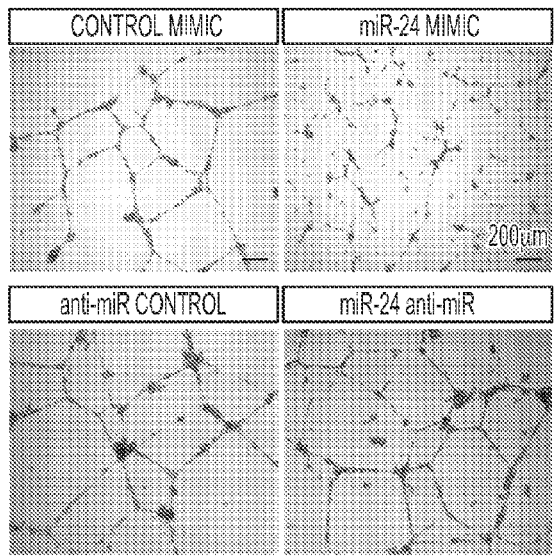
Figure 19B:
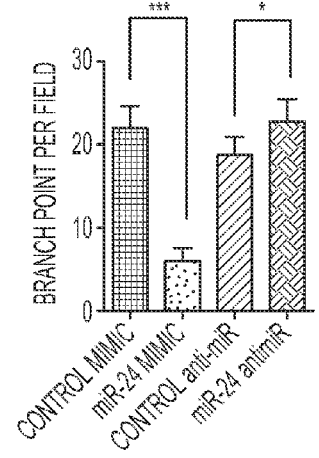
Figure 19C:
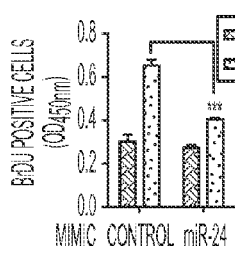
Figure 19D:
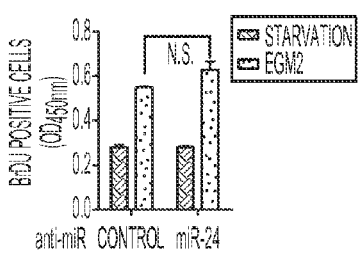
Figure 19E:
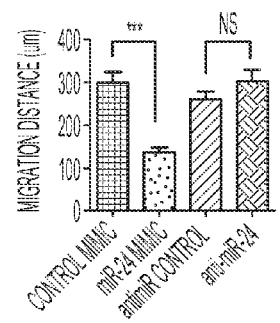
Figure 19F:
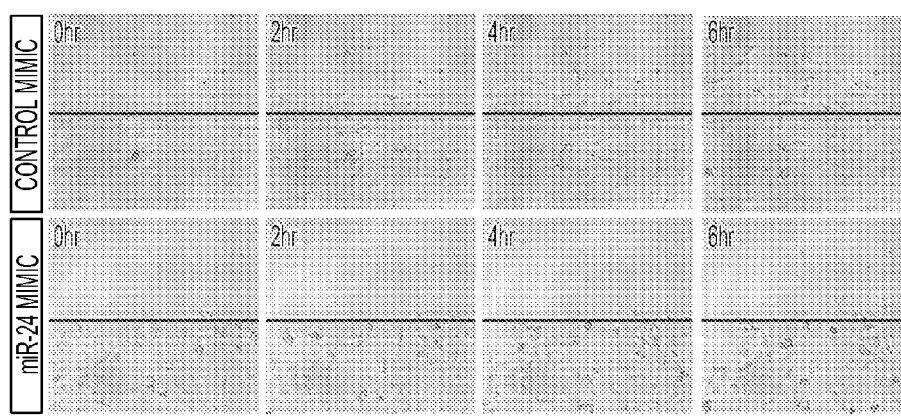

The actin cytoskeleton plays an essential role in maintaining the normal function of the cell by modulating cell shape, migration and proliferation, which are processes critical for angiogenesis. To study the function of miR-24 in angiogenesis, an in vitro Matrigel tube formation assay was performed in HUVECs transfected with miR-24 mimic or anti-miR. Under normal conditions, when cultured on Matrigel for 6-8 hours, HUVECs form a primary vascular tubular network. Overexpression of miR-24 with miRNA mimics disrupted tube formation as quantified by drastically reduced number of branch points, while silencing of miR-24 with LNAanti-miR mildly enhanced the formation of tubular structures (FIGS. 19A-B). To dissect the cellular mechanism whereby miR-24 regulates angiogenesis, a BrDU incorporation assay and a scratch wound assay were utilized to analyze EC proliferation and migration upon miR-24 overexpression. As shown in FIGS. 19C-D, compared to the control, miR-24 overexpression strongly repressed EC proliferation in EGM2 medium after overnight starvation, while silencing of miR-24 with LNA-anti-miR only slightly increased EC proliferation. In a scratch wound cell migration assay, overexpression of miR-24 inhibited EC migration into the wound region in HUVECs compared to the non-transfection and mimic control cells, while LNA-miR-24 antimiR showed a trend to increase EC migration (FIG. 19E). The effect of miR-24 on EC migration was also visualized for 6 hours by time-course live cell imaging (FIG. 19F). Compared to the massive lamellipodia formation and active migration in control cells, miR-24 overexpressed ECs had many fewer lamellipodia protrusions and remained stagnant.

Figure 19G:
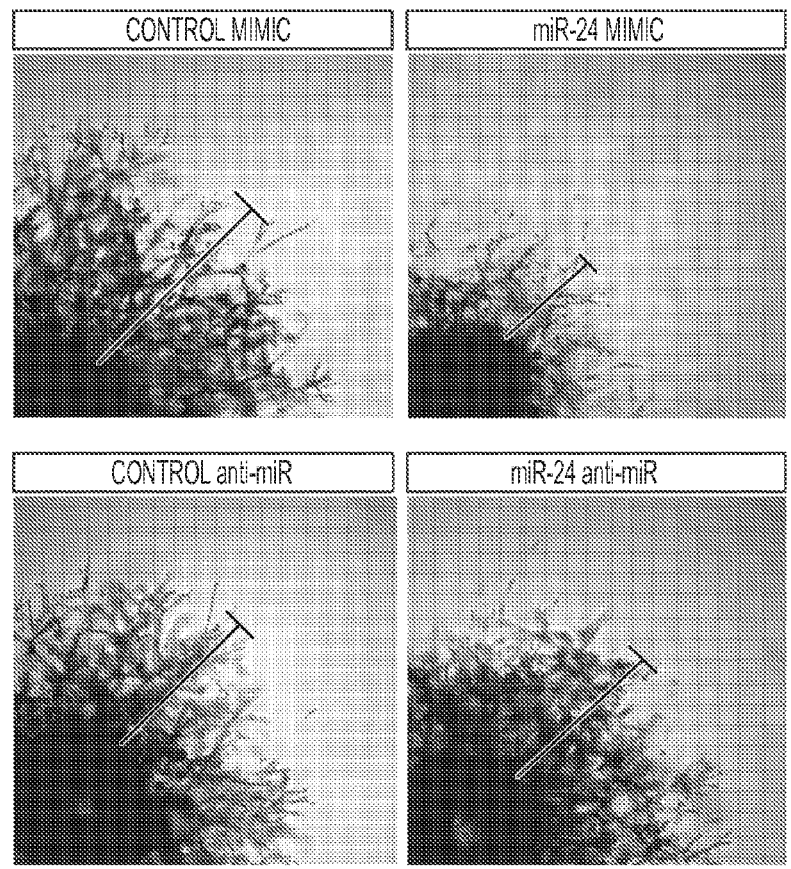
Figure 19H:
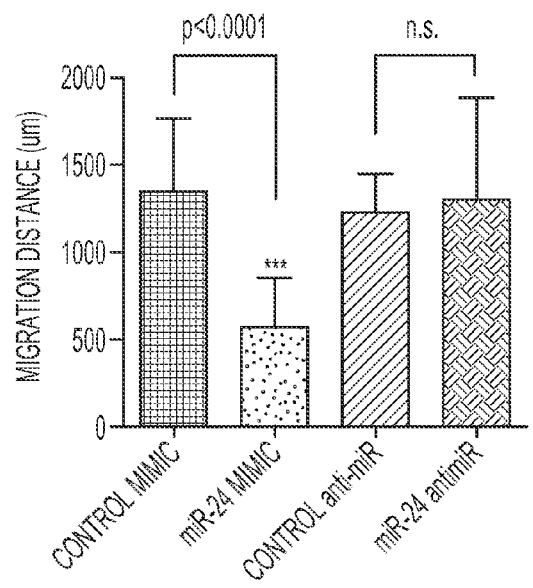

To further investigate the role of miR-24 in sprouting angiogenesis, miR-24 mimic or anti-miR was transfected into aortic ring segments in EGM2 medium, and the sprouting of aortic ring cells was quantified after an ex vivo aortic ring assay. As shown in FIGS. 19G-H, miR-24 overexpression significantly repressed the outgrowth of aortic ring cells at 6 days after culture, while silencing of miR-24 seemed not to affect aortic ring cell outgrowth. Taken together, these data suggest that miR-24 represses angiogenesis in vitro and ex vivo.

Repression of Retinal Vascular Development by miR-24 In Vivo.

To study the function of miR-24 in retinal vascular development in vivo, the inventors have generated transgenic mice in which miR-24 is induced when the transgenic mice are crossed to mice expressing Cre recombinase. These mice were viable and crossed to CAG-Cre mice to generate miR-24 transgenic (TG) mice. When measured by northern blot with miR-24 Starfire™ probe, there was a ~3-fold increase in miR-24 expression in the transgenic mice when normalized to a U6 15 control (FIG. 20A). miR-24TG pups appeared significantly smaller than wildtype (WT) control littermates ($p<0.0001$). By weight, while the WT littermates weighed about 4.5 g, the miR-24 TG P6 pups weighed about 3.0 g. When P6 pups were stained with ICAM-2 for retinal vasculature, a significant delay in retinal vascular development was observed although the retinas were similar in size. As shown in FIGS. 20B-C, compared to the wild-type and CAG-Cre control mice, P6 miR-24TG mice showed significant decreased retinal vascular density and sprouting distance. The inventors further examined the retinal vasculature in the adult mice. The retinal vasculature of adult miR-24TG mice also appeared to show less density compared to WT controls by Isolectin B4 staining (FIG. 20D, right panel). By confocal microscopy, the superficial layer of the retinal vasculature was similar in miR-24TG mice to that in WT mice (FIG. 20D, left panel). However, as opposed to the WT mice, the superficial layer of retinal vasculature in miR-24 TG mice failed to sprout into the intermediate and deeper layers (FIG. 20D, middle panels). These results indicate that overexpression of miR-24 in mice impairs postnatal retinal vasculature development.

Repression of Laser-Induced CNV by miR-24 Mimic in Mice.

Figure 21D:
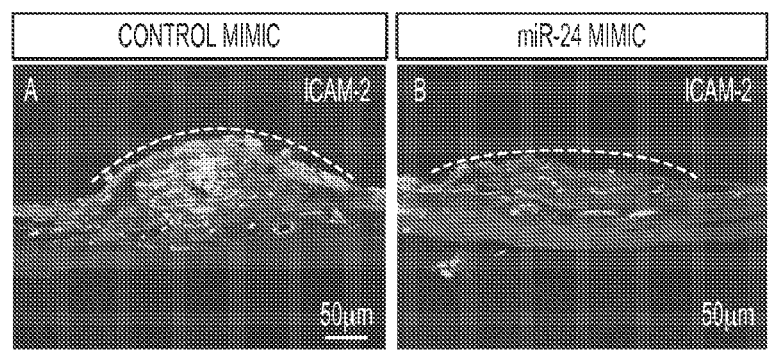

Previous results have shown that miR-23~27~24 members were upregulated in the retina/choroid in a laser-induced CNV mouse model. To test whether miR-24 overexpression represses laser-induced neovascularization in the choroid, miR-24 mimic was injected subretinally into mice at 0, 4 and 9 days after laser injury, and CNV was quantified at 2 weeks post injury after ICAM-2 staining and confocal flat mount imaging. First, the inventors tested the efficiency of miRNA mimic delivery. To do so, FAM-labeled miR-24 mimic was injected subretinally into mice at 7 days after laser injury, and the distribution of labeled mimics was visualized by ICAM-2 co-staining and flatmount imaging 4 days later. miR-24 mimic was successfully delivered into the injured region of the retina and partially overlapping with the vasculature (data not shown). By real-time RT-PCR, 1 µl of miR-24 mimic (200 ng/µl) injection led to an approximately 20-fold increase in miR-24 expression in the posterior eye cup (FIG. 21A). These indicate efficient delivery of miRNA mimics into the choroid by subretinal injection in vivo. The inventors next examined the effect of miR-24 mimic on laser-induced CNV in mice. Quantification of the CNV area revealed that miR-24 overexpression led to about 60% decrease in the neovascularization of the choroid (3031±496 µm2, N=33 in the mimic control, verses 1243±317 µm2, N=36 in miR-24 mimic injected samples (FIGS. 21B-C)). Compared to the saline control, the control mimic led to a small but insignificant decrease in CNV (P=0.31). Decreased neovascularization of the choroid was also confirmed by ICAM-2 staining of frozen sections (FIG. 21D). These results indicate that miR-24 is sufficient to repress CNV in vivo.

Mimicking of miR-24 Overexpression Angiogenic Phenotype by PAK4 or LIMK2 Silencing In Vitro.

Given the in vitro and in vivo evidence that miR-24 represses angiogenesis, the inventors set to further dissect the mechanism by which miR-24 regulates cytoskeleton dynamics and angiogenesis. miR-24 target gene DIAPH1, LIMK2 or PAK4 was silenced with siRNAs in HUVECs, and actin cytoskeleton structure and distribution was visualized with phalloidin staining. As shown by Western blot in FIG. 22A, siRNAs against DIAPH1, LIMK2 and PAK4 were efficient in silencing their respective genes when transfected at either 50 nM or 100 nM concentration in HUVECs. The inventors also designed siRNA to silence LIMK1, and found that LIMK2 siRNA didn't affect the expression of its family member LIMK1, and vice versa, suggesting the specificity of the siRNAs. Functionally, silencing of LIMK1, LIMK2 or PAK4 also decreased the level of phosphorylated Cofilin, consistent with them being upstream of ADF/Cofilin/F-actin pathway. Phalloidin staining revealed that, compared to control siRNA, silencing of LIMK2 or PAK4, and to a less extent DIAPH1, disrupted stress fibers in HUVECs (FIG. 22B). In the case of LIMK2 silencing, cells appeared smaller and rounder, and actin aggregates were observed near to the nucleus. Because of the potential redundancy between LIMK1 and LIMK2, the inventors also checked the effect of LIMK1 silencing in HUVECs independently (FIG. 5A). Surprisingly, silencing of LIMK1 did not affect stress fiber formation. This indicates that, instead of LIMK1, LIMK2 plays a major role in regulating actin cytoskeleton dynamics in HUVECs.

Our results showed that miR-24 can decrease the level of phosphorylated Cofilin through PAK4/LIMK2 pathways, which therefore increase non-phosphorylated Cofilin and actin depolymerization. Based on these, the inventors hypothesized that knockdown of Cofilin in ECs may rescue the stress fiber defects in miR-24 overexpressing cells. They achieved efficient COFILIN silencing in HUVECs with specific siRNAs. Indeed, knockdown of Cofilin in ECs at least partially rescued the disappearance of the stress fibers and small cell size in miR-24 overepressing ECs, indicating that PAK4/LIMK2/Cofilin pathway mediates miR-24 function in regulating actin cytoskeleton.

To further study whether silencing of miRNA target genes mimics the phenotype of miR-24 overexpression in angiogenesis, an in vitro Matrigel tube formation assay was performed after siRNA silencing of the miR-24 target genes in HUVECs. Consistent with the essential role of LIMK2 and PAK4 in actin skeleton dynamics, knockdown of LIMK2 or PAK4 blocked ECtube formation in the Matrigel (FIG. 22C). However, knockdown of DIAPH1 or LIMK1 only had a mild effect in EC tube formation (FIG. 22C). Quantification of angiogenic tube formation also showed a dramatic decrease in branch points in the Matrigel after LIMK2 or PAK4 silencing, and a slight decrease after DIAPH1 or LIMK1 knockdown. The inventors further performed experiments to determine whether EC proliferation and migration is repressed by LIMK2 or PAK4 knockdown. Consistently, LIMK2 or PAK4 silencing led to a significant decrease in cell migration after scratch wound and cell proliferation by BrDU incorporation assay (FIGS. 22D-E). These results indicate that LIMK2 and PAK4 silencing recapitulates the phenotype of miR-24 overexpression in actin cytoskeleton dynamics and angiogenesis in vitro, suggesting LIMK2 and PAK4 as important miR-24 target genes mediating its function in angiogenesis.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

U.S. Pat. No. 5,844,107
U.S. Pat. No. 5,877,302
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Pat. No. 6,693,187
U.S. Pat. No. 6,838,283
U.S. Pat. No. 7,067,641
U.S. Publn. 20020150626
U.S. Publn. 20030032615
U.S. Publn. 20030203865
U.S. Publn. 20040048787
Ambros, *Cell*, 113(6):673-676, 2003.
Amrite et al., *Expert Opin. Drug Deliv.* 7(5):631-645, 2010.
Angel et al., *Cell*, 49:729, 1987b.
Angel et al., *Mol. Cell. Biol.*, 7:2256, 1987a.
Augustin & Kirchhof, *Expert Opin. Ther. Targets* 13(6):641-651, 2009.
Axton et al., *J. Cell. Biochem.* 103(4):1171-1182, 2008.
Baichwal et al., In: *Gene Transfer*, Kucherlapati (Ed.), Plenum Press, NY, 117-48, 1986.
Banerji et al., *Cell*, 27(2 Pt 1):299-308, 1981.
Banerji et al., *Cell*, 33(3):729-740, 1983.
Bartel, *Cell*, 116:281-297, 2004.
Benvenisty and Neshif, *Proc. Natl. Acad. Sci. USA*, 83(24):9551-9555, 1986.
Berkhout et al., *Cell*, 59:273-282, 1989.
Blanar et al., *EMBO J.*, 8:1139, 1989.
Bodine et al., *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brennecke et al., *Cell*, 113:25-36, 2003.
Bressler, *Ophthalmology* 116(10 Suppl):S1-7, 2009.
Brown et al., *N Engl. J. Med.* 355(14):1432-1444, 2006.
Bulla et al., *J. Virol.*, 62:1437, 1986.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campa et al., *Invest. Ophthalmol. Vis. Sci.* 49(3):1178-1183, 2008.
Campo et al., *Nature*, 303:77, 1983.
Care et al., *Nat. Med.* 13:613-618, 2007.
Carmeliet & Tessier-Lavigne, *Nature* 436(7048):193-200, 2005.
Carrington et al. *Science*, 301(5631):336-338, 2003.
Casci et al., *Cell* 96(5):655-665, 1999.
Celander and Haseltine, *J. Virology*, 61:269, 1987.
Celander et al., *J. Virology*, 62:1314, 1988.
Chhabra et al., *Mol. Cancer.* 9:232, 2010.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Cell*, 126:321-334, 2006.
Chang et al., *Mol. Cell. Biol.*, 9:2153, 1989.
Chang et al., *Nature*, 430(7001):785-789, 2004.
Chang et al., *Proc. Natl. Acad. Sci. USA*, 102:8120-8125, 2005.
Chatterjee et al., *Proc. Natl. Acad. Sci. USA*, 86:9114, 1989.
Chen and Okayama, *Mol. Cell. Biol.*, 7(8):2745-2752, 1987.
Chen et al., *Science*, 303(5654):83-86, 2004.
Choi et al., *Cell*, 53:519, 1988.
Cohen et al., *J. Cell. Physiol.*, 5:75, 1987.
Costa et al., *Mol. Cell. Biol.*, 8:81, 1988.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.

De Villiers et al., *Nature*, 312(5991):242-246, 1984.
Deschamps et al., *Science*, 230:1174-1177, 1985.
Dhanabal et al., *Cancer Biol Ther* 4(6):659-668, 2005.
Distler et cd., Q. *J. Nuc.l Med.* 47(3):149-161, 2003.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
EPO 0273085
Fatkin et al., *J. Clin. Invest.*, 106(11):1351-1359, 2000.
Fechheimer, et al., *Proc Natl. Acad. Sci. USA*, 84:8463-8467, 1987.
Feng and Holland, *Nature*, 334:6178, 1988.
Ferkol et cd., *FASEB J.*, 7:1081-1091, 1993.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Friedman et al., *Genes Devel.*, 3:1314, 1989.
Friedman, *Br. J. Ophthalmol.* 88(2):161-163, 2004.
Friedman et al., *Genome Res.* 19(1):92-105, 2009.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Giroux et al., *Curr. Biol.*, 9:369-372, 1999.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Graham and Van Der Eb, *Virology*, 52:456-467, 1973.
Greene et al., *Immunology Today*, 10:272, 1989
Grisanti & Tatar, *Prog. Retin. Eye Res.* 27(4):372-390, 2003.
Grosschedl and Baltimore, *Cell*, 41:885, 1985.
Harland and Weintraub, *J. Cell Biol.*, 101(3):1094-1099, 1985.
Harris et al., *Proc. Natl. Acad. Sci. USA*, 105:1516-1521, 2008.
Haslinger et al., *Proc. Natl. Acad. Sci. USA*, 82:8572, 1985.
Hauber et al., *J. Virology*, 62:673, 1988.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Hirochika et al., *J. Virol.*, 61:2599, 1987.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra et al., *Nature*, 323:555, 1986.
Imler et al., *Mol. Cell. Biol.*, 7:2558, 1987.
Impagnatiello et al., *J. Cell. Biol.* 152(5):1087-1098, 2001.
Imperiale et al., *Mol. Cell. Biol.*, 4:875, 1984.
Jager et al., *N. Engl. J. Med.* 358(24):2606-2617, 2008.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jennewein et al., *J. Biol. Chem.* 285(16):11846-11853, 2010.
Johnson et al., *Mol. Cell. Biol.*, 9:3393, 1989.
Kadesch and Berg, *Mol. Cell. Biol.*, 6:2593, 1986.

Kaneda et al., *Science*, 243:375-378, 1989.
Karin et al., *Mol. Cell. Biol.*, 7:606, 1987.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kiledjian et al., *Mol. Cell. Biol.*, 8:145, 1988.
Kimura et al., *Dev. Growth Differ.* 39(3):257-265, 1997.
Kiriazis and Kranias, *Annu. Rev. Physiol.*, 62:321-351, 2000.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Krützfeldt et al., *Nature*, 438:685-689, 2005.
Kuehbacher et al., *Circ. Res.*, 101:59-68, 2007.
Kuhl et al., *Cell*, 50:1057, 1987.
Kunz et al., *Nucl. Acids Res.*, 17:1121, 1989.
Lagos-Quintana et al., *Curr. Biol.*, 12:735-739, 2002.
Lagos-Quintana et al., *Science*, 294(5543):853-858, 2001.
Lagos-Quintana et al., *Curr Biol.* 12:735-739, 2002.
Lal et al., *Mol. Cell.* 35(5):610-625, 2009.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Lee and Ambros, *Science*, 294(5543):862-864, 2001.
Lee et al., *Nature*, 294:228, 1981.
Lee et al., *Biochem. Biophys. Res. Commun.* 346(1):83-88, 2006.
Levinson et al., *Nature*, 295:79, 1982.
Lin et al., *Mol. Cell. Biol.*, 10:850, 1990.
Lowes et al., *J. Clin. Invest.*, 100(9):2315-2324, 1997.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Ma et al., *Cancer Lett.* 298(2):150-158, 2010.
Majors et al., *Proc. Natl. Acad. Sci. USA*, 80:5866, 1983.
Maragkakis et al. *Nucleic Acids Res.* 37(Web Server issue):W273-276, 2009.
Matsuda & Cepko, *Proc. Natl. Acad. Sci. USA* 101(1):16-22, 2004.
McNeall et al., *Gene*, 76:81, 1989.
Meister et al., *Nature*, 431:343-9, 2004.
Michael et al., *Mol Cancer Res.* 1:882-891, 2003.
Miksicek et al., *Cell*, 46:203, 1986.
Moreau et al., *Nucl. Acids Res.*, 9:6047, 1981.
Muesing et al., *Cell*, 48:691, 1987.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Omitz et al., *Mol. Cell. Biol.*, 7:3466, 1987.
Ondek et al., *EMBO J.*, 6:1017, 1987.

Palmiter et al., *Nature*, 300:611, 1982.
Papadopoulos et al., *Bioinformatics* 25(15):1991-1993, 2009.
Pasquinelli and Ruvkun, *Ann. Rev. Cell Dev. Biol.*, 18:495-513, 2002.
PCT Appln. WO 0071096
Pech et al., *Mol. Cell. Biol.*, 9:396, 1989.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Poliseno et al., *Blood* 108(9):3068-307, 2006.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen et al., *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Resendez et al., *Mol. Cell. Biol.*, 8:4579, 1988.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *N Engl. J. Med.* 355(14):1419-1431, 2006.
Ryan, *Arch. Ophthalmol.* 100(11):1804-1809, 1982.
Sakai et al., *Genes and Dev.*, 2:1144, 1988.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp et al., *Cell*, 59:229, 1989.
Shaul et al., *EMBO J.*, 6:1913, 1987.
Shen et al., *Mol. Ther.* 16(7):1208-1216, 2008.
Sherman et al., *Mol. Cell. Biol.*, 9:50, 1989.
Sleigh et al., *J. EMBO*, 4:3831, 1985.
Small & Olson, *Nature* 469(7330):336-342, 2011.
Spalholz et al., *Cell*, 42:183, 1985.
Spandau et al., *J. Virology*, 62:427, 1988.
Spandidos & Wilkie, *EMBO J.*, 2:1193, 1983.
Stahl et al., *Invest. Ophth. Vis. Sci.* 51(6):2813-2826, 2010.
Stephens et al., *Biochem. J.*, 248:1, 1987.
Stuart et al., *Nature*, 317:828, 1985.
Suarez et al., *Circ. Res.*, 100:1164-1173, 2007.
Sullivan et al., *Mol. Cell. Biol.*, 7:3315, 1987.
Swartzendruber et al., *J. Cell. Physiology*, 85:179, 1975.
Takebe et al., *Mol. Cell. Biol.*, 8:466, 1988.
Tavernier et al., *Nature*, 301:634, 1983.
Taylor et al., *Mol. Cell. Biol.*, 10:165, 1990a.
Taylor et al., *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Tobe et al., *Am. J. Pathol.* 153(5):1641-1646, 1998.
Toyofuku et al., *Genes Dev.* 18(4):435-447, 2004.
Treisman, *Cell*, 46(4):567-174, 1986
Tronche et al., *Mol. Biol. Med.*, 7:173, 1990.
Tronche et al., *Mol. Cell. Biol.*, 9(11):4759-4766, 1989.
Trudel et al., *Genes and Dev.*, 6:954, 1987.
Tur-Kaspa et al., *Mol. Cell. Biol.*, 6:716-718, 1986.
Tyndell et al., *Nuc. Acids. Res.*, 9:6231, 1981.
Urbich et al., *Cardiovasc. Res.* 79(4):581-588, 2008.
Vannice et al., *J. Virology*, 62:1305, 1988.
Vasseur et al., *Proc Natl. Acad. Sci. USA*, 77:1068, 1980.
Wagner et al., *Proc. Natl. Acad. Sci. USA* 87(9):3410-3414, 1990.
Walker & Harland, *Genes Dev.* 23(9):1046-1051, 2009.
Wang & Olson, *Curr. Opin. Genet. Dev.* 19(3):205-211, 2009.
Wang et al., *Cell*, 47:241, 1986.
Wang et al., *Proc. Natl. Acad. Sci. USA*, 105:7738-7743, 2008a.
Wang et al., *Dev Cell* 15(2):261-271, 2008b.
Weber et al., *Cell*, 36:983, 1984.
Weinberger et al. *Mol. Cell. Biol.*, 8:988, 1984.
Winoto et al., *Cell*, 59:649, 1989.
Wong et al., *Gene*, 10:87-94, 1980.
Wu and Wu, Biochemistry, 27: 887-892, 1988.
Wu and Wu, *J. Biol. Chem.*, 262:4429-4432, 1987.
Xu et al., *Curr. Biol.*, 13:790-795, 2003.
Yang et al., *Proc. Natl. Acad. Sci. USA*, 87:4144-4148, 1990.
Yang et al., *Nat. Med.* 13:486-491, 2007.
Yuan et al., *BMC Syst. Biol.* 3:65, 2009.
Yutzey et al. *Mol. Cell. Biol.*, 9:1397, 1989.
Zachary, *Neurosignals* 14(5):207-221, 2005.
Zelenin et al., *FEBS Lett.*, 287(1-2):118-120, 1991.
Zeng et al., *Cancer Res.*, 62(13):3630-3635, 2002.
Zhou et al., *PLoS Pathog* 5(12):e1000681, 2009.

The invention claimed is:

1. A method of treating age-related wet macular degeneration (AMD) comprising administering to a subject (a) antagonists of miR-23 function and miR-27 function, (b) an antagonist of miR-23 function or miR-27 function and an agonist of miR-24 function, or (c) antagonists of miR-23 function and miR-27 function and an agonist of miR-24.

2. The method of claim 1, comprising administering antagonists of miR-23 function and miR-27 function.

3. The method of claim 1, comprising administering an antagonist of miR-23 function and an agonist of miR-24 function.

4. The method of claim 1, comprising administering an antagonist of miR-27 function and an agonist of miR-24 function.

5. The method of claim 1, comprising administering antagonists of miR-23 function and miR-27 function and an agonist of miR-24.

6. The method of claim 1, wherein said subject is a non-human animal.

7. The method of claim 1, wherein said subject is a human.

8. The method of claim 1, wherein said antagonists are miR antagomirs or antisense molecules and said agonist is miR-24 or a mimic thereof.

9. The method of claim 1, wherein said agonists/antagonists are formulated in a lipid delivery vehicle.

10. The method of claim 8, wherein said mimic, miR-24, antagomirs or antisense molecules contain at least one non-natural base.

11. The method of claim 1, wherein said antagonist is delivered to the eye, to the ocular vasculature or systemically.

12. The method of claim 1, further comprising administering to said subject a secondary anti-AMD therapy.

13. The method of claim 1, wherein treating comprises slowing the progression of disease and/or improving the vision of said subject.

14. A method of treating a pathologic neovascular disease state or condition comprising administering to a subject (a) antagonists of miR-23 function and miR-27 function, (b) an antagonist of miR-23 function in combination with an agonist of miR-24 function, or (c) antagonists of miR-23 function and miR-27 function in combination with an agonist of miR-24.

15. The method of claim 14, wherein said disease state or condition is selected from cancer, atherosclerosis, coronary artery disease, age-related macular degeneration, diabetic retinopathy, or retinopathy of prematurity.

16. The method of claim 14, comprising administering antagonists of miR-23 function and miR-27 function, but not an agonist miR-24.

17. The method of claim 14, comprising administering an antagonist of miR-23 function and an agonist of miR-24 function.

18. The method of claim 14, comprising administering antagonists of miR-23 function and miR-27 function and an agonist of miR-24.

19. The method of claim 14, wherein said antagonists are miR antagomirs or antisense molecules and said agonist is miR-24 or a mimic thereof.

20. The method of claim 14, wherein said agonist/antagonists are formulated in a lipid delivery vehicle.

21. The method of claim 19, wherein said agonist, miR-24, antagomirs or antisense molecules contain at least one non-natural base.

22. The method of claim 15, further comprising administering to said subject a secondary therapy for cancer, atherosclerosis, coronary artery disease, age-related macular degeneration, diabetic retinopathy, or retinopathy of prematurity.

* * * * *

UNITED STATES PATENT AND TRADEMARK OFFICE
CERTIFICATE OF CORRECTION

PATENT NO. : 9,598,694 B2  
APPLICATION NO. : 14/398330  
DATED : March 21, 2017  
INVENTOR(S) : Shusheng Wang, Eric Olson and Qinbo Zhou Page 1 of 1

It is certified that error appears in the above-identified patent and that said Letters Patent is hereby corrected as shown below:

On the Title Page

Item (71) Applicant, insert --The Administrators of the Tulane Educational Fund, New Orleans, LA (US)--.

Signed and Sealed this
Twenty-sixth Day of June, 2018

Andrei Iancu
*Director of the United States Patent and Trademark Office*

UNITED STATES PATENT AND TRADEMARK OFFICE
CERTIFICATE OF CORRECTION

PATENT NO. : 9,598,694 B2
APPLICATION NO. : 14/398330
DATED : March 21, 2017
INVENTOR(S) : Shusheng Wang et al.

It is certified that error appears in the above-identified patent and that said Letters Patent is hereby corrected as shown below:

In the Specification

In Column 1, Line 12, insert:
--This invention was made with government support under grant number EY021862 awarded by The National Institutes of Health. The government has certain rights in the invention.--.

Signed and Sealed this
Seventh Day of July, 2020

Andrei Iancu
*Director of the United States Patent and Trademark Office*